(12) United States Patent
Quake et al.

(10) Patent No.: US 8,129,176 B2
(45) Date of Patent: *Mar. 6, 2012

(54) INTEGRATED ACTIVE FLUX MICROFLUIDIC DEVICES AND METHODS

(75) Inventors: Stephen R. Quake, Stanford, CA (US); Hou-Pu Chou, Foster City, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/536,129

(22) Filed: Aug. 5, 2009

(65) Prior Publication Data

US 2010/0120018 A1  May 13, 2010

Related U.S. Application Data

(63) Continuation of application No. 10/801,361, filed on Mar. 15, 2004, now Pat. No. 7,622,081, which is a continuation of application No. 09/875,438, filed on Jun. 5, 2001, now Pat. No. 6,767,706, which is a continuation-in-part of application No. 09/724,548, filed on Nov. 28, 2000, now Pat. No. 7,351,376.

(60) Provisional application No. 60/209,243, filed on Jun. 5, 2000, provisional application No. 60/211,309, filed on Jun. 13, 2000, provisional application No. 60/249,360, filed on Nov. 16, 2000.

(51) Int. Cl.
*G01N 33/53* (2006.01)

(52) U.S. Cl. ............... 435/287.2; 435/6.19; 422/504; 251/331; 251/335.2; 417/437; 417/474

(58) Field of Classification Search .............. 436/503; 435/6; 422/103
See application file for complete search history.

(56) References Cited

U.S. PATENT DOCUMENTS 2,656,508 A   10/1953   Coulter
(Continued)

FOREIGN PATENT DOCUMENTS

EP   0 592 094 A2   4/1994
(Continued)

OTHER PUBLICATIONS

A. Y. Fu, et al., "A Microfabricated Fluorescence-Activated Cell Sorter," Nature Biotechnology, Nov. 1999, vol. 17, pp. 1109-1111.
(Continued)

*Primary Examiner* — In Suk Bullock
*Assistant Examiner* — Timothy G Kingan
(74) *Attorney, Agent, or Firm* — Kilpatrick Townsend & Stockton LLP

(57) ABSTRACT

The invention relates to a microfabricated device for the rapid detection of DNA, proteins or other molecules associated with a particular disease. The devices and methods of the invention can be used for the simultaneous diagnosis of multiple diseases by detecting molecules (e.g. amounts of molecules), such as polynucleotides (e.g., DNA) or proteins (e.g., antibodies), by measuring the signal of a detectable reporter associated with hybridized polynucleotides or antigen/antibody complex. In the microfabricated device according to the invention, detection of the presence of molecules (i.e., polynucleotides, proteins, or antigen/antibody complexes) are correlated to a hybridization signal from an optically-detectable (e.g. fluorescent) reporter associated with the bound molecules. These hybridization signals can be detected by any suitable means, for example optical, and can be stored for example in a computer as a representation of the presence of a particular gene. Hybridization probes can be immobilized on a substrate that forms part of or is exposed to a channel or channels of the device that form a closed loop, for circulation of sample to actively contact complementary probes. Universal chips according to the invention can be fabricated not only with DNA but also with other molecules such as RNA, proteins, peptide nucleic acid (PNA) and polyamide molecules.

18 Claims, 22 Drawing Sheets

U.S. PATENT DOCUMENTS

| | | | |
|---|---|---|---|
| 3,560,754 A | 2/1971 | Kamentsky |
| 3,570,515 A | 3/1971 | Kinner |
| 3,747,628 A | 7/1973 | Holster et al. |
| 4,018,565 A | 4/1977 | Fletcher, III et al. |
| 4,046,159 A | 9/1977 | Pegourie |
| 4,119,368 A | 10/1978 | Yamazaki |
| 4,153,855 A | 5/1979 | Feingold |
| 4,245,673 A | 1/1981 | Bouteille et al. |
| 4,434,704 A | 3/1984 | Surjaatmadja |
| 4,581,624 A | 4/1986 | O'Connor |
| 4,585,209 A | 4/1986 | Aine et al. |
| 4,675,300 A | 6/1987 | Zare et al. |
| 4,786,165 A | 11/1988 | Yamamoto et al. |
| 4,898,582 A | 2/1990 | Faste |
| 4,908,112 A | 3/1990 | Pace |
| 4,963,498 A | 10/1990 | Hillman et al. |
| 4,992,312 A | 2/1991 | Frisch |
| 5,032,381 A | 7/1991 | Bronstein et al. |
| 5,085,562 A | 2/1992 | Van Lintel |
| 5,088,515 A | 2/1992 | Kamen |
| 5,096,388 A | 3/1992 | Weinberg |
| 5,126,022 A | 6/1992 | Soane et al. |
| 5,126,115 A | 6/1992 | Fujita et al. |
| 5,140,161 A | 8/1992 | Hillman et al. |
| 5,164,558 A | 11/1992 | Huff et al. |
| 5,164,598 A | 11/1992 | Hillman et al. |
| 5,171,132 A | 12/1992 | Miyazaki |
| 5,224,843 A | 7/1993 | Van Lintel |
| 5,259,737 A | 11/1993 | Kamisuki et al. |
| 5,265,327 A | 11/1993 | Faris et al. |
| 5,271,724 A | 12/1993 | van Lintel |
| 5,290,240 A | 3/1994 | Horres, Jr. |
| 5,336,062 A | 8/1994 | Richter |
| 5,346,372 A | 9/1994 | Naruse et al. |
| 5,375,979 A | 12/1994 | Trah |
| 5,376,252 A | 12/1994 | Ekstrom |
| 5,400,741 A | 3/1995 | DeTitta et al. |
| 5,417,235 A | 5/1995 | Wise et al. |
| 5,423,287 A | 6/1995 | Usami et al. |
| 5,434,049 A | 7/1995 | Okano et al. |
| 5,445,934 A | 8/1995 | Fodor et al. |
| 5,452,878 A | 9/1995 | Gravesen et al. |
| 5,454,472 A | 10/1995 | Benecke et al. |
| 5,486,335 A | 1/1996 | Wilding et al. |
| 5,498,392 A | 3/1996 | Wilding et al. |
| 5,500,071 A | 3/1996 | Kaltenbach et al. |
| 5,512,131 A | 4/1996 | Kumar et al. |
| 5,529,465 A | 6/1996 | Zengerle et al. |
| 5,558,998 A | 9/1996 | Hammond et al. |
| 5,580,523 A | 12/1996 | Bard |
| 5,589,136 A | 12/1996 | Northrup et al. |
| 5,593,130 A * | 1/1997 | Hansson et al. ............. 251/61.1 |
| 5,632,876 A | 5/1997 | Zanzucchi et al. |
| 5,641,400 A | 6/1997 | Kaltenbach et al. |
| 5,642,015 A | 6/1997 | Whitehead et al. |
| 5,659,171 A | 8/1997 | Young et al. |
| 5,660,370 A | 8/1997 | Webster |
| 5,661,222 A | 8/1997 | Hare |
| 5,681,024 A | 10/1997 | Lisec et al. |
| 5,702,618 A | 12/1997 | Saaski et al. |
| 5,705,018 A | 1/1998 | Hartley |
| 5,716,852 A | 2/1998 | Yager et al. |
| 5,726,404 A | 3/1998 | Brody |
| 5,726,751 A | 3/1998 | Altendorf et al. |
| 5,750,015 A | 5/1998 | Soane et al. |
| 5,757,482 A | 5/1998 | Fuchs et al. |
| 5,759,014 A | 6/1998 | Van Lintel |
| 5,775,371 A | 7/1998 | Pan et al. |
| 5,788,468 A | 8/1998 | Dewa et al. |
| 5,800,690 A | 9/1998 | Chow et al. |
| 5,833,926 A | 11/1998 | Wurzel et al. |
| 5,836,750 A | 11/1998 | Cabuz |
| 5,837,200 A | 11/1998 | Diessel et al. |
| 5,837,832 A | 11/1998 | Chee et al. |
| 5,842,787 A | 12/1998 | Kopf-Sill et al. |
| 5,852,495 A | 12/1998 | Parce |
| 5,856,174 A | 1/1999 | Lipshutz et al. |
| 5,863,801 A | 1/1999 | Southgate et al. |
| 5,869,004 A | 2/1999 | Parce et al. |
| 5,875,817 A | 3/1999 | Carter |
| 5,876,187 A | 3/1999 | Afromowitz et al. |
| 5,880,071 A | 3/1999 | Parce et al. |
| 5,904,824 A | 5/1999 | Oh |
| 5,932,799 A | 8/1999 | Moles |
| 5,942,443 A | 8/1999 | Parce et al. |
| 5,948,227 A | 9/1999 | Dubrow |
| 5,965,001 A | 10/1999 | Chow et al. |
| 6,007,309 A | 12/1999 | Hartley |
| 6,007,690 A | 12/1999 | Nelson et al. |
| 6,015,531 A | 1/2000 | Colin et al. |
| 6,042,709 A | 3/2000 | Parce et al. |
| 6,043,080 A * | 3/2000 | Lipshutz et al. ............ 435/287.2 |
| 6,103,199 A | 8/2000 | Bjornson et al. |
| 6,117,634 A | 9/2000 | Langmore et al. |
| 6,123,769 A | 9/2000 | Sanjoh |
| 6,155,282 A | 12/2000 | Zachary et al. |
| 6,174,365 B1 | 1/2001 | Sanjoh |
| 6,221,654 B1 | 4/2001 | Quake et al. |
| 6,296,673 B1 | 10/2001 | Santarsiero et al. |
| 6,318,970 B1 | 11/2001 | Backhouse |
| 6,345,502 B1 | 2/2002 | Tai et al. |
| 6,361,958 B1 * | 3/2002 | Shieh et al. ................... 435/7.1 |
| 6,409,832 B2 | 6/2002 | Weigl et al. |
| 6,540,895 B1 | 4/2003 | Quake et al. |
| 6,767,706 B2 * | 7/2004 | Quake et al. ..................... 435/6 |
| 6,833,242 B2 | 12/2004 | Quake et al. |
| 6,949,385 B1 * | 9/2005 | Burns et al. ................... 436/180 |
| 6,960,437 B2 | 11/2005 | Enzelberger et al. |
| 7,601,270 B1 * | 10/2009 | Unger et al. .................... 216/22 |
| 2001/0027745 A1 | 10/2001 | Weigl et al. |
| 2002/0037499 A1 | 3/2002 | Quake et al. |
| 2003/0008308 A1 | 1/2003 | Enzelberger et al. |
| 2004/0115838 A1 | 6/2004 | Quake et al. |

FOREIGN PATENT DOCUMENTS

| | | |
|---|---|---|
| EP | 0 703 364 A1 | 3/1996 |
| EP | 0 706 004 A2 | 4/1996 |
| EP | 0 745 682 B1 | 12/1996 |
| EP | 0 778 351 B1 | 6/1997 |
| EP | 0 779 436 A2 | 6/1997 |
| EP | 0 829 360 A2 | 3/1998 |
| EP | 0 845 603 A1 | 6/1998 |
| EP | 0 999 055 A2 | 5/2000 |
| GB | 2 155 152 A | 9/1985 |
| GB | 2 264 296 A | 8/1993 |
| GB | 2 264 496 A | 9/1993 |
| GB | 2 308 460 A | 6/1997 |
| JP | 09043251 A | 2/1997 |
| WO | WO 91/13338 A2 | 9/1991 |
| WO | WO 91/15750 A1 | 10/1991 |
| WO | WO 94/05414 A1 | 3/1994 |
| WO | WO 95/33846 A1 | 12/1995 |
| WO | WO 95/33853 A1 | 12/1995 |
| WO | WO 97/02357 A1 | 1/1997 |
| WO | WO 97/38300 A1 | 10/1997 |
| WO | WO 98/07069 A1 | 2/1998 |
| WO | WO 98/08931 A1 | 3/1998 |
| WO | WO 98/45481 A1 | 10/1998 |
| WO | WO 98/52691 A1 | 11/1998 |
| WO | WO 99/00655 A2 | 1/1999 |
| WO | WO 99/04361 A1 | 1/1999 |
| WO | WO 99/17093 A1 | 4/1999 |
| WO | WO 99/52633 A1 | 10/1999 |
| WO | WO 99/61888 A2 | 12/1999 |
| WO | WO 00/00678 A1 | 1/2000 |
| WO | WO 00/22434 A1 | 4/2000 |
| WO | WO 00/43748 A1 | 7/2000 |
| WO | WO 00/60345 A1 | 10/2000 |
| WO | WO 01/09595 A2 | 2/2001 |
| WO | WO 01/09595 A3 | 2/2001 |
| WO | WO 01/34302 A2 | 5/2001 |
| WO | WO 01/45843 A2 | 6/2001 |
| WO | WO 01/89695 A2 | 11/2001 |

OTHER PUBLICATIONS

A.T. Woolley, et al., "Capillary Electrophoresis Chips with Intergrated Electrochemical Detection," Analytical Chemistry, Feb. 15, 1998, vol. 70, No. 4, pp. 684-688.

Affholter, Joseph et al., "Engineering a Revolution," Chemistry in Britain, pp. 48-51, Apr. 1999.

Ahn, Chong H. et al., "Fluid Micropumps Based on Rotary Magnetic Actuators," Proceedings of 1995 IEEE Micro Electro Mechanical Systems Workshop (MEMS '95), Amsterdam, Netherlands, pp. 408-412, 1/29-21211995.

Alan Van Orden, et al., "High-throughput flow cytometric DNA fragment sizing," Anal. Chem., Jan. 1, 2000, vol. 72(1), pp. 37-41.

Anderson, Janelle R. et al., "Fabrication of Topologically Complex Three-Dimensional Microfluidic Systems in PDMS by Rapid Prototyping," Analytical Chemistry, vol. 72, No. 14, pp. 3158-3164, Jul. 15, 2000.

Anderson, Rolfe C. et al., "Microfluidic Biochemical Analysis System," Transducers '97, 1997 International Conference on Solid-State Sensors and Actuators, Chicago, Illinois, pp. 477-480, Jun. 16-19, 1997.

Angell, et al., "Silicon Micromechanical Devices," Scientific American, Apr. 1983, 248: pp. 44-55.

Armani, Deniz et al., "Re-Configurable Fluid Circuits by PDMS Elastomer Micromachining," IEEE In!. Conf. Micro Electro Mech. Sys!. Tech. Digest, vol. 12, pp. 222-227, 1999.

Arnold, Frances H., "Design by Directed Evolution," Accounts of Chemical Research, vol. 31, No. 3, pp. 125-131, 1998.

Ashkin, A. et al., "Optical Trapping and Manipulation of Single Cells Using Infrared Laser Beams," Nature, vol. 330, No. 24, pp. 769-771,12131/1987.

Ashkin: A. et al., "Optical Trapping and Manipulation of Viruses and Bacteria," Science, vol. 235, . pp. 1517-1520,Mar. 20, 1987.

Ballantyne, J. P. et al., "Selective Area Metallization by Electron-Beam Controlled Direct Metallic Deposition," J. Vac. Sci. Technol., vol. 10, No. 6, pp. 1094-1097, Nov. 1973.

Bein, Thomas, "Efficient Assays for Combinatorial Methods for the Discovery of Catalysts," Angew. Chem. In!. Ed., vol. 38, No. 3, pp. 323-326, 1999.

Benard, W. L. et al., "A Titanium-Nickel Shape-Memory Alloy Actuated Micropump," Transducers C15'97, 1997 International Conference on Solid-State Sensors and Actuators, Chicago, Illinois, pp. 361-364, Jun. 16-19, 1997.

Biochips, Nature Biotechnology, vol. 18, Supplement 2000, pp. IT43-IT44, 2000.

Bloomstein, T. M. et al., "Laser-Chemical Three-Dimensional Writing for Microelectromechanics and Application to Standard-Cell Microfluidics," J. Vac. Sci. Technol. B, vol. 10, No. 6, pp. 2671-2674,Nov. 1992.

Bousse, Luc et al., Electrokinetically Controlled Microfluidic Analysis Systems: Annu. Rev. Biophys. Biomol. Struct., vol. 29, pp. 155-181, 2000.

Brechtel, R. et al., "Control of the Electroosmotic Flow by Metal-Salt-Containing Buffers," Journal of Chromatography A, vol. 716, pp. 97-105,1995.

Bryzek, Janusz et al., "Micromachines on the March", IEEE Spectrum, vol. 31, No. 5, pp. 20-31, May 1994.

Buchaillot, Lionel et al., "Silicon Nitride Thin Films Young's Modulus Determination by an Optical Non Destructive Method," Jpn. J. Appl. Phys., vol. 36, Part 2, No. 6B, pp. L794-L797, Jun. 15, 1997.

Budowle, Bruce et al., "Analysis of the VNTR Locus DIS80 by the PCR Followed by High-Resolution PAGE," Am. J. Hum, Genet., vol. 48, pp, 137-144, 1991.

Buican, Tudor N. et al., "Automated Single-Cell Manipulation and Sorting by Light Trapping," Applied Optics, vol. 26, No. 24, pp. 5311-5316, Dec. 15, 1987.

Burbaum, Jonathan J. et al., "New Technologies for High-Throughput Screening," Current Opinion in Chemical Biology, vol. 1, pp. 72-78, 1997.

Busch, J. et al., Methods for the Differentiation of Microorganisms, Journal of Chromatography B, vol. 722, pp. 263-278, 1999.

Cai, Weiwen, et ai "High-Resolution Restriction Maps of Bacterial Artificial Chromosomes Constructed by Optical Mapping," Proc. Natl. Acad. Sci. USA, vol. 95, pp. 3390-3395, Mar. 1998.

Calkins, Kathryn, "Mycometrix: Rubber Chips," BioCentury, 2 pages, Oct. 16, 2000.

Castro, A., et al., "Fluorescence Detection and Size Measurement of Single DNA Molecules," Analytical Chemistry, Apr. 1, 1993, vol. 65, pp. 849-852.

Chan, Jason H. et al., Microfabricated Polymer Devices for Automated Sample Delivery of Peptides for Analysis by Electrospray Ionization Tandem Mass Spectrometry: Analytical Chemistry, vol. 71, No. 20, pp. 4437-4444, Oct. 15, 1999.

Chapter 9: Microfluidic Devices, Micromachined Transducers Sourcebook, pp. 779-882, 1998.

Chiang, Yuh-Min et al., Characterizing the Process of Cast Molding Microfluidic Systems: SPIE, vol. 3877, pp. 303-311, Sep. 1999.

Chiu, Chi-Sung et al., Single Molecule Measurements Calibrate Green Fluorescent Protein Surface -C29 Densities on Transparent Beads for Use With 'Knock-In' Animals and Other Expression Systems: Jornal of Neuroscience Methods, vol. 105, pp. 55-63, 2001.

Chiu, Daniel T. et al., "Patterned Deposition of Cells and Proteins Onto Surfaces by Using Three-Dimensional Microfluidic Systems," PNAS, vol. 97, No. 6, pp. 2408-2413, Mar. 14, 2000.

Chou, Hou-Pu et al., "A Microfabricated Rotary Pump," Biomedical Microdevices, vol. 3, No. 4, pp. 323-330, 2001.

Chou, Hou-Pu et al., "Disposable Microdevices for DNA Analysis and Cell Sorting," Proc. Solid-State Sensor and Actuator Workshop, Hilton Head, South Carolina, pp. 11-14,Jun. 8-11, 1998.

Chou, Hou-Pu et al., "Integrated Elastomer Fluidic Lab-On-A-Chip-Surface Patterning and DNA Diagnostics," Proceedings of the Solid State Actuator and Sensor Workshop, Hilton Head, South Carolina, 4 pages, 2000.

Chou, Hou-Pu et al., "Microfabricated Devices for Sizing DNA and Sorting Cells," Micro- and Nanofabricated Structures and Devices for Biomedical Environmental Applications, Proceedings of SPIE, vol. 3258, pp. 181-187, 1998.

Chou, Hou-Pu et al., "Multiple Disease Diagnostics on a Single Chip," Biophysics Lab, Caltech, pp. 1-4, Mar. 1, 2000.

Chou, Hou-Pu, "Microfabricated Devices for Rapid DNA Diagnostics," Doctoral Thesis, California Institute of Technology, pp. i-xii and 1-106,May 30, 2000.

Crosland-Taylor, P. J., "A Device for Counting Small Particles Suspended in a Fluid Through a Tube," Nature, vol. 171, pp. 37-38,Jan. 3, 1953.

D.J. Harrison, et al., "Micromachining a Miniaturized Cappillary Electrophoresis-Based Chemical Analysis System on a Chip," Science, Aug. 13, 1993, vol. 26, pp. 895-897.

Davila, Herman Moreno, "Molecul!3r and Functional Diversity of Voltage-Gated Calcium Channels," Annals of the New York Academy of Sciences, vol. 868, pp. cover, 102-117, 1999.

Dharmatilleke, Saman et al., "Three-Dimensional Silicone Device Fabrication and Interconnection Scheme for Microfluidic Applications Using Sacrificial Wax Layers," Micro-Electro-Mechanical Systems (MEMS), vol. 2, pp. 413-418, 2000.

Duffy, David C. et al., "Patterning Electroluminescent Materials With Feature Sizes as Small as 5pm Using Elastomeric Membranes as Masks for Dry Lift-Off," Advanced Materials, vol. 11, No. 7, pp. 546-552, 1999.

Duffy, David C. et al., "Rapid Prototyping of Microfluidic Switches in Poly(dimethyl siloxane) and Their Actuation by Electro-Osmotic Flow," J. Micromech. Microeng., vol. 9, pp. 211-217,1999.

Duffy, David C. et al., "Rapid Prototyping of Microfluidic Systems in Poly(dimethylsiloxane)," Analytical Chemistry, vol. 70, No. 23, pp. 4974-4984,Dec. 1, 1998.

E. Delamarche, et al., "Patterned Delivery of Immunoglobulins to Surfaces Using Microfluidic Networks," Science, May 2, 1997, vol. 276, pp. 779-781.

Effenhauser, Carlo S. et al., "Integrated Capillary Electrophoresis on Flexible Silicone Microdevices: Analysis of DNA Restriction Fragments and Detection of Single DNA Molecules on Microchips," Analytical Chemistry, vol. 69, No. 17, pp. 3451-3457, Sep. 1, 1997.

Effenhauser, Carlo S. et al., "Integrated Chip-Based Capillary Electrophoresis," Electrophoresis, vol. 18, pp. 2203-2213, 1997.

Electro Microfluidic Dual In-Line Package (EMDIP), Sandia National Laboratories, 2 pages, no date.

Ericson, Christer et al., "Electroosmosis-And Pressure-Driven Chromatography in Chips Using Continuous Beds," Analytical Chemistry, vol. 72, No. 1, Jan. 1, 2000.

Fahrenberg, J. et al., "A Microvalve System Fabricated by Thermoplastic Molding," J. Micromech. Microeng., vol. 5, pp. 169-171, 1995.
Fetiinger, J. C. et al., "Stacked Modules for Micro Flow Systems in Chemical Analysis: Concept and Studies Using an Enlarged Model," Sensors and Actuators B, vol. 17, pp. 19-25, 1993.
Figeys, Daniel et al., "An Integrated Microfluidics-Tandem Mass Spectrometry System for Automated Protein Analysis," Analytical Chemistry, vol. 70, No. 18, pp. 3727-3734, Sep. 15, 1998.
Figeys, Daniel et al., "Nanoflow Solvent Gradient Delivery From a Microfabricated Device for Protein Identifications by Electrospray Ionizatio Mass Spectrometry," Analytical Chemistry, vol. 70, No. 18, pp. 3721-3727, Sep. 15, 1998.
Foich, A. et al., "Molding of Deep Polydimethylsiloxane Microstructures for Microfluidics and Biological Applications," Journal of Biomechanical Engineering, vol. 121, pp. 28-34, Feb. 1999.
Fuiwyier, M. J., "Electronic Separation of Biological Cells by Volume," Science, pp. 910-911, Nov. 1965.
G. Whitesides, Y. Xia, "Soft Lithography," Angewandte Chemie International Edition 37, 1998, vol. 37, pp. 550-575.
Galambos, Paul et al., "Electrical and Fluidic Packaging of Surface Micromachined Electro-Microfluidic Devices," 8 pages, no date.
Gao, Jun et al., "Integrated Microfluidic System Enabling Protein Digestion, Peptide Separation, and Protein Identification," Analytical Chemistry, vol. 73, No. 11, pp. 2648-2655, Jun. 1, 2001.
Gass, V. et al., "Integrated Flow-Regulated Silicon Micropump," Sensors and Actuators A, vol. 43, pp. 335-338, 1994.
Gerlach, Torsten, "Pumping Gases by a Silicon Micro Pump With Dynamic Passive Valves," Transducers '97, 1997 International Conference on Solid-State Sensors and Actuators, Chicago, Illinois, pp, 357-360, Jun. 16-19, 1997.
Giusti, Alan et al., "Application of Deoxyribonucleic Acid (DNA) Polymorphisms to the Analysis of DNA Recovered From Sperm," Journal of Forensic Science, vol. 31, No. 2, pp. ~09-417, Apr. 1986.
Goii, C. C et al., "Microvalves With Bistable Buckled Polymer Diaphragms," J. Micromech. Microeng., vol. 6, pp. 77-79, 1996.
Gonzalez, Jesus E. et al., "Improved Indicators of Cell Membrane Potential That Use Fluorescence Resonance Energy Transfer," Chemistry &Biology, vol. 4, No. 4, pp. 269-277, Apr. 1997.
Goodwin, P.M., et al., "Rapid sizing of individual fluoresecently stained DNA fragments by flow cytometry," Nucleic Acids Research, 1993, vol. 21, No. 4, pp. 803-806.
Gravesen, Peter et al., "Microfluidics—A Review," J. Micromech. Microeng., vol. 3, pp. 168-192, 1993.
Greene, Chana, "Characterizing the Properties of PDMS," pp. 1-11, Summer 2000.
Guérin, L. J. et al., "Simple and low Cost Fabrication of Embedded Micro-Channels by Using a New Thick-Film Photoplastic," Transducers '97, 1997 International Conference on Solid-State Sensors and Actuators, Chicago, Illinois, pp. 1419-1422, Jun. 18-19, 1997.
Hanes, Jozef, et al., "In Vitro Selection and Evolution of Functional Proteins by Using Ribosome Display," Proc. Natl. Acad. Sci. USA, vol. 94, pp. 4937-4942,May 1997.
Henion, Jack et al., "Capillary Electrophoresis/Mass Spectrometry: From One Meter Capillaries to Chip-Based Devices," 2 pages, 1999.
Hermanson; Greg T. et al., "Chapter 2—Activation Methods," Immobilized Affinity Ligand Techni.<lues, Academic Press, pp. 2 cover pages, 51-136, 1992.
Hicks, Jennifer, "Genetics ~nd Drug Discovery Dominate Microarray Research," R&D Magazine, pp. 28-33, Feb. 1999.
Hoffmuller, Ulrich et al., "In Vitro Evolution and Selection of Proteins: Ribosome Display for Larger Libraries," Angew. Chem. Int. Ed., vol. 37, No. 23, pp. 3241-3243,1998.
Hopfgartner, Gerard et al., "Exact Mass Measurement of Product Ions for the Structural Elucidation of Drug Metabolites With a Tandem Quadrupole Orthogonal Acceleration Time-Of-Flight Mass Spectrometer," Journal of the American Society for Mass Spectrometry, vol. 10, pp. cover, 1305-1314, Dec. 1999.
Horn, Howard, "Lab Chips Sector: Microtechnologies Are Changing Healthcare and More," Life Sciences, pp. 19-21, Mar. 20, 2001.
Hornbeck, Larry J. et al., "Bistable Deformable Mirror Device," Spatial Light Modulators and Applications 1988 Technical Digest Series, Summaries of papers presented at the Spatial Light Modulators and Applications Topical Meeting, Optical Society of America, vol. 8, Postconference Edition, A215, pp. 107-110,6/15-1711988.
Hosokawa, Kazuo et al., "Droplet-Based Nano/Picoliter Mixer Using Hydrophobic Microcapillary Vent," 1999 IEEE International Conference on Micro Electro Mechanical Systems, Technical Digest, pp. 388-393, 1999.
Hosokawa, Kazuo et al., "Handling of Picoliter Liquid Samples in a Poly(dimethylsiloxane)-Based Microfluidic Device," Analytical Chemistry, vol. 71, No. 20, pp. 4781-4785,Oct. 15, 1999.
Hou-Pu Chou, et al., "A microfabricated device for sizing and sorting DNA molecules," PNAS, Jan. 1999, vol. 96, pp. 11-13.
Ikuta, Koji et al., "Three Dimensional Micro Integrated Fluid Systems (MIFS) Fabricated by Stereo Lithography," IEEE, pp. 1-6, 1994.
J.P. Brody, et al., "Low Reynolds number micro-fludic devices," In Proc. of Solid-State Sensor and Actuator Workshop, Jun. 1996, pp. 105-108.
J.P. Nolan, et al., "The emergence of flow cytometry for sensitive, real-time measurements of molecular interactions," Nature Biotechnology, Jul. 1998, vol. 16, pp. 633-638.
Jacobson, Ken et al., "International Workshop on the Application of Fluorescence Photobleaching Techniques to Problems in Cell Biology," Federation Proceedings, vol. 42, No. 1, pp. 72-79,Jan. 1983.
Jacobson, Stephen C. et al., "High-Speed Separations on a Microchip," Analytical Chemistry, vol. 66, No. 7, pp. 1114-1118,Apr. 1, 1994.
Jacobson, Stephen C. et al., "Microfluidic Devices for Electrokinetically Driven Parallel and Serial Mixing," Analytical Chemistry, vol. 71, No. 20, pp. 4455-4459,Oct. 15, 1999.
Jeffreys, Alec J. et al., "Hypervariable 'Minisatellite' Regions in Human DNA," Nature, vol. 314, pp. 67-73, Mar. 7, 1985.
Jerman, Hal, "Electrically-Activated, Normally-Closed Diaphragm Valves," Transducers '91, 1991 International Conference on Solid-State Sensors and Actuators, pp. cover, 1045-1048, 1991.
Jermutus, Lutz, et al., "Recent Advances in Producing and Selecting Functional Proteins by Using Cell-Free Translation," Current Opinion in Biotechnology, vol. 9, pp. 534-548, 1998.
Jo, Byung-Ho et al., "Fabrication of Three-Dimensional Microfluidic Systems by Stacking Molded Polydimethylsiloxane (PDMS) Layers" SPIE, vol. 3877, pp. 222-229, Sep. 1999.
Jo, Byung-Ho et al., "Three-Dimensional Micro-Channel Fabrication in Polydimethylsiloxane (PDMS) Elastomer," Journal of Microelectromechanical Systems, vol. 9, No. 1, pp. 76-81, Mar. 2000.
Joel S. Bader, et al., "DNA transport by a micromachined Brownian ratchet device," PNAS, Nov. 9, 1999., vol. 96(23), pp. 13165-13169.
Ju, L1-Ya et al., "Application of Silver Staining to the Rapid Typing of the Polymo~phism of HLA-DQ Alleles by Enzymatic Amplification and Allele-Specific Restriction Fragment Length Polymorphism," Electrophoresis, vol. 12, pp. 270-273, 1991.
Jung, D. R. et al., "Chemical and Physical Interactions at Metal/Self-Assembled Organic Monolayer Interfaces," pp. 1-54, 1994.
Kagan, C. R., "Organic-Inorganic Hybrid Materials as Semiconducting Channels in Thin-Film Field-Effect Transistors," Science, vol. 286, pp. 945-947, Oct. 29, 1999.
Kanter, Evan et al., "Analysis of Restriction Fragment Length Polymorphisms in Deoxyribonucleic Acid (DNA) Recovered From Dried Bloodstains," Journal of Forensic Sciences, vol. 31, No. 2, pp. 403-408, Apr. 1986.
Kapur, Ravi et al., "Fabrication and Selective Surface Modification of 3-Dimensionally Textured Biomedical Polymers From Etched Silicon Substrates," Journal of Biomedical Materials Research, vol. 33,pp. 205-216,1996.
Kawano, Yasushi et al., "Rapid Isolation and Identification of Staphylococcal Exoproteins by Reverse Phase Capillary High Performance Liquid Chromatography-Electrospray Ionization Mass Spectrometry," FEMS Microbiology Letters, vol. 189, pp. 103-108,2000.
Keller, Richard A. et al., "Single-Molecule Fluorescence Analysis in Solution," Applied Spectroscopy, vol. 50, No. 7, pp. 12A-30A, Jul. 1996.

Kenis, Paul J. A. et al., "Microfabrication Inside Capillaries Using Multiphase Laminar Flow Patterning," Science, vol. 285, pp. 83-85, 7/211999.
Khoo, Melvin et al., "A Novel Micromachined Magnetic Membrane Microfluid Pump," pp. 1-4, no date.
Kim, Enoch et al., "Micromolding in Capillaries: Applications in Materials Science," J. Am. Chem. Soc., vol. 118, No. 24, pp. 5722-5731,1996.
Kim, Enoch et al., "Polymer Microstructures Formed by Moulding in Capillaries," Nature, vol. 376, pp. 581-584, 8/1711995.
Kirk-Othmer, "Concise Encyclopedia of Chemical Technology," John Wiley & Sons, 5 pages, no date.
Kopp, Martin U. et al., "Chemical Amplification: Continuous-Flow PCR on a Chip," Science, vol. 280, pp. 1046-1048, May 15, 1998.
Kuhn, Lawrence et al., "Silicon Charge Electrode Array for Ink Jet Printing," IEEE Transactions on Electron Devices, vol. ED-25, No. 10, Pt>. 1257-1260, Oct. 1978.
Kumar, Amit et al., "Features of Gold Having Micrometer to Centimeter Dimensions Can Be Formed Through a Combination of Stamping With an Elastomeric Stamp and an Alkanethiol 'Ink' Followed by Chemical Etching," Appl. Phys. Lett., vol. 63, No. 14, pp. 2002-2004,Oct. 4, 1993.
Kumar, Amit et al., "Patterning Self-Assembled Monolayers: Applications in Materials Science," Langmuir, vol. 10, pp. 1498-1511, 1994.
L.C. Waters, et al., "Microchip devices for cell lysis, multiplex PCR amplification, and electrophoretic sizing," Analytical Chemistry., Jan. 1, 1998, vol. 70, No. 1, pp. 158-162.
L1, Jianjun et al., "Integration of Microfabricated Devices to Capillary Electrophoresis-Electrospray Mass Spectrometry Using a Low Dead Volume Connection: Application to Rapid Analyses of Proteolytic Digests," Analytical Chemistry, vol. 71, No. 15, pp. 3036-3045, Aug. 1, 1999.
L1u, Hanghui et al., "Development of Multichannel Devices With an Array of Electrospray Tips for High-Throughput Mass Spectrometry," Analytical Chemistry, vol. 72, No. 14, pp. 3303-3310, Jul. 15, 2000.
Lagally, E. T. et al., "Single-Molecule DNA Amplification and Analysis in an Integrated Microfluidic Device," Analytical Chemistry, vol. 73, No. 3, pp. 565-570, 211/2001.
Lagally, Er.Ic T. et al., "Fully Integrated PCR-Capillary Electrophoresis Microsystem for DNA Analysis," Lab on a Chip, vol. 1, pp. 102-107,2001.
Lagally, Eric T. et al., "Monolithic Integrated Microfluidic DNA Amplification and Capillary Electrophoresis Analysis System," Sensors and Actuators B, vol. 63, pp. 138-146,2000.
Lammerink, T. S. J. et al., "Modular Concept for Fluid Handling Systems," IEEE, pp. 389-394, 1996.
Last Chance for Micromachines, The Economist Technology Quarterly, printed from website hltp:/lwww.economist.com/science/displayStory.cfm?StoryJD=442930 on Jan. 25, 2001, 8 pages, 121712000.
Lazar, Iulia M. et al., "Novel Microfabricated Device for Electrokinetically Induced Pressure Flow and Electrospray Ionization Mass Spectrometry," Journal of Chromatography A, vol. 892, pp. 195-201,2000.
Lessard, Guillaume A. et al., "A Scanning Apertureless Fluorescence Microscope," 8 pages, no date.
Levine, Leanna M. et al., "Measurement of Specific Protease Activity Utilizing Fluorescence Polarization," Analytical Biochemistry, vol. 247, pp. 83-88, 1997.
Licklider, Larry et al., "A Micromachined Chip-Based Electrospray Source for Mass Spectrometry," Analytical Chemistry, vol. 72, No. 2, pp. 367-375, Jan. 15, 2000.
Lin, L. Y. et al., "Free-Space Micromachined Optical Switches for Optical Networking," IEEE Journal of Selected Topics in Quantum Electronics, vol. 5, No. 1, pp. 4-9, Jan. 1999.
Lin, Yuehe et al., "Laser Micromachined Isoelectric Focusing Device on Polymer Substrate for Electrospray Mass Spectrometry," SPIE, vol. 3877, pp. 28-35, Sep. 1999.
Llopis, Juan et al., Ligand-Dependent Interactions of Coactivators Steroid Receptor Coactivator-1 and Peroxisome Proliferator-Activated Receptor Binding Protein With Nuclear Hormone Receptors Can Be Imaged in Live Cells and Are Required for Transcription: PNAS, vol. 97, No. 8, pp. 4363-4368, 4/112000.
Lötters, J C et al., "The Mechanical Properties of the Rubber Elastic Polymer Polydimethylsiloxane for Sensor Applications," J. Micromech. Microeng., vol. 7, pp. 145-147,1997.
Lucy, Charles A. et al., "Characterization of the Cationic Surfactant Induced Reversal of Electroosmotic Flow in Capillary Electrophoresis," Anal. Chem., vol. 68, pp. 300-305,1996.
M.A. Unger et al., "Monolithoc Microfabricated Valves and Pumps Using Multi-layer Soft Lithography," Science, Apr. 2000, vol. 288 (5463): pp. 113-116.
Mahajan, Nupam P.et al., "Novel Mutant Green Fluorescent Protein Protease Substrates Reveal the Activation of Specific Caspases During Apoptosis," Chemistry & Biology, vol. 6, No. 6, pp. 401-409,Jun. 1999.
Maluf, N., "An Introduction to Microelectromechanical Systems Engineering," Artech House Publishers, Boston London, pp. 42-45,Dec. 1999.
Manz, A. et al., .iMicromachining of Monocrystalline Silicon and Glass for Chemical Analysis Systems, Trends in Analytical Chemistry, vol. 10, No. 5, pp. 144-149, 1991.
Marshall, Sid, "Fundamental Changes Ahead for Lab Instrumentation," R&D Magazine,S pages, Feb. 1999.
Marsili, Ray, "Lab-On-A-Chip Poised to Revolutionize Sample Prep," R&D Magazine,S pages, Feb. 1999.
Maule, John, "Pulsed-Field Gel Electrophoresis," Molecular Biotechnology, vol. 9, pp. 107-126, 1998.
McDonald, J. Cooper et al., "Fabrication of Microfluidic Systems in Poly(dimethylsiloxane)," Electrophoresis, vol. 21, pp. 27-40, 2000.
Moldavan, Andrew, "Photo-Electric Technique for the Counting of Microscopical Cells," Science, vol. 80, No. 2069, pp. 188-189, Aug. 24, 1934.
Muller, Richard S. et al., "Surface-Micromachined Microoptical Elements and Systems," Proceedings of the IEEE, vol. 86, No. 8, pp. 1705-1720, Aug. 1998.
Murray, Vincent et al., "Detection of Polymorphisms Using Thermal Cycling With a Single Oligonucleotide on a DNA Sequencing Gel," Human Mutation, vol. 2, pp. 118-122, 1993.
N.H. Chiem, et al., "Mircochip Systems for Immunoassay: an Integrated Immunoreactor with Electrophoretic Separation for Serum Theophylline Determination," Clinical Chemistry, (1998), vol. 44, No. 3, p. 591.
Nagai, Yasuo et al., "A Fluorescent Indicator for Visualizing cAMP-Induced Phosphorylation in Vivo," Nature Biotechnology, vol. 18, pp. 313-316, Mar. 2000.
Nakamura, Yusuke et al., "Variable Number of Tanden Repeat (VNTR) Markers for Human Gene Mapping," Science, vol. 235, pp. 1616-1622,Mar. 27, 1987.
New Objective website, "What is Electrospray," www.newobjective,com/electrospray/electrospray.hlml, 4 pages, 9/2212000.
Oleschuk, Richard D. et al., "Analytical Microdevices for Mass Spectrometry," Trends in Analytical Chemistry, vol. 19, No. 6., pp. 379-388, 2000.
Olsson, Anders et al., "Simulation Studies of Diffuser and Nozzle Elements for Valve-Less Micropumps," Transducers '97,1997 International Conference on Solid-State Sensors and Actuators, Chicago, Illinois, pp. 1039-1042 , Jun. 16-19, 1997.
O'Reilly, Marie-Anne J, et al., "The Technique of Pulsed Field Gel Electrophoresis and its Impact on Molecular Immunology," Journal of Immunological Methods, vol. 131, pp. 1-13, 1990.
P.H. Li., D.J. Harrison, Analytical Chemistry 69, 1564(1997).
Parker, Gregory J. et al., "Development of High Throughput Screening Assays Using Fluorescence Polarization: Nuclear Receptor-ligand-Binding and Kinase/Phophatase Assays," Journal of Biomolecular Screening, vol. 5, No. 2, pp. 77-88, 2000.
Pethig, Ronald et al., "Applications of Dielectrophoresis in Biotechnology," Tibtech, vol. 15, pp. 426-432, Oct. 1997.
Petiy, Jeffrey T, et al., "Characterization of DNA Size Determination of Small Fragments by Flow Cytometry," Anal. Chem., vol. 67, pp. 1755-1761, 1995.
PROTANA website, "NanoES Products," www.protana.com/products/default.asp, 3 pages, Sep. 19, 2000.

Qin, Dong et al., "Elastomeric light Valves," Adv, Mater., vol. 9, No. 5, pp. 407-410, 1997.

Qin, Dong et al., "Photolithography With Transparent Reflective Photomasks," J. Vac. Sci. Technol. B, vol. 16, No. 1, pp. 98-103, Jan. 1998.

Quake, Stephen R. et al., "From Micro-To Nanofabrication With Soft Materials," Science, vol. 290, pp. 1536-1540, Nov. 24, 2000.

R.S. Kane, et al., "Patterning Proteins and Cells Using Soft Lithography," Biomaterials, 1999, vol. 20, pp. 2363-2376.

Rapp, R. et al., "L1GA Micropump for Gases and liquids," Sensors and Actuators A, vol. 40, pp. 57-61,Jan. 1994.

Roberts, Richard W. et'al., "RNA-Peptide Fusions for the in Vitro Selection of Peptides and Proteins," Proc. Natl. Acad. Sci. USA, vol. 94, pp. 12297-12302, Nov. 1997.

Rouhi, Maureen, "Sizing, Sorting DNA One Piece at a Time," C&EN, pp. 5-6, Jan. 11, 1999.

Roylance, Lynn Michelle et al., "A Batch-Fabricated Silicon Accelerometer," IEEE Transactions on Electron Devices, vol. ED-26, No. 12, pp. 1911-1917, Dec. 1979.

S. Fiedler, et al., "Dielectrophoretic Sorting of Particles and Cells in a Microsystem," Analytical Chemistry, May 1, 1998, vol. 70, pp. 1909-1915.

Samad, Akhtar et al., "Optical Mapping: A Novel, Single-Molecule Approach to Genomic Analysis," Genome Research, pp. 1-4, 1995.

Sanjoh, Akira et al., "Spatiotemporal Protein Crystal Growth Studies Using Microfluidic Silicon Devices," Journal of Crystal Growth, vol. 196, pp. 691-702, 1999.

Schasfoort, Richard B. M. et al., "Field-Effect Flow Control for Microfabricated Fluidic Networks," Science, vol. 286, pp. 942-945,Oct. 29, 1999.

Schomburg, W. K. et al., "Fabrication of Polymer Microcomponents With The AMANDA-Process," New Materials and Directions, Eurosensors XII, pp. 711-714, Jun. 13-16, 1998.

Schueller, Olivier J. A. et al., "Fabrication of Glassy Carbon Microstructures by Soft Lithography," Sensors and Actuators A, vol. 72, pp. 126-139, 1999.

Schwartz, David C. et al., "Optical Mapping Approaches to Molecular Genomics," Current Opinion in Biotechnology, vol. 8, pp. 70-74, 1997.

Seethala, Ramakrishna et al., "A Fluorescence Polarization Competition Immunoassay for Tyrosine Kinases," Analytical Biochemistry; vol. 255, pp. 257-262, 1998.

Shevchenko, Andrej et al., "Rapid 'de Novo' Peptide Sequencing by a Combination of Nanoelectrospray, Isotopic Labeling and a QuadrupolelTime-Of-Flight Mass Spectometer," Rapid Communications in Mass Spectrometry, vol. 11, pp. 1015-1024, 1997.

Shinohara, Jun et al., "A High Pressure-Resistance Micropump Using Active and Normally-Closed Valves," IEEE, pp. 86-91, 2000.

Shoji, Shuichi et al., "Smallest Dead Volume Microvalves for Integrated Chemical Analyzing Systems," Transducers '91, 1991 International Conference on Solid-State Sensors and Actuators, San Francisco, California, pp. cover, 1052-1055, 1991.

Shoji, Shuichi, "Fluids for Sensor Systems," Topics in Current Chemistry, vol. 194, pp. 167-188, 1998.

Smits, J.G., "Piezoelectric Micropump With Three Valves Working Peristaltically," Sensors and Actuators, vol. A21-A23, pp. 203-206,1990.

Sohn, L. L. et al., "Capacitance Cytometry: Measuring Biological Cells One by One," PNAS, vol. 97, No. 20, pp. 10687-10690,Sep. 26, 2000.

Stemmer, Willem P. C. et al., "Rapid Evolution of a Protein in vitro by DNA Shuffling," Nature, vol. 370, pp. 389-390, Aug. 4, 1994.

Sweet, Richard G., "Chapter 9—Flow Sorters for Biologic Cells," Flow Cytometry and Sorting, John Wiley & Sons, pp. 5 cover pages and 177-189, 1979.

Takahashi, Akiyuki et al., "Measurement of Intracellular Calcium," Physiological Reviews, vol. 79, No. 4, pp. 1089-1125, Oct. 1999.

Tatari, Zohreh et al., "HLA-Cw Allele Analysis by PCR-Restriction Fragment Length Polymorphism: Study of Known and Additional Alleies," Proc. Nail. Acad. Sci. USA, vol. 92, pp. 8803-8807, Sep. 1995.

Tawfik, Dan S. et al., "Man-Made Cell-Like Compartments for Molecular Evolution," Nature Biotechnology, vol. 16, pp. 652-656, Jul. 1998.

Thompson, L. F. et al., Introduction to Microlithography: 185th Meeting of the American Chemical Society, Seattle, WA, pp. 2 cover pages, 1-13,Mar. 20-25, 1983.

Thorsen, Todd et al., "Dynamic Pattern Formation in a Vesicle-Generating Microfluidic Device," Physical Review Letters, vol. 86, No. 18, pp. 4163-4166, Apr. 30, 2001.

Todd, Paul et al., "Chapter 12—Cell Electrophoresis," Flow Cytometry and Sorting, John Wiley & Sons, pp. 5 cover pages and 217-229, 1979.

Tufte, O. N. et al., "Silicon Diffused-Element Piezoresistive Diaphragms," Journal of Applied Physics, vol. 33, No. 11, pp. 3322-3327, Nov. 1962.

Ullmann's Encyclopedia of Industrial Chemistry, Sections 6 to 6.3, Topic: Carbon Black, Sixth Edition, 7 pages, 1999.

Unger, Marc A. et al., "Single-Molecule Fluorescence Observed With Mercury Lamp Illumination," Biotechniques, vol. 27, No. 5, pp. 1008-1014, Nov. 1999.

Van De Pol, F,C.M, et al., A Thermo-Pneumatic Actuation Principle for a Microminiature Pump and Other Micromechanical Devices: Sensors and Actuators, vol. 17, Nos. 1-2, pp. 139-143, May 3, 1989.

Van De Pol, F.C.M. et al., "Micro Liquid Handling Devices—A Review," Micro Systems Technologies, vol. 90, pp. 799-805, 1990.

Van Den Berg, A. et al., Micro Total Analysis Systems: Proceedings of the IJTAS '94 Workshop, University of Twente, The Netherlands, 17 pages, Nov. 21-22, 1994.

Van Dilla, M. A. et al., "Cell Microfluorometry: A Method for Rapid Fluorescence Measurement," Science, vol. 163, pp. 1213-1214, Mar. 14, 1969.

Van Dilla, Marvin A. et al., "Chapter 2—Introduction and Resume of Flow Cytometry and Sorting," Flow Cytometry and Sorting, John Wiley &Sons, pp. 5 cover pages and 11-37, 1979.

Verpoorte, Elisabeth M. J. et al., Three-Dimensional Micro Flow Manifolds for Miniaturized Chemical Analysis Systems, J. Micromech. Microeng., vol. 7, pp. 246-256, 1994.

Vieider, Christian et al., A Pneumatically Actuated Micro Valve With a Silicon Rubber Membrane for Integration With Fluid Handling Systems: Transducers '95, 8th International Conference on Solid-State Sensors and Actuators and Eurosensors IX, Stockholm, Sweden, pp. 284-286, Jun. 25-29, 1995.

Volkmuth, W. D. et al., DNA Electrodiffusion in a 2D Array of Posts, Physical Review Letters, vol. 72, No. 13, pp. 2117-2120, Mar. 28, 1994.

Volkmuth, W. D. et al., "DNA Electrophoresis in Microlithographic Arrays," Nature, vol. 358, pp. 600-602, Aug. 13, 1992.

Washizu, Masao et al., "Molecular Dielectrophoresis of Biopolymers," IEEE Transactions on Industry Applications, vol. 30, No. 4, pp. 835-843, Jul. 1994.

Whitesides, George M. et al., "Flexible Methods for Microfluidics," Physics Today, pp. 42-48, Jun. 2001.

Whitesides, George M. et al., "Soft Lithography in Biology and Biochemistry," Annu. Rev. Biomed. Eng., vol. 3, pp. 335-373, 2001.

Wilbur, James L. et al., "Lithographic Molding: A Convenient Route to Structures With Sub-Micrometer Dimensions," Adv. Mater., vol. 7, No. 7, pp. 649-652, 1995.

Wilm, Matthias et al., "Femtomole Sequencing of Proteins From Polyacrylamide Gels by Nano-Electrospray Mass Spectrometry," Nature, vol. 379, pp. 466-469, Feb. 1, 1996.

Xia, Younan et al., "Complex Optical Surfaces Formed by Replica Molding Against Elastomeric Masters," Science, vol. 273, pp. 347-349,Jul. 19, 1996.

Xia, Younan et al., "Micromolding of Polymers in Capillaries: Applications in Microfabrication," Chern. Mater., vol. 8, No. 7, pp. 1559-1566, 1996.

Xia, Younan et al., "Reduction in the Size of Features of Patterned SAMs Generated by Microcontact Printing With Mechanical Compression of the Stamp," Adv. Mater., vol. 7, No. 5, pp. 471-473, 1995.

Xu, Bing et al., "Making Negative Poisson's Ratio Microstructures by Soft Lithography," Adv. Mater., vol. 11, No. 14, pp. 1186-1189, 1999.

Xu, Jingdong et al., "Room-Temperature Imprinting Method for Plastic Microchannel Fabrication," Analytical Chemistry, vol. 72, No. 8, pp. 1930-1933, Apr. 15, 2000.

Xu, Xiang et al., "Detection of Programmed Cell Death Using Fluorescence Energy Transfer," Nucleic Acids Research, vol. 26, No. 8, pp. 2034-2035, 1998.

Xue, Qifeng et al., "Integrated Multichannel Microchip Electrospray Ionization Mass Spectrometry: Analysis of Peptides From On-Chip Tryptic Digestion of Melittin," Rapid Communications in Mass Spectrometry, vol. 11, 1253-1256, 1997.

Xue, Qifeng et al., "Multichannel Microchip Electrospray Mass Spectrometry," Analytical Chemistry, vol. 69, No. 3, pp. 426-430, Feb. 1, 1997.

Yang, T. J. et al., "An Apertureless Near-Field Microscope for Fluorescence Imaging," Applied Physics Letters, vol. 76, No. 3, pp. 378-380, Jan. 17, 2000.

Yang, Xing et al., "A Low Power MEMS Silicone/Parylene Valve," Solid-State Sensor and Actuator Workshop, Hilton Head Island, South Carolina, 4 pages, 617-11/1998.

Yang, Xing et al., "A MEMS Thermopneumatic Silicone Membrane Valve," IEEE 10th Annual International Workshop of Micro Electro Mechanical Systems, Nagoya, Japan, pp. cover, 114-118, Jan. 26-30, 1997.

Yazdi, Navid et al., "Micromachined Inertial Sensors," Proceedings of IEEE, vol. 86, No. 8, pp. 1640-1659, Aug. 1998.

Young, A. M. et al., "Contoured Elastic-Membrane Microvalves for Microfluidic Network Integration," Journal of Biomechanical Engineering, vol. 121, pp. 2-6, Feb. 1999.

Zaccolo, Manuela et al., "A Genetically Encoded, Fluorescent Indicator for Cyclic AMP in Living Cells," Nature Cell Biology, vol. 2, pp. 25-29, Jan. 2000.

Zengerle, R. et al., "A Micro Membrane Pump With Electrostatic Actuation," Micro Electro Mechanical Systems '92, TravemOnde, Germany, pp. 19-24, Feb. 4-7, 1992.

Zengerle, R. et al., "Performance Simulation of Microminiaturized Membrane Pumps," 7th International Conference on Solid-State Sensors and Actuators, Yokohama, Japan, pp. 2 cover pages, 106-109, Jun. 7-10, 1993.

Zhang, B. et al., Microfabricated Devices for Capillary Electrophoresis-Electrospray Mass Spectrometry: Analytical Chemistry, vol. 71, No. 15, pp. 3258-3264, Aug. 1, 1999.

* cited by examiner

INTEGRATED ACTIVE FLUX MICROFLUIDIC DEVICES AND METHODS

PRIORITY APPLICATIONS

This application is a continuation of application Ser. No. 10/801,361 filed Mar. 15, 2004; which is a continuation of application Ser. No. 09/875,438, filed Jun. 5, 2001, now U.S. Pat. No. 6,767,706; which is a continuation-in-part of U.S. patent application Ser. No. 09/724,548, filed Nov. 28, 2000, now U.S. Pat. No. 7,351,376. U.S. patent application Ser. No. 09/724,548 claims priority under 35 U.S.C. §119(e) to copending U.S. provisional patent application Ser. Nos. 60/209,243; 60/211,309; and 60/249,360 filed on Jun. 5, 2000; Jun. 13, 2000; and Nov. 16, 2000, respectively. Each of these priority applications hereby incorporated, by reference, in its entirety.

The present invention was made with Government support under Grant No. 5 R29 HG01642-03 awarded by the National Institutes of Health. The United States Government may have certain rights to this invention pursuant to these grants.

1. FIELD OF THE INVENTION

This invention relates to microfluidic devices and methods, including microfabricated multilayer elastomeric devices with active pumps and valves. More particularly, the devices and methods of the invention comprise a loop channel that is selectively open or closed to at least one input or output, and which actively circulates a fluid received in the loop. The loop can be closed by microvalves, for example elastomeric microvalves interposed between an inlet or outlet channel and the loop channel. Any fluid, such as a liquid (preferably aqueous), gas, slurry, etc. can be moved through fluid channels of the microfluidic device, which are typically on an elastomeric fluid layer and comprise the loop channel and its inlet and outlet channel or channels. Fluid within the loop is circulated, for example by active pumping, which can be done while the loop is open or closed to any or all channels that communicate with the loop channel. Pumping can be provided by a series of at least three microvalves which cooperate to form a peristaltic pump by cycling through an appropriate sequence of on/off or open/close steps.

Microvalves are formed and actuated by control lines or channels, typically on an elastomeric control layer adjacent to a fluid layer. A microvalve is formed by the elastomeric interchannel membrane separating a fluid channel on one layer and an appropriately placed control line on an adjacent layer, where the fluid channels and control lines cross. Fluid in a control line, preferably a pressurized gas and most preferably air, can selectively deform or release the interchannel membrane of a microvalve, to close or open the valve and restrict or permit flow in the adjacent cooperating fluid channel.

The loop channel can be provided with any reagents or reactants to be mixed or combined for any purpose, including any chemical reactions or interactions. In one embodiment, molecules are applied to a surface that is exposed to fluid circulating in the loop, to facilitate a desired interaction between the molecules and one or more components of the fluid. For example, DNA probes can be patterned onto spots in the loop channel for analysis of a DNA sample, by analyzing (e.g. imaging) any hybridization of probe DNA with sample DNA.

Thus, the devices and methods comprise integrated diagnostic chips with elastomeric channels, surface patterning, and surface chemistries adapted for multiparameter analysis of a sample, e.g. DNA hybridization. Flow control, reagent metering, in-line mixing, loop circulations, and "rotary" designs are also described. These devices can be used for "lab-on-a-chip" applications, for example to test for and diagnose multiple diseases. Devices and methods include detection of organisms or genetic disorders, or determining a genetic predisposition or susceptibility of humans and animals to genetic disorders, cancer and cancer-related diseases. Microfabricated chips of the invention can be used to measure gene expression, to detect the presence of pathogenic organisms or DNA, for DNA fingerprinting and forensic analysis, and for other applications in which molecules, viruses, particles, or cells and the like are analyzed, identified, evaluated, tested or sorted.

The invention also relates to methods for the rapid diagnosis of disease by detecting molecules (e.g. amounts of molecules), such as polynucleotides (e.g., DNA) or proteins (e.g., antibodies), by measuring the signal of a detectable reporter associated with the molecules (e.g., fluorescent, ultraviolet, radioactive, color change, or another signal). Preferably, the reporter or its signal is optically detectable. In these embodiments, a positive result (i.e. the presence or absence of the particular gene or antigen) is correlated to a signal from an optically-detectable reporter associated with hybridized polynucleotide or antigen/antibody complex. These polynucleotides or complexes can also be identified, assessed, or sorted (e.g. by size) in a microfabricated device that analyzes the polynucleotides according predetermined algorithms or characteristics, for example restriction fragment length polymorphism (RFLP).

Certain embodiments of the invention comprise an integrated microfluidic system with an array of diagnostic probes attached to a substrate. Multiple disease diagnosis of a sample can be done by using DNA hybridization, antibody/antigen reaction, or other detection methods. The loaded sample is actively moved in a loop on the device by a built-in peristaltic pump. Target DNA or antibodies in the sample, if any, associate or bind with their matching probes and give a positive signal of the corresponding diseases. The invention provides enhanced hybridization rates and improved speed and efficiency by active pumping, (e.g. ~20 minutes for 30 probes). The devices and methods of the invention are also accurate and require very little amount of sample, e.g. only a few microliters of total volume and a few target DNA molecules or antibodies for each disease; e.g. less than 100, preferably less than 50 molecules. The system is also advantageously small, typically 1 inch by 1 inch, and is easy and inexpensive to fabricate. It is disposable and thus eliminates cross-contamination. Many sample preparation and/or treatment steps can be incorporated into the device.

Other advantages include that multiple diseases can be diagnosed rapidly, contemporaneously or simultaneously on a single chip, e.g. in serial or in parallel, making disease diagnosis simpler and less costly. Automation can also be used. Another advantage is that there is no need to custom-design each chip for each application: the invention is highly flexible in design and use. Additional functions can be incorporated as desired, such as in-line digestion, separation i.e., for DNA fingerprinting or RFLP analysis and other techniques such as in situ-enzymatic labeling, PCR, etc. Small samples can be processed quickly, easily and accurately without the need for PCR, and thus without the potential costs, complications, errors or other disadvantages of PCR.

2. BACKGROUND OF THE INVENTION

Diagnosis of the sources, types and cures of diseases is usually done by doctors, based on symptoms and on simple tests and observations. Because there are so many similar diseases, further diagnoses are often required to precisely differentiate them, especially for diseases with infectious or genetic roots, such as HIV, tuberculosis, hepatitis and human BRCA1 breast cancer. Conventionally, disease diagnosis has been carried out by techniques such as bacterial culture or antibody/antigen reactions (1). Recently, molecular techniques such as DNA restriction fragment length polymorphism analysis (RFLP) have become more widely used for the detection of mutation-intense diseases or for genotyping specific pathogenic microorganisms, e.g. tuberculosis (80). However, relatively large sample volumes have been necessary and significant manipulation of the sample may be required. The conventional techniques are costly, time consuming and very labor-intensive. These methods may not work when only small samples are available. Rapid, contemporaneous, or simultaneous testing for more than one organism, disease characteristic, or parameter may be impractical or impossible.

DNA chips have been developed for disease diagnosis, using an array of various DNA hybridization probes laid down onto a solid substrate (2-4, 72-76, 81-83). The probes in these techniques are designed to react only with specific target DNA fragments from chosen disease entities. Nevertheless, hundreds of microliters to a few milliliters of sample are required to cover the chip. A further drawback is that is that the diffusion constant of DNA fragments is small, on the order of $\sim 10^{-7}$ cm$^2$/sec for 1-kbp DNA fragments (5). Thus, passive diffusion is an extremely slow process for large molecules such as DNA. Diffusion rates can be calculated using the equation:

$$l=\sqrt{Dt},$$

where l is diffusion length, D is the diffusion constant and t is time. If D is $10^{-7}$ cm$^2$/s for a typical 1 kbp DNA and t is one hour (3600 seconds), the diffusion length l is 0.19 mm. It follows that for passive diffusion of the DNA, each hybridization spot can only cover an area of about 0.4 mm in diameter. Even after one day i.e., 24 hours, only target samples in an area of ~2 mm in diameter can reach a specific probe to give a positive signal. Therefore, it takes a relatively long time for target DNA to be directed to complementary DNA probes. DNA may be lost or fail to find a matching probe, or will not do so in a reasonable time. PCR amplification may be needed to obtain enough DNA sample, which complicates the process and gives new sources of possible errors.

The invention addresses these and other problems. Microfluidic chips having elastomeric channels are provided, and an active flow of sample is delivered, for example by actively transporting a DNA or protein sample around a central loop within the device by a built-in (on-chip) peristaltic pump. The pumping action improves the efficiency of hybridization by directing the biological sample to it's target, which obviates the need for larger sample volumes and avoids the longer reaction times needed for passive devices (e.g. sample diffusion). A microfabricated or microfluidic device may be used to implement these techniques, for example to detect or separate labeled fragments. Microfluidic devices and related techniques have been described (11, 25 75-77, 84). These devices permit the manipulation, automatically if desired, of small volumes of biological samples on a small device, where reactions and diagnoses may be carried out.

The invention also encompasses the identification and separation of nucleic acid fragments by size, such as in sequencing of DNA or RNA. This is a widely used technique in many fields, including molecular biology, biotechnology, and medical diagnostics. The most frequently used conventional method for such separation is gel electrophoresis, in which different sized charged molecules are separated by their different rates of movement through a stationary gel under the influence of an electric current. Gel electrophoresis presents several disadvantages, however. The process can be time consuming, and resolution is typically about 10%. Efficiency and resolution decrease as the size of fragments increases; molecules larger than 40,000 base pairs are difficult to process, and those larger than 10 million base pairs cannot be distinguished.

Methods have been proposed for determination of the size of nucleic acid molecules based on the level of fluorescence emitted from molecules treated with a fluorescent dye. See Keller, et al., 1995 (42); Goodwin, et al., 1993 (39); Castro, et. al., 1993 (38); and Quake, et al., 1999 (70). Castro (38) describes the detection of individual molecules in samples containing either uniformly sized (48 Kbp) DNA molecules or a predetermined 1:1 ratio of molecules of two different sizes (48 Kbp and 24 Kbp). A resolution of approximately 12-15% was achieved between these two sizes. There is no discussion of sorting or isolating the differently sized molecules.

In order to provide a small diameter sample stream, Castro (38) uses a "sheath flow" technique wherein a sheath fluid hydrodynamically focuses the sample stream from 100 μm to 20 μm. This method requires that the radiation exciting the dye molecules, and the emitted fluorescence, must traverse the sheath fluid, leading to poor light collection efficiency and resolution problems caused by lack of uniformity. Specifically, this method results in a relatively poor signal-to-noise ratio of the collected fluorescence, leading to inaccuracies in the sizing of the DNA molecules.

Goodwin (39) mentions the sorting of fluorescently stained DNA molecules by flow cytometry. This method, employs costly and cumbersome equipment, and requires atomization of the nucleic acid solution into droplets, where each droplet contains at most one analyte molecule. Furthermore, the flow velocities required for successful sorting of DNA fragments were determined to be considerably slower than used in conventional flow cytometry, so the method would require adaptations to conventional equipment. Sorting a usable amount (e.g., 100 ng) of DNA using such equipment would take weeks, if not months, for a single run, and would generate inordinately large volumes of DNA solution requiring additional concentration and/or precipitation steps.

Quake (70) relates to a single molecule sizing microfabricated device (SMS) for sorting polynucleotides or particles by size, charge or other identifying characteristics, for example, characteristics that can be optically detected. The invention includes a fluorescence activated sorter (FAS), and methods for analyzing and sorting polynucleotides by measuring a signal produced by an optically-detectable (e.g., fluorescent, ultraviolet or color change) reporter associated with the molecules. These methods and microfabricated devices allow for high sensitivity, no cross-contamination, and lower cost than conventional gel techniques. In one embodiment of the invention, it has been discovered that devices of this kind can be advantageously designed for use in molecular fingerprinting applications, such as DNA fingerprinting.

These and other devices, including those which provide single molecule processing, can be used in combination with the loop channel and peristaltic pump devices of the invention. Likewise, other mechanisms of flow control, such as electroosmotics and electrophoresis, may be used in addition to or in combination with the loop channel, pump and valve arrangements described herein.

Given the current state of the art, it is desirable to provide new devices and methods for the rapid diagnosis of multiple diseases, e.g. by detecting the presence or absence of a particular gene. Such devices and methods may include analyzing and sorting differently sized nucleic acid or protein molecules with high resolution. It is likewise desirable to provide microfluidic chip designs having an architecture suitable for multiparameter analysis, including for example the rapid, contemporaneous or simultaneous evaluation of a sample in a battery of tests, for a plurality of characteristics, or against an array of targets or potential targets, for example by circulating sample in a loop channel for repeated exposure to a set of diagnostic probes.

3. SUMMARY OF THE INVENTION

The invention provides microfabricated devices and methods for the rapid detection of DNA, proteins, viruses or other molecules or particles, e.g. associated with a particular disease. The device includes a chip having a microfabricated analysis unit, preferably microfabricated in or onto a substrate of the chip. Each analysis unit includes a main channel in communication with a sample inlet channel, a target (e.g. hybridization) loop, and a detection region. The target loop is patterned with target molecules (e.g. polynucleotides or polypeptides). Additional channels may intersect or communicate with the target loop, on the same layer or on a different layer of the chip. Multilayer integrated or monolithic devices are preferred. The detection region may coincide with all or part of the target loop. The inlet channel may comprise a plurality of channels communicating with each other or with one or more reservoirs, or with one or more feed channels, to control flow or to deliver a plurality of reagents or samples. Typical devices also have an outlet channel, which may lead to an outlet reservoir. In a preferred embodiment, the target loop cooperates with a peristaltic pump assembly. Adjacent and downstream from the detection region, the main channel may have a discrimination region or branch point leading to at least two branch channels. In embodiments having an outlet channel, an outlet channel may be placed anywhere on the chip, but typically communicates with a main channel downstream of the detection region. Each channel may carry any fluid flow, e.g. a liquid (preferably an aqueous solution), a gas (preferably air), or a slurry.

Embodiments of these microfluidic devices are also provided which comprise a plurality of target loops, each of which is driven by a pump such as a peristaltic pump. The plurality of target loops in these devices may also be interconnected by microfluidic channels. For example, in one embodiment each target loop is connected to a common sample inlet and/or a common sample outlet by a common inlet or outlet channel, respectively. The inlet and/or outlet channels may, for example, be fluidly connected to a plurality of branch channels, with each branch channel connecting, in turn, to a particular target loop of the device. Alternatively, the plurality of target loops in these microfluidic devices may be connected to separate sample inlets and/or sample outlets, e.g., by a separate inlet or outlet channel.

In a preferred multilayer device, a pattern of fluid channels is fabricated on one layer, and a pattern of air channels is fabricated on a second layer. In operation, the fluid channels of the device carry any fluid, typically a liquid and most typically water or an aqueous solution or slurry. These channels are typically used to receive, process, analyze and work with samples and reagents, and may also be referred to as treatment channels. Air channels typically operate on another layer of the device and may intersect or communicate with fluid channels where adjacent layers of the device meet, for example at junctions or at the interface of two adjacent layers. The air channels may carry any pressurized flow of any fluid, liquid or gas, although air is generally preferred. The air channels are typically used to control the flow of fluid in the fluid or treatment channels, for example using air pressure, or by controlling microfabricated pumps and/or valves integrated on the chip. These channels can also be called control channels or control lines.

In certain embodiments, any layer of the device may have any kind of channel, in any pattern, array or arrangement. Channels in a multilayer device may also be made to encompass or transverse more than one layer, communicate with more than one layer, or to cross from one layer to another, for example by fabricating overlapping adjacent layers having overlapping channels which intersect or meet in any desired configuration or plane. Adjacent channels or layers in a multilayer may are not necessarily in contact with each other, and may be separated by gaps between layers or between channels. Openings may be made in channels as desired, for communication with other channels or layers, or for communication with a gap between layers, which for example may house or comprise one or more reservoirs. Any desired pattern or array of channels and intercommunications among and between them can be made by fabricating and joining corresponding negative molds of silicon elastomer according to the techniques described herein. See also, Unger et al. (6).

In preferred embodiments, fluid or treatment channels are not open or directly connected to air or control channels. That is, they are independent channel systems that do not directly feed into each other; they are sealed from each other and their contents do mix. The treatment and control channels interact with each other where they intersect to form a microvalve. When sufficient pressure, e.g. air pressure is applied to an air channel, the elastomeric membrane between the control channel and the treatment channel is deformed where the channels intersect. Sufficient pressure pinches, restricts or closes off the flow in the treatment channel, forming a closed microvalve. The valve is opened by releasing the pressure in the control channel. Thus, valves can be positioned as desired throughout a microfluidic device, each of which can be operated independently or in combination to control the processing and flow in the treatment channels.

These valves are actuated by moving a portion of the ceiling, roof or wall of a channels itself (i.e. a moving membrane). Valves and pumps produced by these techniques have a zero dead volume, and switching valves made by this technique have a dead volume approximately equal to the active volume of the valve, for example about $100 \times 100 \times 10 \, \mu m = 100$ pl. Such dead volumes and areas consumed by the moving membrane are approximately two orders of magnitude smaller than microvalves demonstrated to date. Experimentally, the response of such valves has been almost perfectly linear over a large portion of its-range of travel, with minimal hysteresis. Accordingly, the present valves are ideally suited for microfluidic metering and fluid control. The linear nature of the valve response demonstrates that the individual valves are well modeled as Hooke's Law springs. Furthermore, high pressures in the flow channel (i.e. back pressure) can be countered simply by increasing the actuation pressure. Experimentally, the present inventors have achieved valve closure at back pressures of 70 kPa, but higher pressures are also contemplated.

A preferred silicon elastomer for treatment and control channels is General Electric Silicon RTV 615, made by combining the components RTV 615A and RTV 615B. Transparent elastomers are particularly preferred. In certain embodiments, the treatment and control channels may be made in different molds, i.e. on different layers, using different elastomers.

Air pressure can be controlled for example using external (off-chip) three-way pneumatic valves such as model LHDA1211111H (Lee Company) to manipulate the on/off states of each individual microvalve. Valves may also be fabricated to have different stiffnesses, tolerances or thresholds, or different switching pressures, so that different valves will open and close at different pressures along one control channel. This may be determined, for example, by the elastomers used, by the shape and dimensions of the channels, by the distances or gaps between intersecting treatment and control channels, and by the thickness of the membrane between them.

Three microvalves in a series become a peristaltic pump when an appropriate on/off pumping sequence is applied. This causes successive waves of contraction along the treatment channels which propels the contents of the channel onward. For example, a flow of sample can be routed through the treatment channels as desired, by appropriately manipulating the valves to form a peristaltic pump that drives the fluid in the desired direction and through the desired channels. Valves can also be used to open and close channels as desired, to control the pattern and timing of flow.

In preferred embodiments, treatment channels are microfabricated into a transparent layer of a microfluidic device that is bonded to a glass or similar transparent or optically suitable probe substrate or coverslip, particularly in regions corresponding to the detection region. This provides access to the channel or channels for optical detection, for example by a high numerical aperture (NA) microscope. In a preferred embodiment, selected regions of the probe substrate corresponding to selected treatment channels are patterned with target or probe molecules, such as DNA, polynucleotide, protein, or antibody probes. DNA probes corresponding to a set of different diseases can be laid down on a target loop to form distinct hybridization spots. In this embodiment the target loop and its corresponding probe pattern preferably has a circular path on the face of the chip and its glass substrate. Any path of any shape can be used, although a path which can be selectively open and closed is preferred. For example, the path of a loop channel can be rectangular or square. The detection region in this embodiment comprises any or all of the target loop. That is, sample introduced to the chip, for example by capillary action, will enter the target loop, and molecules in the sample can bind to their corresponding probes on the glass substrate, if any. Binding can be detected using any suitable technique, including fluorescence, as described herein.

To improve the speed and accuracy of detection, minimize the amount of sample needed, and address diffusion issues, microvalves can be used to drive a peristaltic pumping action as described, which moves the sample around and around the target loop for continuous and or repeated exposure to the probes. The sample passes each probe several or many times, meaning that all sample molecules (e.g. DNA) will eventually and relatively quickly find and bind (hybridize) with matching targets (e.g. polynucleotide probes) at the right hybridization spots. Little or no sample is wasted, PCR amplification may not be needed, and heating (preferably intermittent) can be applied to denature false hybridizations and obtain more accurate results in successive passes through the target loop.

An object of the present invention is the simultaneous diagnosis of multiple diseases by detecting molecules (e.g. amounts of molecules), such as polynucleotides (e.g., DNA) or proteins (e.g., antibodies), by measuring the signal of a detectable reporter associated with the hybridized polynucleotides or antigen/antibody complexes.

An additional object of the invention is to provide a kit for the rapid diagnosis of disease.

A further object of the present invention is to provide algorithms for determining the existence of specific disease targets.

A still further object of the present invention is to determine the severity of a particular disease, for example according to the signal intensity from hybridization of a sample and target.

Another object of the present invention is to determine the susceptibility or predisposition of patients to a particular disease.

Yet another object of the present invention to provide methods for mixing two or more different fluids (i.e., fluids comprising different molecules or particles). Accordingly, the invention provides for the use of a microfluidic device to mix two or more different fluids.

Still another object of the present invention is to provide methods for binding a sample (e.g., of nucleic acids, polypeptides, cells, virions or other molecules and/or particles) to a target (for example, to a molecular probe, such as a complementary nucleic acid or an antibody probe). Accordingly, the invention also provides for the use of a microfluidic device to bind a sample to a target.

Additional objects of the invention include measuring gene expression levels; sequencing DNA; "fingerprinting" DNA sequences; measuring interaction of proteins, etc. with DNA sequences of length n (e.g. with all oligonucleotides of size n); and mutation and/or single nucleotide polymorphism (SNP) detection.

Other objectives will be apparent to persons of skill in the art.

In accomplishing these and other objectives, the invention provides a "lab-on-a-chip" device which utilizes several orders of magnitude lower sample volumes than conventional methods. For example, rather than using large sample volumes, a few droplets are enough. This reduces the use and cost of reagents and may reduce the risks to patients. The active design of the device increases the speed of the detection process significantly. A multiple disease diagnosis can be complete in a few minutes. Furthermore, the device is inexpensive and disposable, due in part to the materials used and the easy fabrication process. Automatic computer control can be easily integrated by controlling the switching of pneumatic valves via electronic driving circuits. Therefore, manual labor and chances of errors are greatly reduced. The invention offers flexibility of design and fabrication with the capability for many other functions.

In a preferred embodiment, the substrate of the device is planar, and contains a microfluidic chip made from a silicone elastomer impression of an etched silicon wafer according to replica methods in soft-lithography. See e.g. the devices and methods described in pending U.S. application Ser. No. 08/932,774 filed Sep. 25, 1997; No. 60/108,894 filed Nov. 17, 1998; No. 60/086,394 filed May 22, 1998; and Ser. No. 09/325,667 filed May 21, 1999 (molecular analysis systems). These methods and devices can further be used in combination with the methods and devices described in pending U.S. application Ser. No. 60/141,503 filed Jun. 28, 1999; Ser. No. 60/147,199 filed Aug. 3, 1999 and No. 60/186,856, filed Mar. 3, 2000 entitled "Microfabricated Elastomeric Valve and Pump Systems". Each of these references is hereby incorporated by reference in its entirety.

In a preferred embodiment, the microfabricated device is used for the identification of particular genes within the genome of pathogenic organisms, genetic disorders or genetic predisposition or susceptibility of humans or animals to cancer and cancer-related diseases. Microfabricated methods and devices are fast and require only small amounts of material, yet provides a high sensitivity, accuracy and reliability. In another embodiment, the microfabricated device can be used for detecting or sorting nucleotide fragments in a fingerprint according to size.

Microfabricated Device. The device includes a chip having a substrate with at least one microfabricated analysis unit. Each analysis unit includes a main channel, having a sample inlet, typically at one end, having along the length of the main channel a target or hybridization loop and a detection region, and having, an outlet or a branch point discrimination region adjacent and downstream of the detection region, leading to a waste channel or to a plurality of branch channels. In one embodiment two or more branch channels originate at the discrimination region and communicate with the main channel. The analysis unit also provides a stream or flow of solution, preferably but not necessarily continuous, which contains sample molecules and passes through the detection region. In certain embodiments the detection region comprises one or more regions of a target loop, is coextensive with the target loop, or comprises a region corresponding to each hybridization spot on the target loop. Thus, a device of the invention can comprise a plurality of detection regions, or one detection region comprising discrete test areas or hybridization spots, and detection can be serially, in parallel, or all at once. The presence, absence or level of reporter from each molecule is measured as it passes within the detection region. In a certain embodiments, on average only one molecule occupies one or more detection regions at a time. If desired, the molecule is directed to a selected branch channel based on the presence, absence or level of reporter. In other embodiments the molecule is held in the detection region, temporarily or permanently, for example by binding to a probe.

In a preferred embodiment, the substrate is planar, and contains a microfluidic chip made from a silicone elastomer impression of an etched silicon wafer using replica methods in soft-lithography (23). In one embodiment, the main channel meets branch channels to form a "T" (T junction) at a discrimination point. A Y-shaped junction, and other shapes and geometries may also be used. A detection region is typically upstream from the branch point. Molecules or cells are diverted into one or another outlet channel based on a predetermined characteristic that is evaluated as each molecule passes through the detection region. The channels are preferably sealed to contain the flow, for example by fixing a transparent coverslip, such as glass, over the chip, to cover the channels while permitting optical examination of one or more channels or regions, particularly the detection region. In a preferred embodiment the coverslip is pyrex, anodically bonded to the chip. Alternatively, the substrate may be an elastomer, which may prove advantageous when higher back pressures are used.

Other devices such as electrophoresis chips may also be used. Exemplary devices are described in U.S. Pat. Nos. 6,042,709; 5,965,001; 5,948,227; 5,880,690; and 6,007,690.

Channel Dimensions. The channels in a multiparameter molecular analysis device are preferably between about 10 µm and about 200 µm in width, typically 50-100 µm, and most preferably about 100 µm. The channels are preferably about 2-20 µm in depth for DNA or polynucleotide analysis, more typically about 10 µm. The detection region in preferred embodiments has a volume of between about 1 pl and about 1 nl. A typical 1 Kbp DNA fragment takes about 10 seconds to diffuse 10 µm, e.g. from the top of a treatment channel to the hybridization probes fixed to the bottom of the channel (e.g. on a glass substrate). In a cell analysis device the channels are preferably between about 1 and 500 microns in width and between about 1 and 500 microns in depth, and the detection region has a volume of between about 1 fl and 100 nl. The channels may be of any dimensions suitable to accommodate the largest dimension of the molecules, particle, viruses, cells or the like to be analyzed.

Manifolds. A device which contains a plurality of analysis units may further include a plurality of manifolds, the number of such manifolds typically being equal to the number of branch channels in one analysis unit, to facilitate collection of molecules from corresponding branch channels of the different analysis units.

Flow of Molecules. In one embodiment, the molecules are directed or sorted by electroosmotic force. A pair of electrodes apply an electric field or gradient across the discrimination region that is effective to move the flow of molecules through the device. In a sorting embodiment the electrodes can be switched to direct a particular molecule into a selected branch channel based on the amount of reporter signal detected from that molecule.

In another embodiment, a flow of molecules is maintained through the device via a pump or pressure differential, and a valve structure can be used at the branch point effective to permit each molecule to enter only one selected branch channel. Alternatively, a valve can be placed in one or more channels downstream of the branch point to allow or curtail flow through each channel. In a related embodiment, pressure can be adjusted at the outlet of each branch channel effective to allow or curtail flow through the channel. Pump and valve arrangements are preferred, such as those disclosed in Ser. No. 60/186,856 filed Mar. 3, 2000 entitled "Microfabricated Elastomeric Valve and Pump Systems".

Microvalves acting in concert to form a pump are preferred for circulating a fluid in a closed loop of the invention. For example, three or more valves in series comprise a peristaltic pump when actuated in an appropriate sequence. Electroosmotic and electrophoretic drives may be less suitable or inoperable in certain applications, for example due to issues of electrical charge.

In preferred polynucleotide sorting embodiments, the concentration of polynucleotides in the solution is between about 10 fM and about 1 nM and the detection region volume is between about 1 fl and about 1 pl. The molecules can be diverted, for example, by transient application of an electric field effective to bias (i) a molecule having the selected property, such as size (e.g., between about 100 bp and about 10 mb) to enter one branch channel, and (ii) a molecule not having the selected property to enter another branch channel. Alternatively, molecules can be directed into a selected channel, based on a detectable property, by temporarily blocking the flow in other channels, such that the continuous stream of solution carries the molecule having the selected property into the selected channel. Pumps and valves may also be used to divert flow, and carry molecules into one or another channels, and mechanical switches may also be used. These methods can also be used in combination, and likewise molecules can be diverted based on whether they have a selected property or size, or do not have that property or size, or exceed or do not exceed a selected threshold measurement.

Optical Detection. Preferably the molecules are optically detectable when passing through the detection region. For example the molecules may be labeled with a reporter, for example a fluorescent reporter. The optically detectable signal can be measured, and generally is proportional to or is a function of a characteristic of the molecules, such as size, molecular weight, or affinity for a predetermined probe. A fluorescent reporter, generating a quantitative optical signal can be used. Fluorescent reporters are known, and can be associated with molecules such as polynucleotides using known techniques. Intercalating dyes, incorporation of fluorescent-labeled single nucleotides, DNA beacons or other well-established detection schemes can be used to determine the final diagnostic results. Suitable fluorescent intercalating dyes include YOYO-1, TOTO-1 and PicoGreen from Molecular Probes, Eugene, Oreg.

In a preferred molecular fingerprinting embodiment, the reporter label is a fluorescently-labeled single nucleotides, such as fluorescein-dNTP, rhodamine-dNTP, Cy3-dNTP, Cy5-dNTP, where dNTP represents dATP, dTFP, dUTP or dCTP. The reporter can also be chemically-modified single nucleotides, such as biotin-dNTP. Alternatively, chemicals can be used that will react with an attached functional group such as biotin.

Sorting Molecules. In another aspect, the invention includes a method of isolating molecules, polynucleotides, proteins, viruses, particles, beads, cells, etc., for example polynucleotides having a selected size. The method includes: a) flowing a stream of solution containing reporter-labeled polynucleotides through a channel comprising a detection region having a selected volume, where the concentration of the molecules in the solution is such that the molecules pass through the detection region one-by-one, c) determining the size of each molecule as it passes through the detection region by measuring the level of the reporter, in the stream, and (d) diverting (i) molecules having the selected size into a first branch channel, and (ii) molecules not having the selected size into a second branch channel. Polynucleotides diverted into any channel can be collected as desired.

Synchronization. In each embodiment where molecules are diverted, as opposed to being measured only, the molecules are detected one-by-one within a detection region, and are diverted one-by-one into the appropriate channels, by coordinating or synchronizing the diversion of flow with the detection step and with the flow entering the detection, as described for example in more detail below. In certain embodiments the flow rate may be adjusted, for example delayed, to maintain efficient detection and switching, and as described below the flow may in some cases be temporarily reversed to improve accuracy.

Sizing Molecules. In yet another aspect, the invention includes a method of sizing polynucleotides in solution. This method includes: a) flowing a continuous stream of solution containing reporter-labeled polynucleotides through a microfabricated channel comprising a detection region having a selected volume, where the concentration of the molecules in the solution is such that most molecules pass through the detection region one by one, and b) determining the size of each molecule as it passes through the detection region by measuring the level of the reporter.

Multiparameter and High Throughput Embodiments. In addition to analyzing or sorting fluorescent and non-fluorescent nucleotide fragments, the invention can also provide multiparameter analysis. For example, sizing or sorting can be done according to a window or threshold value, meaning that molecules (e.g. polynucleotides) are selected based on the presence of a signal above or below a certain value or threshold. There can also be several points of analysis on the same chip for multiple time course measurements.

Mixing Embodiments. Besides analyzing and/or sorting molecules and particles in a sample, the microfluidic devices of this invention are also useful for mixing two or more different fluids. For example, the devices of the invention can be used to mix fluids containing different molecules; such as different solvent molecules, molecules of a sample and/or reagent, or for mixing molecules of a sample and a detection probe. In preferred embodiments, the devices are used to mix molecules such as nucleic acid molecules, polypeptide molecules (e.g., proteins), antibody molecules, or molecules of a particular reagent or ligand. In other preferred embodiments the devices can be used to mix suspensions of different particles such as cells or virions.

The invention therefore provides uses of these microfluidic devices for mixing two or more different fluids and, in particular, provides methods for mixing different fluids using a microfluidic device that has: (i) a loop channel, (ii) at least one service channel in fluid communication with the loop channel, (iii) a microvalve separating the loop channel from the service channel, and (iv) a pump associated with the loop channel. The methods involve introducing the different fluids to the microfluidic device so that each different fluid is loaded into the loop channel, and activating the pump associated with the loop channel so that the different fluids are effectively mixed.

As used to describe the present invention, two or more fluids in a microfluidic device or channel are said to be "effectively mixed" when the channel contains a homologous or substantially homologous combination of the molecules and/or particles from the different fluids. Thus, in preferred embodiments two or more different fluids in a microfluidic channel may be effectively mixed if the channel contains a combination of molecules and/or particles from the fluids that is, e.g., at least 50% homologous, more preferably at least 60% homologous, 70% homologous, 75%, 80%, 85%, or 90% homologous. However, in some embodiments homologies as low as 20% or 25% will be adequate. In other preferred embodiments, the two or more fluids in a microfluidic device or channel are mixed when the combination of molecules is more than 90% homologous, more preferably 95% homologous and still more preferably at least 99% homologous. Indeed, in particularly preferred embodiments of the invention, two or more fluids in a microfluidic device or channel are said to be mixed when the combination of molecules and/or particles from the different fluids is 100% homologous. Thus, when two or more fluids are mixed in a microfluidic device of the invention they preferably are no longer distinguishable as individual fluids and are, to a user, a single, homologous fluid of molecules and/or particles.

Using the microfluidic devices provided in this invention, molecules and/or particles in fluids may be mixed in mixing times that are only a few minutes, as opposed to mixing by simple diffusion which may take a matter of hours. Thus, in preferred embodiments of the invention fluids are mixed in a microfluidic loop by activating the pump for less than one hour and more preferably for less than 30 minutes. In typical, preferred embodiments the pump need only be activated for 15 minutes or less (e.g., for 10, 5, 4, 3, 2 or 1 minute). In certain embodiments, the mixing time may be as short as a few seconds (for example, between 60 and 30 seconds, or less than 30 seconds). For example, as explained, supra, in the Examples, two fluids may be effectively mixed in a microfluidic loop if the center of fluid front (i.e., the boundary between the different fluids) makes only half of one revolution through the loop. Typically, however, the fluid front will make multiple revolutions around the loop (e.g., at least 1, at least 2, at least 5, at least 10, at least 50 or at least 100).

Using methods that are similar to the mixing methods described above, microfluidic devices of the invention may also be used to facilitate binding of a sample to target. Accordingly, the invention provides such uses for the microfluidic devices described here and, in particular, provides methods for binding a sample to a target using a microfluidic device which has: (i) a loop channel, (ii) at least one service channel in fluid communication with the loop channel, (iii) a microvalve separating the loop channel from the service channel, and (iv) a pump associated with the loop channel. In such methods, molecules of the target are preferably disposed within the loop channel of the microfluidic device. The methods therefore simply comprise introducing a fluid containing the sample to the microfluidic device, and activating the pump so that the fluid throughs through the loop channel. The particles or molecules in the sample therefore travel and bind more rapidly to the target molecules than by simple diffusion so that in general, the pump need only be activated for a matter of minutes (e.g., fewer than 60 minutes, more preferably fewer than 30, 20, 15, 10, 5, 4, 3, 2 or 1 minutes). In fact, in some instances the pump may even be activated for less than one minute (e.g., for between 60-30 seconds, or for less than 30 seconds). The sample may be, e.g., a suspension of particles such as cells or virions, or that sample may be a solution of molecules. For example, in a preferred embodiment the sample is a sample of nucleic acid molecules that includes (or is suspected to include) a nucleotide sequence of interest to a user. In such a preferred embodiment, the target molecules are typically polynucleotide probes (e.g., having a sequence complementary to the nucleotide sequence of interest). In still other embodiments, the sample may comprise polypeptide molecules and the target may comprise antibody probe molecules or, alternatively, the sample may comprise a particular ligand or reagent, and the target molecules may comprise a polypeptide or protein probe (e.g., that binds to and/or reacts with the sample).

Thus, the invention provides for the rapid and accurate determination of the "profile" of a polynucleotide in high resolution using minimal amounts of material in these simple and inexpensive microfabricated devices. The methods and devices of the invention can replace or be used in combination with conventional gel based approaches.

The devices and methods of the invention can also be used to test a sample against multiple targets. In these embodiments an array of probes, corresponding to a different targets, is fixed to one or more channels in one or more detection regions of the device. Preferably, probes are fixed to a glass substrate or coverslip that seals the detection channels while exposing them to optical interrogation or examination, e.g. with a microscope. Sample is passed by the probes, and matching molecules in the sample (if any) respond, e.g. by reacting, associating or binding with the corresponding probes in a detectable or measurable way. In a preferred embodiment the sample contains DNA (e.g. a blood sample), which may be denatured or fragmented, and the probes contain DNA that is characteristic of particular disease conditions, or has some other characteristic of interest, e.g. forensic. Any suitable set of reagents or probes can be used to provide a battery or array of tests upon a sample. Thus, the devices and methods of the invention also provide high throughput screening of samples for any purpose, including diagnostics and drug discovery.

In one embodiment, probes are fixed in discrete locations on a glass substrate in a pattern corresponding to the path of an adjacent treatment channel, or loop, which can comprise any closed path, i.e. it can be temporarily isolated from the rest of the chip, for example by closing valves in any channels which lead into or out of the loop. Using the microvalves and peristaltic pump action described herein, sample can be introduced to the loop, containing probes, and can be recirculated past the probes as desired, to rapidly and repeatedly test for the presence or absence of multiple targets in the sample.

A typical target loop of the invention, e.g. for DNA assays, has a circular path, although any path which can be closed is encompassed by the invention. The length of the loop (or the diameter of a circular embodiment) depends on the number of diagnostic spots (e.g. hybridization spots) in the loop, the size of each spot, and the distance between each spot. For example, a loop channel that is 100 μm wide can be provided with diagnostic spots that are about 100 μm wide and 100 μm long (or about 100 μm in diameter), with about 100 μm between each spot. Each spot can be provided with a probe, for example a DNA fragment or an antibody immobilized on a substrate and presented to sample that is circulated in the loop. The spots can be observed or imaged as described herein, to detect or measure the interaction between material in the sample and material at the diagnostic spot.

In another preferred embodiment a target loop may have some other geometry, for example the geometry illustrated in FIG. 20. In a particularly preferred embodiment a microfluidic device comprises an array of target loops having a size and dimensions comparable with the wells of a standard microtiter plate. The target loops may then be assembled over the separate wells of the microtiter plate. For example, the invention provides microfluidic devices having an array of 96 target loops (e.g., that is compatible with a 96-well microtiter plate). The invention also provides microfluidic devices having arrays of 384 target loops (e.g., that are compatible with 384-well microtiter plates). The invention still further provides microfluidic devices having arrays of 1536 target loops (e.g., that are compatible with 1.536-well microtiter plates).

In preferred embodiments the loop channel is about 2-20 μm deep, preferably about 10 μm deep, and is from about 10-200 μm wide, preferably from about 50-100 μm wide, and more preferably about 100 μm wide. The target loop is fed by a loop inlet and is drained by a loop outlet, each of which can be independently opened and closed, e.g. by appropriately positioned microvalves. The target loop or target treatment channel is intersected by at least three air or control channels on a facing layer of the device. Preferably, the control channels intersect the circular loop in a radial fashion, and may terminate inside a region defined by the loop. Each intersection between the loop and a control channel forms a microvalve. Varying the pressure (e.g. air pressure) in at least three intersecting control channels creates three microvalves which open and close in response to pressure changes, causing a peristaltic flow around the loop. For example, expansion of the control channel in response to pressure can pinch, constricting or block the loop channel at the intersection point. Relaxation of the control channel in response to a pressure drop opens the restricted or closed loop channel. Cycles of contraction and expansion cause temporary closing and opening of the loop channel, which sets up a flow around the loop, which is preferably closed during testing for matching probes. In this system, sample molecules are circulated past the probes in a closed loop, ensuring rapid and complete exposure of the sample to a plurality of probes, for quick, accurate, and inexpensive analysis using very small amounts of sample, probes, reagents, etc.

4. BRIEF DESCRIPTION OF THE DRAWINGS

Figure 11A:
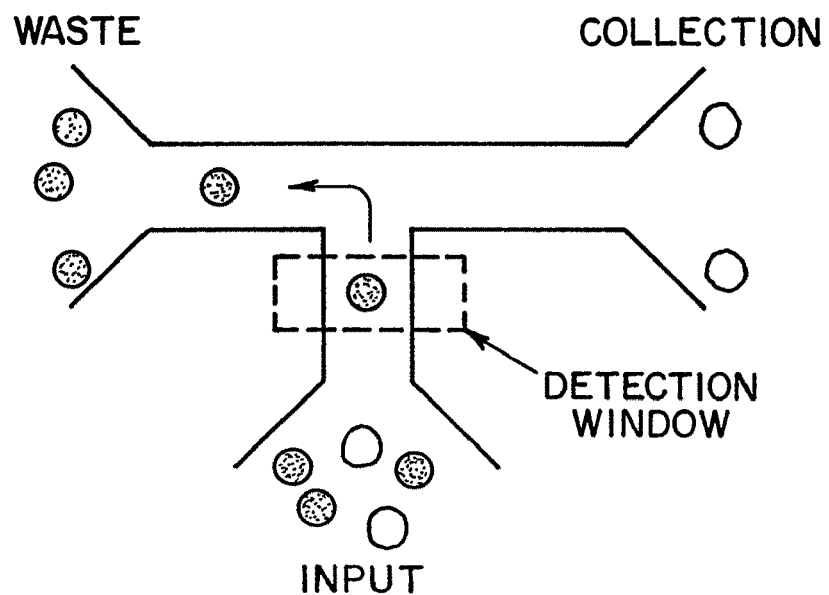
Figure 11B:
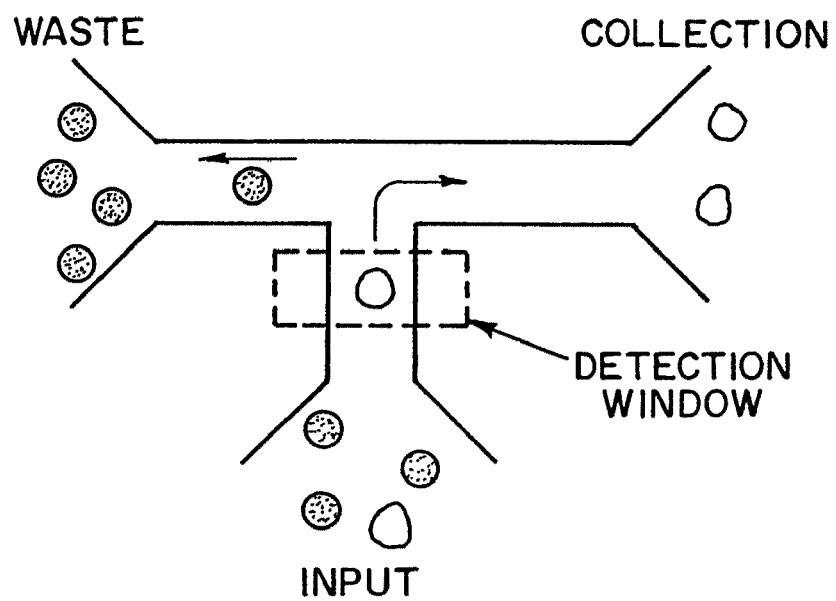

FIGS. 11A and B show a sorting scheme according to the invention, in diagrammatic form.

Figure 12A:
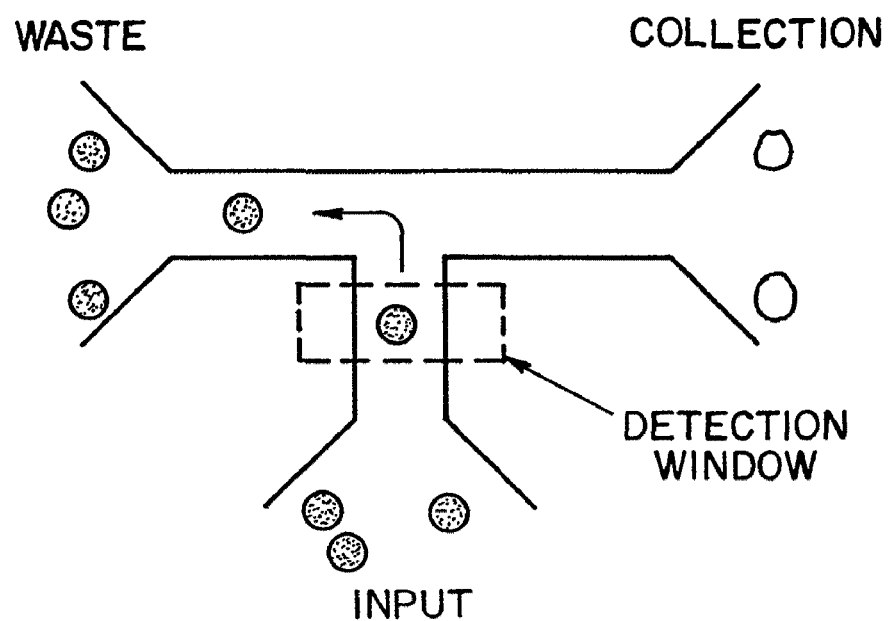
Figure 12B:
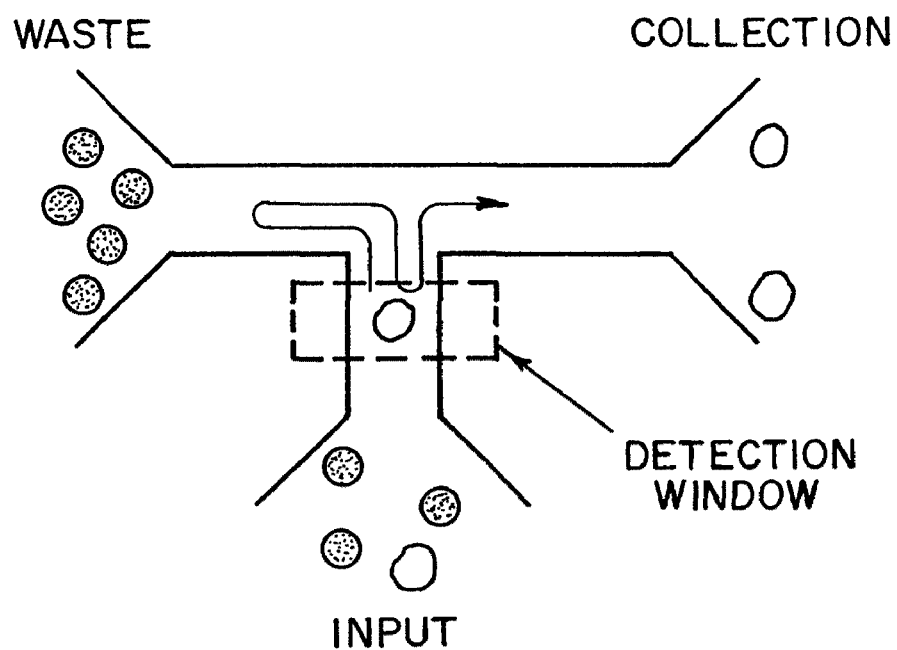

FIGS. 12A and B show a reversible sorting scheme according to the invention.

Figure 13A:
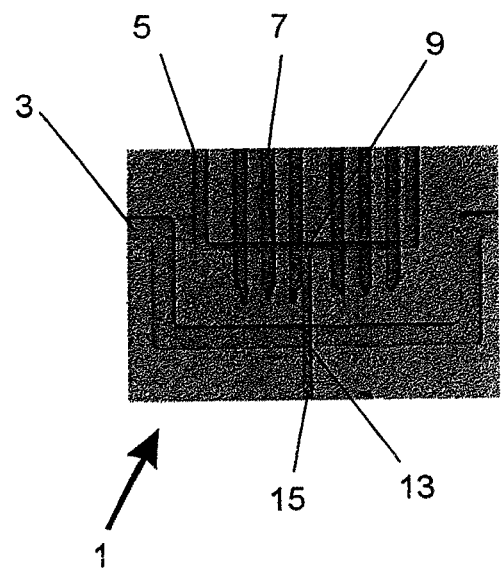
Figure 13B:
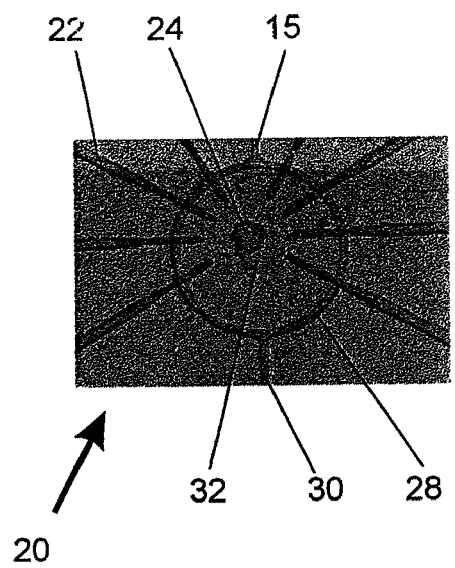

FIGS. 13A and 13B are micrographs of an exemplary chip according to the invention, e.g. for DNA diagnosis. FIG. 13A shows input mixing T-channels 5 (50 µm wide×10 µm deep) on a lower layer and six corresponding air channels 7 and control microvalves 17 on an upper layer. A wider (100-µm) air channel 3 is used to close the inlet 15 at a valve 13 when the peristaltic pump at the ring (FIG. 13B) starts operating, e.g. for mixing or hybridization. FIG. 13B shows a center ring loop 28 for mixing and/or DNA hybridization. Any three of the finger channels 22 (on the top air-channel layer) form a peristaltic pump with corresponding valves 32. The loop channels are 50 µm wide×10 µm deep. The channel 15 at the bottom of FIG. 13A connects to the channel 15 top of FIG. 13B. The whole device is 1" by 11" in size.

Figure 14:
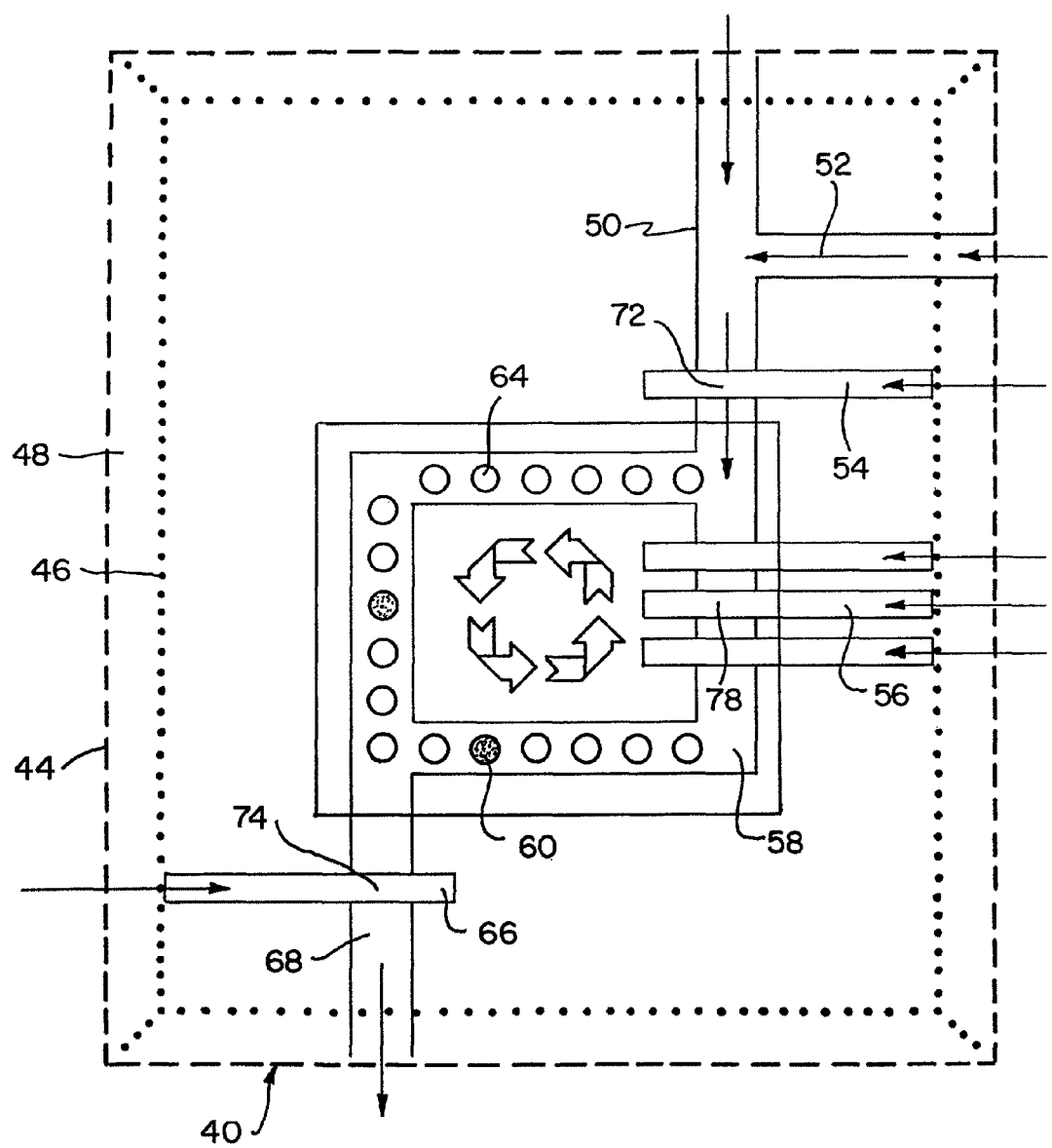

FIG. 14 is a schematic diagram of a device of the invention, showing a central mixing and/or a detection loop (e.g. for hybridization) actuated by a peristaltic pump formed of microvalves where air channels intersect underlying fluid channels.

Figure 15:
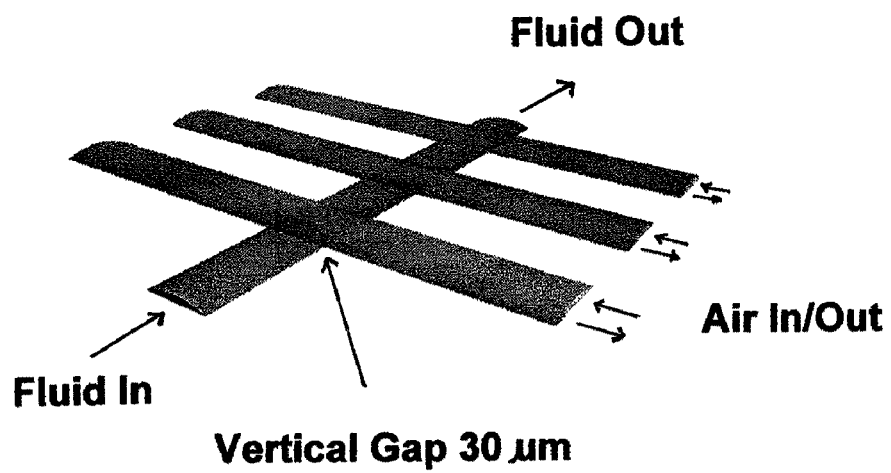

FIG. 15 is a schematic depiction of a peristaltic pump, formed by three air channels intersecting an underlying fluid channels, with a microvalve at each intersection.

Figure 16A:
Figure 16B:
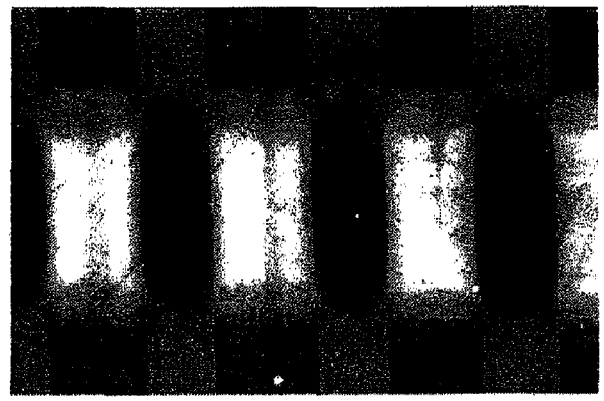
Figure 16C:
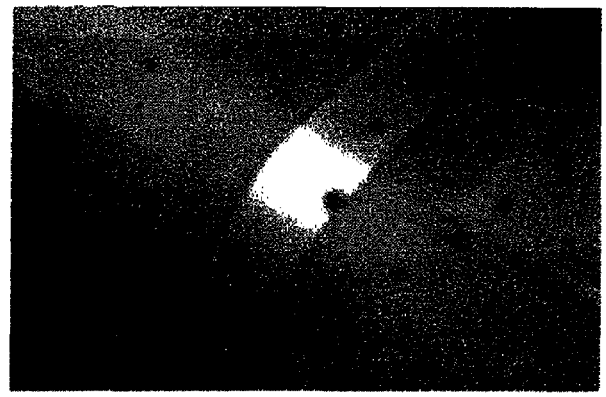

FIGS. 16A-C show images of chemically patterned cover slips, e.g. for use in immobilizing probes within a detection loop of the invention. In FIG. 16A, a line pattern is obtained by flowing avidin-fluorescein conjugates vertically on a biotinylated cover slip. In FIG. 16B a checkerboard pattern obtained by flowing strepta-vidin horizontally (200 µm) and biotin-fluorescein conjugates vertically (100 µm). FIG. 16C shows DNA patterned on a silanized slide. The DNA lights up when the fluorescent dye PicoGreen is flowing in the central ring loop. From top-left to bottom-right in the figure shows DNA with a slight auto-fluorescence. From top-right to bottom-left shows part of the central ring of the diagnosis chip under a dark-field illumination.

Figure 17:
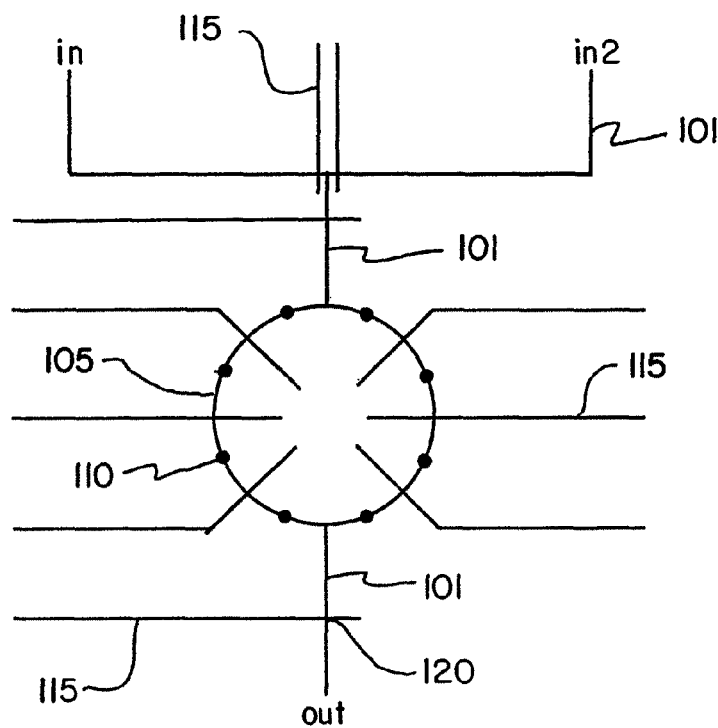

FIG. 17 is a schematic diagram of a device of FIGS. 13A and 13B, showing a T-inlet and a circular mixing and detection loop with cooperating control channels forming microvalves and a peristaltic pump.

Figure 18A:
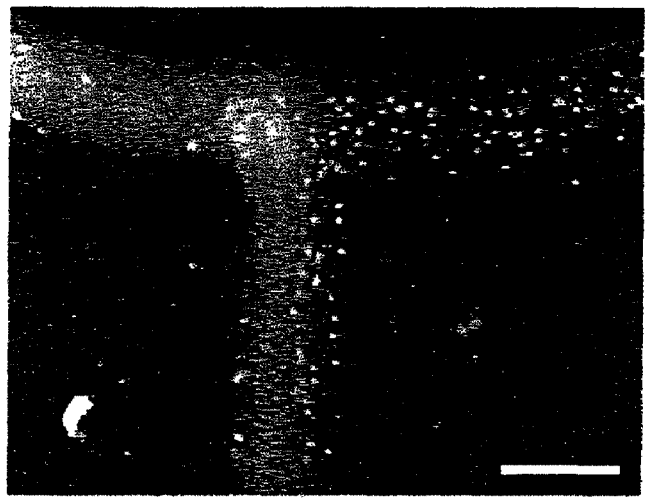
Figure 18B:
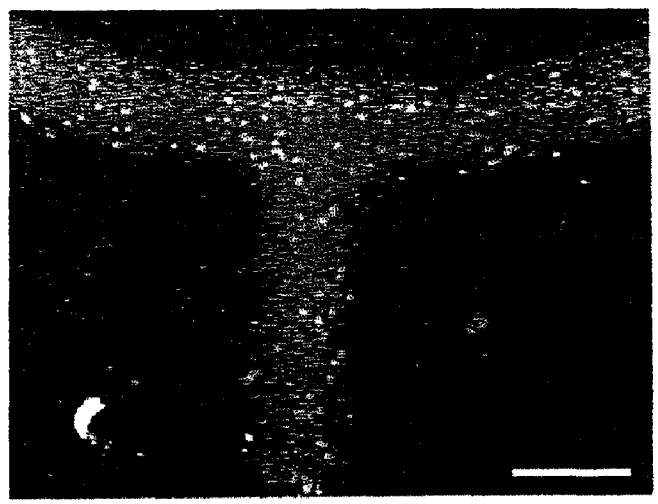

FIG. 18 shows in-line mixing by rotary pumping in a closed loop channel of the invention. In FIG. 18A there is no pumping. Buffer containing fluorescent beads (left) and buffer containing fluorescent dye (right) do not mix with each other because of a laminar flow profile. FIG. 18B shows active rotary pumping. The peristaltic pump at the ring, where the liquids come from, is turned on. Both dye and beads are well mixed at the output channel. Each inset shows an illustration of the corresponding distribution of beads and fluorescent dye in the fluidic channels.

Figure 19:

FIG. 19 is a snapshot of a running biotin/avidin diagnosis chip, where two biotin pads at the central ring are shown. This picture was taken 4 minutes after the peristaltic pump started. Fluorescent NeutrAvidin beads have bound to the biotin pads. Thin stripes are beads which were still moving in the ring loop while this picture was taken.

Figure 20:
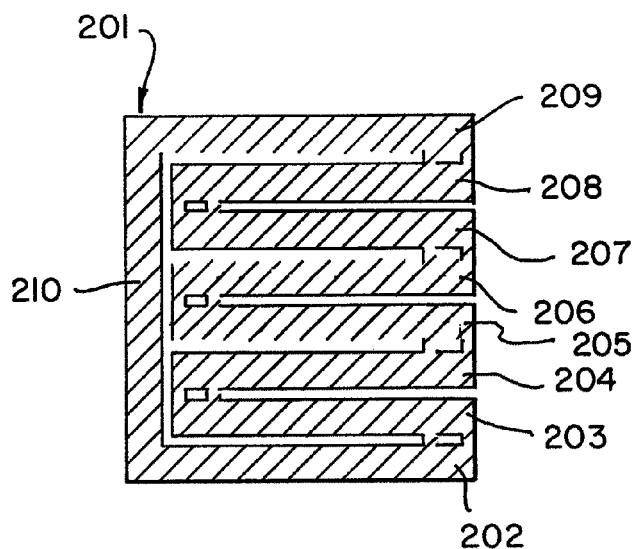

FIG. 20 is a schematic diagram of an exemplary loop channel (e.g., for hybridization) geometry which may be used in a microfluidic device.

Figure 21A:
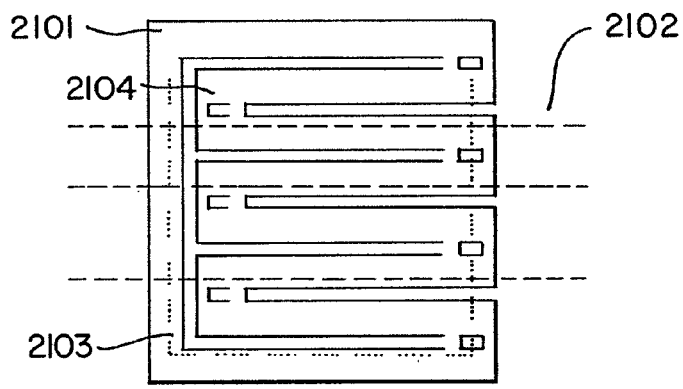
Figure 21B:
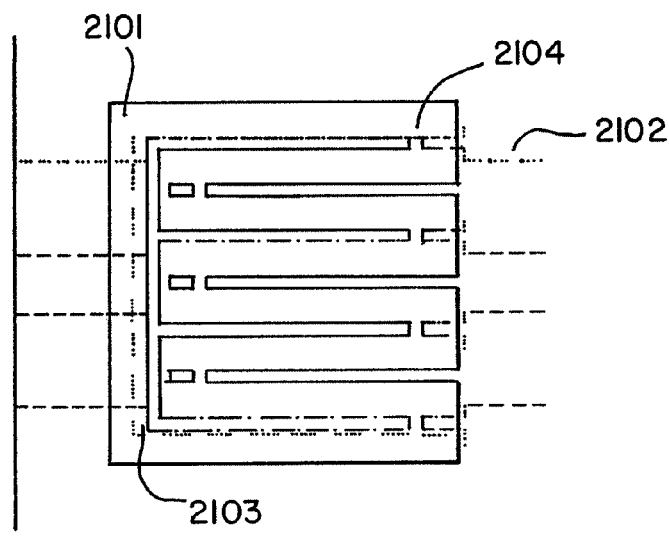

FIGS. 21A-B are schematic diagrams of a mixing or detection loop (e.g., for hybridization) actuated by peristaltic pumps which can be used in a microfluidic device having an array of such loops.

Figures 22A, 22B:
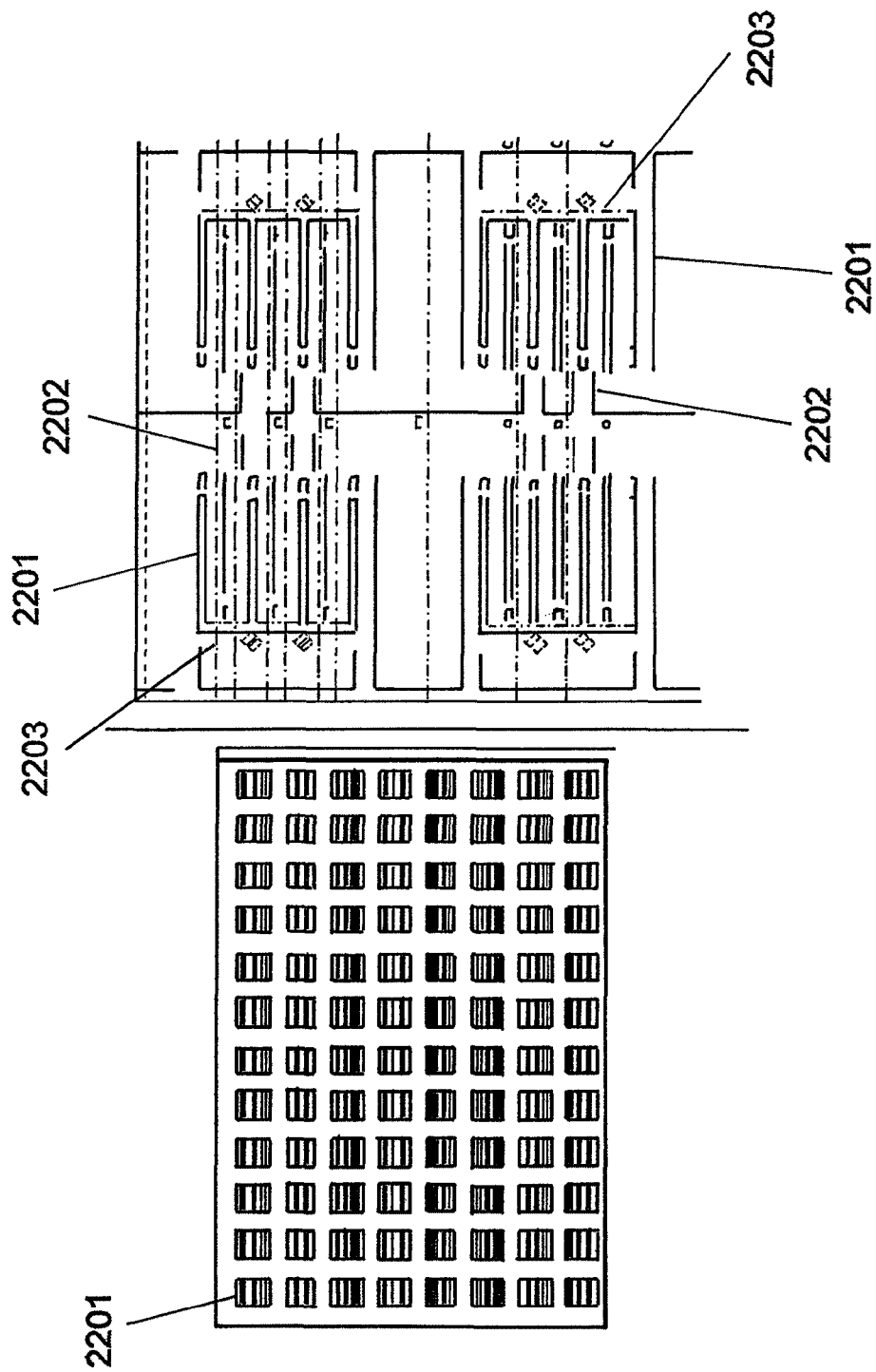

FIGS. 22A-B are schematic diagrams of an exemplary microfluidic device having an arrayed plurality of the mixing or detection loops illustrated in FIGS. 21A-B.

Figure 23A:
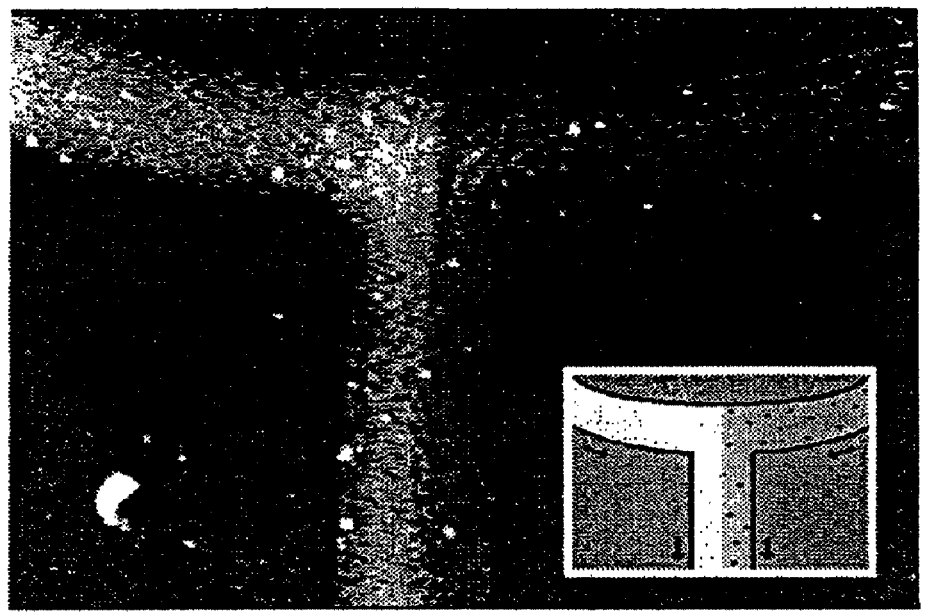
Figure 23B:
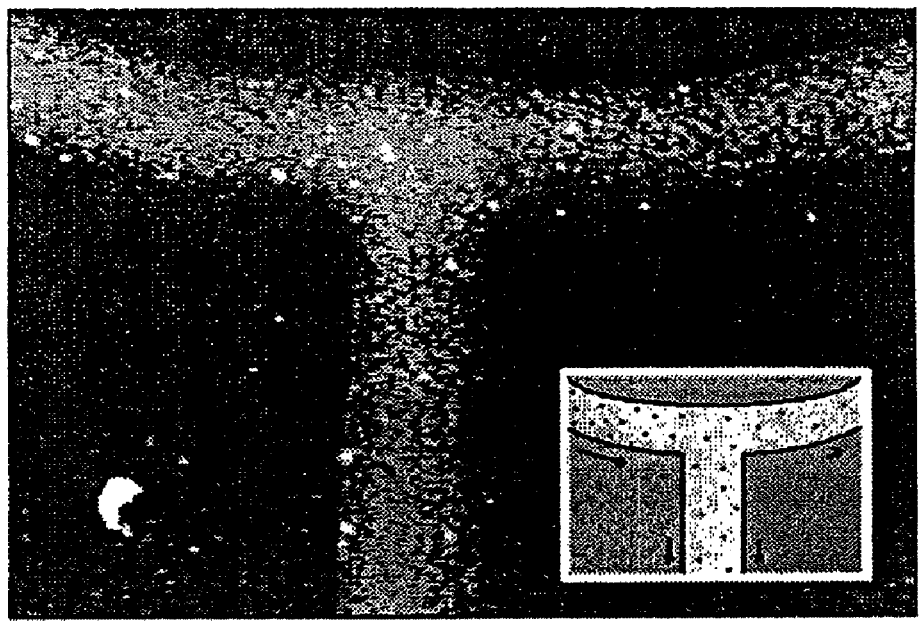
Figure 23C:
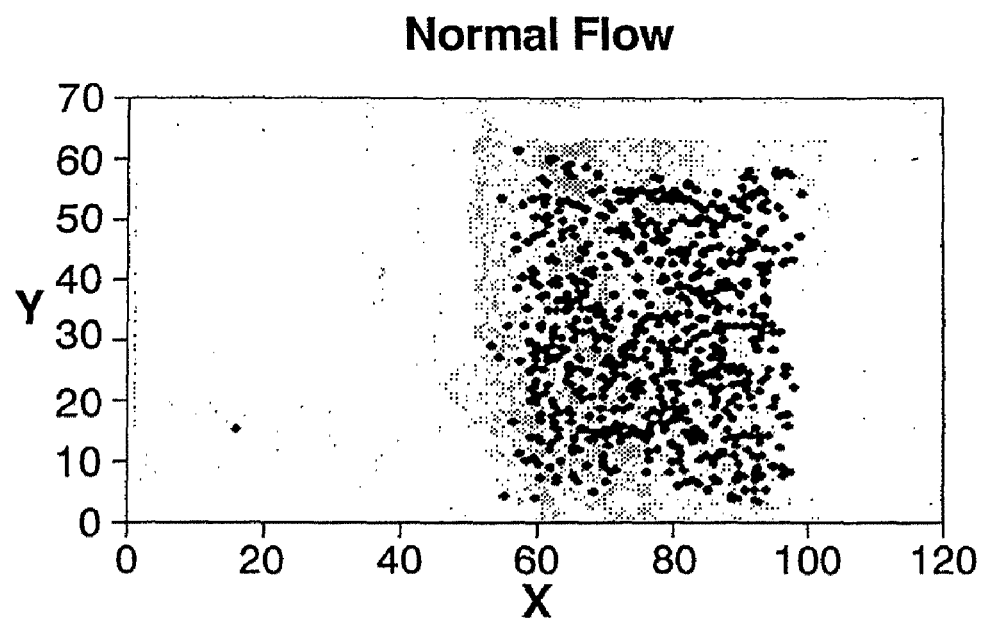
Figure 23D:
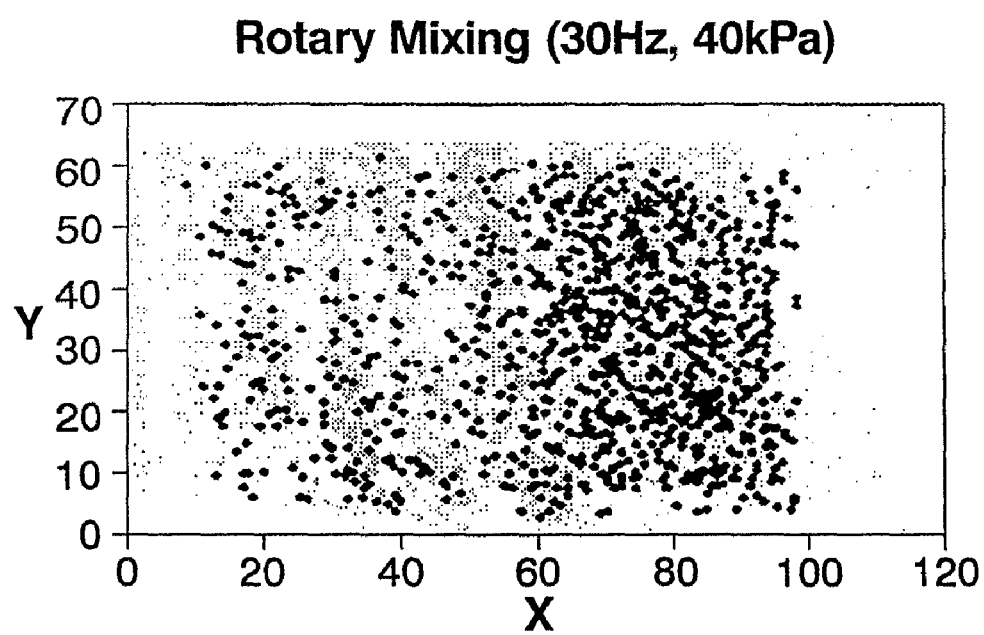
Figure 23E:
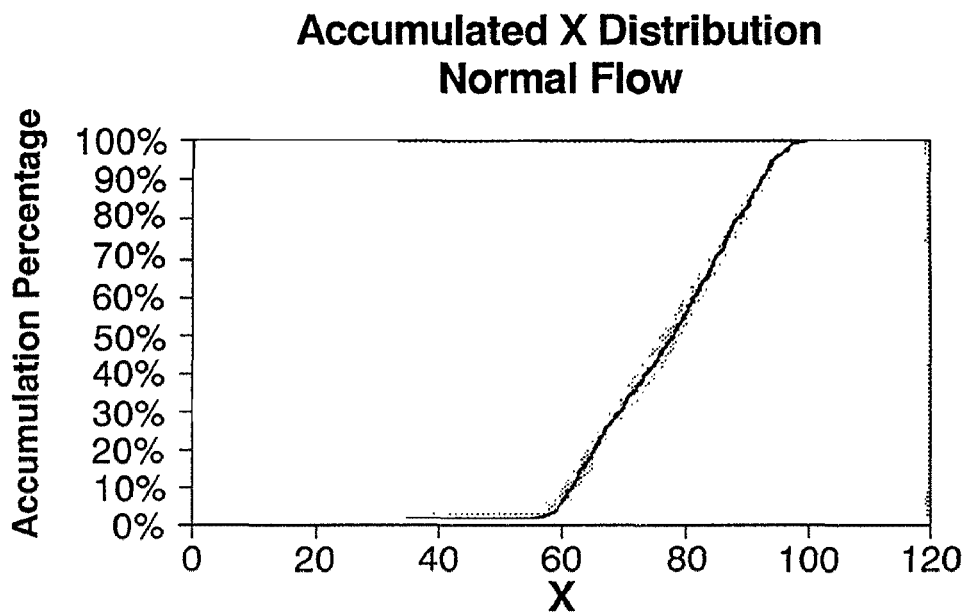
Figure 23F:
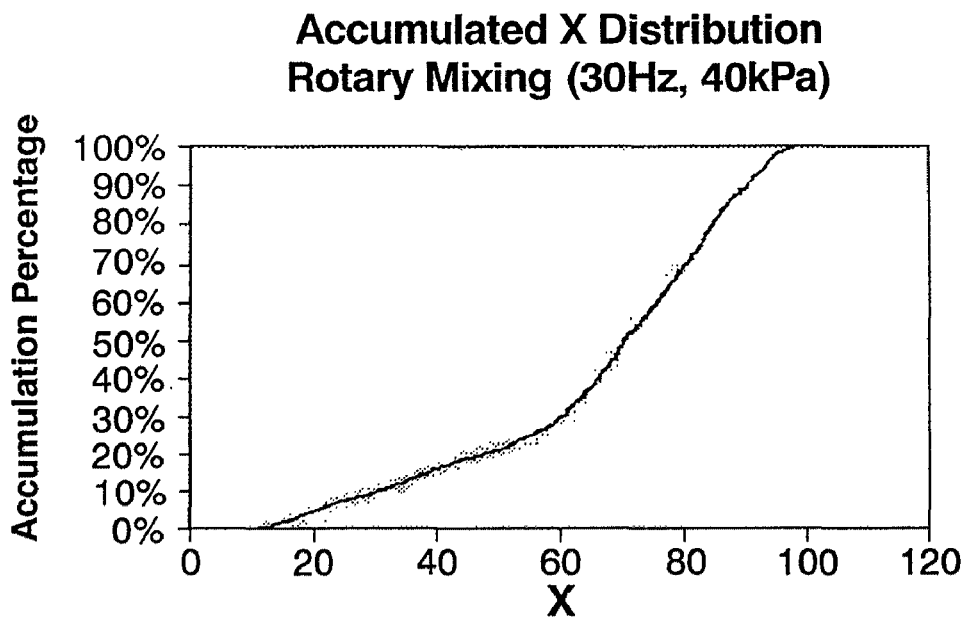

FIGS. 23A-F shows images (FIGS. 23A-B) and data (FIGS. 23C-F) from continuous flow mixing by rotary pumping in an open loop channel of the invention. In FIG. 23A there is no pumping through the loop. FIGS. 23C and 23E show the distribution of the fluorescent dye solution and beads in detail when there is no rotary pumping in the loop. Buffer containing fluorescent beads (left) and fluorescent dye (right) do not mix with each other because of a laminar flow profile. FIG. 23B shows continuous-flow mixing in the loop when there is active rotary pumping. FIGS. 23D and 23F show the distribution of the fluorescent dye solution and beads in detail when there is active rotary pumping in the loop. Rotary mixing helped about 25% of the fluorescent beads traverse into the other side of the flow stream.

Figure 24:
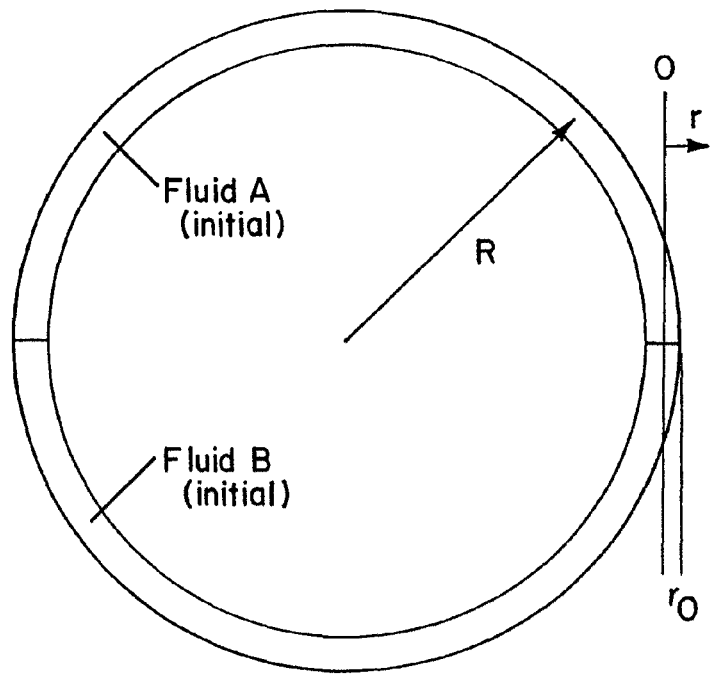

FIG. 24 is a simplified schematic diagram for an exemplary loop channel that has a channel width of $2r_0$ (i.e., a radius equal to $r_0$) and forms a circular loop of radius R. The loop channel is used, in this example, to mix to separate fluid indicated as fluid A and B, respectively.

5. DETAILED DESCRIPTION OF THE INVENTION

5.1. Definitions

The terms used in this specification generally have their ordinary meanings in the art, within the context of the invention, and in the specific context where each term is used. For example, conventional techniques of molecular biology, microbiology and recombinant DNA techniques may be employed in accordance with the present invention. Such techniques and the meanings of terms associated therewith are explained fully in the literature. See, for example, Sambrook, Fitsch & Maniatis, *Molecular Cloning. A Laboratory Manual*, Second Edition (1989) Cold Spring Harbor Laboratory Press, Cold Spring Harbor, N.Y. (referred to herein as "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* (B. D. Hames & S. J. Higgins, eds. 1984); *Animal Cell Culture* (R. I. Freshney, ed. 1986); *Immobilized Cells and Enzymes* (IRL Press, 1986); B. E. Perbal, *A Practical Guide to Molecular Cloning* (1984); F. M. Ausubel et al. (eds.), *Current Protocols in Molecular Biology*, John Wiley & Sons, Inc. (1994). See also, *PCR Protocols: A Guide to Methods and Applications*, Innis et al., eds., Academic Press, Inc., New York (1990); Saiki et al., *Science* 1988, 239:487; and *PCR Technology: Principles and Applications for DNA Amplification*, H. Erlich, Ed., Stockton Press.

Certain terms that are used to describe the invention are discussed below, or elsewhere in the specification, to provide additional guidance to the practitioner in describing the devices and methods of the invention and how to make and use them. For convenience, certain terms are highlighted, for example using italics and/or quotation marks. The use of highlighting has no influence on the scope and meaning of a term; the scope and meaning of a term is the same, in the same context, whether or not it is highlighted. It will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only, and in no way limits the scope and meaning of the invention or of any exemplified term. Likewise, the invention is not limited to the preferred embodiments.

As used herein, "about" or "approximately" shall generally mean within 20 percent, preferably within 10 percent, and more preferably within 5 percent of a given value or range. Numerical quantities given herein are approximate, meaning that the term "about" or "approximately" can be inferred if not expressly stated.

The term "molecule" means any distinct or distinguishable structural unit of matter comprising one or more atoms, and includes for example polypeptides and polynucleotides.

The term "polymer" means any substance or compound that is composed of two or more building blocks ('mers') that are repetitively linked to each other. For example, a "dimer" is a compound in which two building blocks have been joined together.

The term "polynucleotide" as used herein refers to a polymeric molecule having a backbone that supports bases capable of hydrogen bonding to typical polynucleotides, where the polymer backbone presents the bases in a manner to permit such hydrogen bonding in a sequence specific fashion between the polymeric molecule and a typical polynucleotide (e.g., single-stranded DNA). Such bases are typically inosine, adenosine, guanosine, cytosine, uracil and thymidine. Polymeric molecules include double and single stranded RNA and DNA, and backbone modifications thereof, for example, methylphosphonate linkages.

Thus, a "polynucleotide" or "nucleotide sequence" is a series of nucleotide bases (also called "nucleotides") generally in DNA and RNA, and means any chain of two or more nucleotides. A nucleotide sequence typically carries genetic information, including the information used by cellular machinery to make proteins and enzymes. These terms include double or single stranded genomic and cDNA, RNA, any synthetic and genetically manipulated polynucleotide, and both sense and anti-sense polynucleotide (although only sense stands are being represented herein). This includes single- and double-stranded molecules, i.e., DNA-DNA, DNA-RNA and RNA-RNA hybrids, as well as "protein nucleic acids" (PNA) formed by conjugating bases to an amino acid backbone This also includes nucleic acids containing modified bases, for example thio-uracil, thio-guanine and fluoro-uracil.

The polynucleotides herein may be flanked by natural regulatory sequences, or may be associated with heterologous sequences, including promoters, enhancers, response elements, signal sequences, polyadenylation sequences, introns, 5'- and 3'-non-coding regions, and the like. The nucleic acids may also be modified by many means known in the art. Non-limiting examples of such modifications include methylation, "caps", substitution of one or more of the naturally occurring nucleotides with an analog, and internucleotide modifications such as, for example, those with uncharged linkages (e.g., methyl phosphonates, phosphotriesters, phosphoroamidates, carbamates, etc.) and with charged linkages (e.g., phosphorothioates, phosphorodithioates, etc.). Polynucleotides may contain one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. The polynucleotides may be derivatized by formation of a methyl or ethyl phosphotriester or an alkyl phosphoramidate linkage. Furthermore, the polynucleotides herein may also be modified with a label capable of providing a detectable signal, either directly or indirectly. Exemplary labels include radioisotopes, fluorescent molecules, biotin, and the like.

"DNA" (deoxyribonucleic acid) means any chain or sequence of the chemical building blocks adenine (A), guanine (G), cytosine (C) and thymine (T), called nucleotide bases, that are linked together on a deoxyribose sugar backbone. DNA can have one strand of nucleotide bases, or two complimentary strands which may form a double helix structure. "RNA" (ribonucleic acid) means any chain or sequence of the chemical building blocks adenine (A), guanine (G), cytosine (C) and uracil (U), called nucleotide bases, that are linked together on a ribose sugar backbone. RNA typically has one strand of nucleotide bases.

A "polypeptide" (one or more peptides) is a chain of chemical building blocks called amino acids that are linked together by chemical bonds called peptide bonds. A protein or polypeptide, including an enzyme, may be "native" or "wild-type", meaning that it occurs in nature; or it may be a "mutant", "variant" or "modified", meaning that it has been made, altered, derived, or is in some way different or changed from a native protein, or from another mutant.

As used herein, "cell" means any cell or cells, as well as viruses or any other particles having a microscopic size, e.g. a size that is similar to that of a biological cell, and includes any prokaryotic or eukaryotic cell, e.g., bacteria, fungi, plant and animal cells. Cells are typically spherical, but can also be elongated, flattened, deformable and asymmetrical, i.e., non-spherical. The size or diameter of a cell typically ranges from about 0.1 to 120 microns, and typically is from about 1 to 50 microns. A cell may be living or dead. Since the microfabricated device of the invention is directed to analyzing or sorting materials having a size similar to protein or polynucleotide molecules or to biological cells (e.g. about 0.1 to 120 microns), any material having a size similar to these molecules and cells can be characterized and sorted using the microfabricated device of the invention. Channels and devices of appropriate size can be fabricated for larger or smaller materials, e.g. for any materials of microscopic size. Thus, the term cell shall further include microscopic beads (such as chromatographic and fluorescent beads), liposomes, emulsions, or any other encapsulating biomaterials and porous materials. Non-limiting examples include latex, glass, or paramagnetic beads; and vesicles such as emulsions and liposomes, and other porous materials such as silica beads. Beads ranging in size from 0.1 micron to 1 mm can also be used, for example in sorting a library of compounds produced by combinatorial chemistry. As used herein, a cell may be charged or uncharged. For example, charged beads may be used to facilitate flow or detection, or as a reporter. Biological cells, living or dead, may be charged for example by using a surfactant, such as SDS (sodium dodecyl sulfate).

A "reporter" is any molecule, or a portion thereof, that is detectable, or measurable, for example, by optical detection. In addition, the reporter associates with a molecule or cell or with a particular marker or characteristic of the molecule or cell, or is itself detectable, to permit identification of the molecule or cell, or the presence or absence of a characteristic of the molecule or cell. In the case of molecules such as polynucleotides such characteristics include size, molecular weight, the presence or absence of particular constituents or moieties (such as particular nucleotide sequences or restrictions sites). The term "label" can be used interchangeably with "reporter". The reporter is typically a dye, fluorescent, ultraviolet, or chemiluminescent agent, chromophore, or radio-label, any of which may be detected with or without some kind of stimulatory event, e.g., fluoresce with or without a reagent. Typical reporters for molecular fingerprinting include without limitation fluorescently-labeled single nucleotides such as fluorescein-dNTP, rhodamine-dNTP, Cy3-dNTP, Cy5-dNTP, where dNTP represents dATP, dTTP, dUTP or dCTP. The reporter can also be chemically-modified single nucleotides, such as biotin-dNTP. Alternatively, chemicals can be used that react with an attached functional group such as biotin.

A "marker" is a characteristic of a molecule or cell that is detectable or is made detectable by a reporter, or which may be coexpressed with a reporter. For molecules, a marker can be particular constituents or moieties, such as restrictions sites or particular nucleic acid sequences in the case of polynucleotides. The marker may be directly or indirectly associated with the reporter or can itself be a reporter. Thus, a marker is generally a distinguishing feature of a molecule, and a reporter is generally an agent which directly or indirectly identifies or permits measurement of a marker. These terms may, however, be used interchangeably.

The term "flow" means any movement of liquid or solid through a device or in a method of the invention, and encompasses without limitation any fluid stream, and any material moving with, within or against the stream, whether or not the material is carried by the stream. For example, the movement of molecules or cells through a device or in a method of the invention, e.g. through channels of a microfluidic chip of the invention, comprises a flow. This is so, according to the invention, whether or not the molecules or cells are carried by a stream of fluid also comprising a flow, or whether the molecules or cells are caused to move by some other direct or indirect force or motivation, and whether or not the nature of any motivating force is known or understood. The application of any force may be used to provide a flow, including without limitation, pressure, capillary action, electroosmosis, electrophoresis, dielectrophoresis, optical tweezers, and combinations thereof, without regard for any particular theory or mechanism of action, so long as molecules or cells are directed for detection, measurement or sorting according to the invention.

An "inlet region" is an area of a microfabricated chip that receives molecules or cells for detection measurement or sorting. The inlet region may contain an inlet channel, a well or reservoir, an opening, and other features which facilitate the entry of molecules or cells into the device. A chip may contain more than one inlet region if desired. The inlet region is in fluid communication with the main channel and is upstream therefrom.

An "outlet region" is an area of a microfabricated chip that collects or dispenses molecules or cells after detection, measurement or sorting. An outlet region is downstream from a discrimination region, and may contain branch channels or outlet channels. A chip may contain more than one outlet region if desired.

An "analysis unit" is a microfabricated substrate, e.g., a microfabricated chip, having at least one inlet region, at least one main channel, at least one detection region and at least one outlet region. Sorting embodiments of the analysis unit include a discrimination region and/or a branch point, e.g. downstream of the detection region, that forms at least two branch channels and two outlet regions. A device of the invention may comprise a plurality of analysis units.

A "main channel" is a channel of the chip of the invention which permits the flow of molecules or cells past a detection region for detection (identification), measurement, or sorting. In a chip designed for sorting, the main channel also comprises a discrimination region. The detection and discrimination regions can be placed or fabricated into the main channel. The main channel is typically in fluid communication with an inlet channel or inlet region, which permit the flow of molecules or cells into the main channel. The main channel is also typically in fluid communication with an outlet region and optionally with branch channels, each of which may have an outlet channel or waste channel. These channels permit the flow of molecules or cells out of the main channel.

In certain embodiments, a "circulation loop" is located within the chip, typically in or communicating with the main channel, in which a fluid (e.g. the flow of a biological sample) is circulated. The circulation loop may comprise a "hybridization loop" or "target loop" in which the flow is directed past a series of targets or probes (e.g. DNA or proteins) that are in or exposed to the loop and its contents. For example, probes may be patterned on the surface of a substrate, e.g. a solid substrate and also called a "probe substrate". The probe substrate typically forms part of a channel, e.g. as a wall, ceiling or floor of a fluid channel, or is exposed to or communicates with a channel, or receives or is exposed to a flow of fluid or sample from a channel. Preferred probe substrates are transparent, e.g. glass. Alternatively, the probe substrate may be an elastomer itself, which may prove advantageous when higher back pressures are used.

The loop may have any shape. The channel or channels comprising a loop may have or cooperate with pumps and/or valves to open and close the loop, and/or to provide or drain contents to and from the loop. In a preferred embodiment, the loop can be isolated or closed from other channels in a microfluidic device. Also in a preferred embodiment, fluid can be circulated in the loop, for example by providing a peristaltic pump comprising three or more microvalves.

A circulation loop may also be referred to as a "detection loop" in embodiments where detection, measurement or analysis occurs in or coincident with all or any part of the loop.

A "detection region" is a location within the chip, typically in or coincident with the main channel (or a portion thereof) and/or in or coincident with a detection loop, where molecules or cells to be identified, characterized, hybridized, measured, analyzed or sorted (etc.), are examined on the basis of a predetermined characteristic. In a preferred embodiment, molecules or cells are examined one at a time. In other preferred embodiments, molecules, cells or samples are examined together, for example in groups, in arrays, in rapid, simultaneous or contemporaneous serial or parallel arrangements, or by affinity chromatography. In one such embodiment, a sample is exposed to probes in detection region, preferably probes having a predetermined pattern within or coincident with a detection region, e.g. a target hybridization or detection loop. Preferably, the molecule or cell characteristic is detected or measured optically, for example, by testing for the presence or amount of a reporter. For example, the detection region is in communication with one or more microscopes, diodes, light stimulating devices, (e.g., lasers), photomultiplier tubes, and processors (e.g., computers and software), and combinations thereof, which cooperate to detect a signal representative of a characteristic, marker, or reporter, and to determine and direct the measurement or the sorting action at the discrimination region. In sorting embodiments, the detection region is in fluid communication with a discrimination region and is at, proximate to, or upstream of the discrimination region.

A "discrimination region" or "branch point" is a junction of a channel where the flow of molecules or cells can change direction to enter one or more other channels, e.g., a branch channel, depending on a signal received in connection with an examination in the detection region. Typically, a discrimination region is monitored and/or under the control of a detection region, and therefore a discrimination region may "correspond" to such detection region. The discrimination region is in communication with and is influenced by one or more sorting techniques or flow control systems, e.g., electric, electro-osmotic, (micro-) valve, etc. A flow control system can employ a variety of sorting techniques to change or direct the flow of molecules or cells into a predetermined branch channel.

A "branch channel" is a channel which is in communication with a discrimination region and a main channel. Typically, a branch channel receives molecules or cells depending on the molecule or cell characteristic of interest as detected by the detection region and sorted at the discrimination region. A branch channel may be in communication with other channels to permit additional sorting. Alternatively, a branch channel may also have an outlet region and/or terminate with a well or reservoir to allow collection or disposal of the molecules or cells.

The term "forward sorting" or flow describes a one-direction flow of molecules or cells, typically from an inlet region (upstream) to an outlet region (downstream), and preferably without a change in direction, e.g., opposing the "forward" flow. Preferably, molecules or cells travel forward in a linear fashion, i.e., in single file. A preferred "forward" sorting algorithm consists of running molecules or cells from the input channel to the waste channel, until a molecule or cell is identified to have an optically detectable signal (e.g. fluorescence) that is above a pre-set threshold, at which point voltages are temporarily changed to electroosmotically divert the molecule or to the collection channel.

The term "reversible sorting" or flow describes a movement or flow that can change, i.e., reverse direction, for example, from a forward direction to an opposing backwards direction. Stated another way, reversible sorting permits a change in the direction of flow from a downstream to an upstream direction. This may be useful for more accurate sorting, for example, by allowing for confirmation of a sorting decision, selection of particular branch channel, or to correct an improperly selected channel.

Different "sorting algorithms" can be implemented in devices of the invention by different programs or protocols, for example under the control of a personal computer. A "sorting algorithm" is any set of steps by which any items are identified, distinguished or separated. As an example, consider a pressure-switched scheme instead of electro-osmotic flow. Electro-osmotic switching is virtually instantaneous and throughput is limited by the highest voltage that can be applied to the sorter (which also affects the run time through ion depletion effects). A pressure switched-scheme does not require high voltages and is more robust for longer runs. However, mechanical compliance in the system is likely to cause the fluid switching speed to become rate-limiting with the "forward" sorting program. Since the fluid is at low Reynolds number and is completely reversible, when trying to separate rare molecules or cells one can implement a sorting algorithm that is not limited by the intrinsic switching speed of the device. The molecules or cells flow at the highest possible static (non-switching) speed from the input to the waste. When an interesting molecule or cell is detected, the flow is stopped. By the time the flow stops, the molecule or cell may be past the junction and part way down the waste channel. The system is then run backwards at a slow (switchable) speed from waste to input, and the molecule or cell is switched to the collection channel when it passes through the detection region. At that point, the molecule or cell is "saved" and the device can be run at high speed in the forward direction again. Similarly, an device of the invention that is used for analysis, without sorting, can be run in reverse to re-read or verify the detection or analysis made for one or more molecules or cells in the detection region. This "reversible" analysis or sorting method is not possible with standard gel electrophoresis technologies (for molecules) nor with conventional FACS machines (for cells). Reversible algorithms are particularly useful for collecting rare molecules or cells or making multiple time course measurements of a molecule or single cell.

A "gene" is a sequence of nucleotides which code for a functional polypeptide. For the purposes of the invention a gene includes an mRNA sequence which may be found in the cell. For example, measuring gene expression levels according to the invention may correspond to measuring mRNA levels. "Genomic sequences" are the total set of genes in a organism. The term "genome" denotes the coding sequences of the total genome.

Polynucleotides are "hybridizable" to each other when at least one strand of one polynucleotide can anneal to another polynucleotide under desired or defined stringency conditions. Stringency of hybridization is determined, e.g., by a) the temperature at which hybridization and/or washing is performed, and b) the ionic strength and polarity (e.g., formamide) of the hybridization and washing solutions, as well as other parameters. Hybridization requires that the two polynucleotides contain substantially complementary sequences; depending on the stringency of hybridization, however, mismatches may be tolerated. Typically, hybridization of two sequences at high stringency (such as, for example, in an aqueous solution of 0.5×SSC at 65° C.) requires that the sequences exhibit some high degree of complementarity over their entire sequence. Conditions of intermediate stringency (such as, for example, an aqueous solution of 2×SSC at 65° C.) and low stringency (such as, for example, an aqueous solution of 2×SSC at 55° C.), require correspondingly less overall complementarity between the hybridizing sequences. (1×SSC is 0.15 M NaCl, 0.015 M Na citrate.) Polynucleotides that "hybridize" to the polynucleotides herein may be of any length. In one embodiment, such polynucleotides are at least 10, preferably at least 15 and most preferably at least 20 nucleotides long. In another embodiment, polynucleotides that hybridizes are of about the same length. In another embodiment, polynucleotides that hybridize include those which anneal under suitable stringency conditions and which encode polypeptides or enzymes having the same function.

5.2. Overview of the Invention

The invention provides devices and methods for the detection of multiple diseases in humans or animals. More particularly, in the microfabricated device according to the invention, detection of the presence of molecules (i.e., polynucleotides, proteins, or antigen/antibody complexes) are correlated to a hybridization signal from an optically-detectable (e.g. fluorescent) reporter associated with the bound molecules. The polynucleotides may also be fragmented, for example using endonucleases, to produce a set of fragments that vary in size. The size distribution of these fragments (e.g. the number of fragments of each size over a range of sizes) may uniquely identify the source of the sample. Some or all of the fragments can be selected to serve as a "fingerprint" of the sample. Further, fragments comprising the fingerprint can be labeled, for example with a reporter molecule such as fluorescent marker, so that the they can be more readily detected, measured or sorted. Universal chips according to the invention can be fabricated not only with DNA but also with other molecules such as RNA, proteins, peptide nucleic acid (PNA) and polyamide molecules (4), to name a few.

Thus, the invention provides rapid and accurate determination of the presence of particular genes correlated to a particular disease using minimal amounts of a sample in simple and inexpensive microfabricated devices. The methods and devices of the invention can replace or be used in combination with conventional gel based approaches.

These measurements can be detected by any suitable means, preferably optical, and can be stored for example in a computer as a representation of the presence or absence of a particular gene or the fragments comprising the fingerprint of that gene. Depending on the strategy for producing fragments which comprise a fingerprint, oligonucleotide probes of known composition and length may be used to "tag" or label the fragments. For example, probes having sequences that are complementary to each of the fragments can be made by combining the fragments with labeled nucleotide bases in the presence of a polymerase, which is an enzyme that assembles a single strand of complementary polynucleotide using another strand (i.e. a fingerprint fragment) as a template. The nucleotide bases used to make these probes may be radioactive, or can be labeled with a fluorescent marker, or with some other readily detectable reporter. The resulting probes can be used to record a fingerprint of the sample, by detecting and measuring the lever of reporter as an indication of size, or by sorting the probes according to size.

Labeled or unlabeled probes can also be used to "fish out" matching polynucleotides from a test sample containing unknown DNA or polynucleotides. Under appropriate hybridizing conditions, probes will bind to matching fragments in a sample. This can provide a way to test for a match, for example when the probes comprising a fingerprint hybridize to complementary fragments in the sample. In a preferred embodiment, probes are immobilized on a substrate that forms part of or is exposed to fluid or treatment channels in a detection region of a microfluidic device, e.g. a target loop having discrete hybridization spots. The loop can be selectively isolated from the microfluidic device, for fluid circulation to expose samples and probes to each other. Circulation is preferably provided by microvavles forming a peristaltic pump.

In one aspect of the invention, polynucleotides, e.g., DNA, can be detected, sized or sorted dynamically in a continuous flow stream of microscopic dimensions based for example on molecular weight, using a microfabricated polynucleotide sorting device. The polynucleotides, suspended in a suitable carrier fluid (e.g., $ddH_2O$ or TE), are introduced into an inlet end of a narrow channel in the sorting device. The molecular weight of each molecule is calculated from the intensity of signal from an optically-detectable reporter incorporated into or associated with the polynucleotide molecule as the molecule passes through a "detection window" or "detection region" in the device.

In a sorter embodiment, molecules having a molecular weight falling within a selected range are diverted into a selected output or "branch" channel of the device. The sorted polynucleotide molecules may be collected from the output channels and used in subsequent manipulations.

According to another aspect of the invention, a device such as described above, but not necessarily including components for sorting the molecules, can be used to measure or quantify the size range of polynucleotides in a sample, and store or feed this information into a processor or computer for subsequent analysis or display, e.g., as a size distribution histogram. Such a device enables the generation of the type of polynucleotide fragment length data now commonly obtained from analytical gels, such as agarose or polyacrylamide gels, or from Southern blot results, in a fraction of the time required for preparation and analysis of gels, and using a substantially smaller amount of sample.

5.2.1. Microfabricated Microfluidic Chip Architecture and Method

A molecular or cell analyzer or sorter according to the invention comprises at least one analysis unit having an inlet region in communication with a main channel, a target loop, e.g. for probe hybridization, a detection region within or coincident with all or a portion of the main channel or target loop, and a detector associated with the detection region. Sorter embodiments also have a discrimination region or branch point in communication with the main channel and with branch channels, and a flow control responsive to a detector. There may be a plurality of detection regions and detectors, working independently or together, to analyze one or more properties of a sample. The branch channels may each lead to an outlet region and to a well or reservoir. The inlet region may also communicate with a well or reservoir. As each molecule or cell passes into the detection region, it is examined for a predetermined characteristic (i.e. using the detector), and a corresponding signal is produced, for example indicating that "yes" the characteristic is present, or "no" it is not. The signal may correspond to a characteristic qualitatively or quantitatively. That is, the amount of the signal can be measured and can correspond to the degree to which a characteristic is present. For example, the strength of the signal may indicate the size of a molecule, or the potency or amount of an enzyme expressed by a cell, or a positive or negative reaction such as binding or hybridization of one molecule with another. In response to the signal, data can be collected and/or a flow control can be activated to divert a molecule or cell into one branch channel or another. Thus, molecules or cells within a discrimination region can be sorted into an appropriate branch channel according to a signal produced by the corresponding examination at a detection region. Optical detection of molecule or cell characteristics is preferred, for example directly or by use of a reporter associated with a characteristic chosen for sorting. However, other detection techniques may also be employed.

A variety of channels for sample flow and mixing can be microfabricated on a single chip and can be positioned at any location on the chip as detection and discrimination or sorting points, e.g., for kinetic studies (24, 26). A plurality of analysis units of the invention may be combined in one device. Microfabrication applied according to the invention eliminates the dead time occurring in conventional gel electrophoresis or flow cytometric kinetic studies, and achieves a better time-resolution. Furthermore, linear arrays of channels on a single chip, i.e., a multiplex system, can simultaneously detect and sort a sample by using an array of photomultiplier tubes (PMT) for parallel analysis of different channels (27). This arrangement can be used to improve throughput or for successive sample enrichment, and can be adapted to provide a very high throughput to the microfluidic devices that exceeds the capacity permitted by conventional flow sorters. Circulation systems, particularly rotary circulation within a closed loop, e.g. for detection, can be used in cooperation with these and other features of the invention. Microfluidic pumps and valves are a preferred way of controlling fluid and sample flow. Microfabrication permits other technologies to be integrated or combined on a single chip, such as PCR (10), moving molecules or cells using optical tweezer/trapping (28-30), transformation of cells by electroporation (31), µTAS (33), and DNA hybridization (18). Detectors and/or light filters that are used to detect molecule or cell characteristics or their reporters can also be fabricated directly on the chip.

A device of the invention can be microfabricated with a sample solution reservoir or well at the inlet region, which is typically in fluid communication with an inlet channel. A reservoir may facilitate introduction of molecules or cells into the device and into the sample inlet channel of each analysis unit. An inlet region may have an opening, such as in the floor of the microfabricated chip, to permit entry of the sample into the device. The inlet region may also contain a connector adapted to receive a suitable piece of tubing, such as liquid chromatography or HPLC tubing, through which a sample may be supplied. Such an arrangement facilitates introducing the sample solution under positive pressure in order to achieve a desired flow rate through the channels. Outlet channels and wells can be similarly provided.

5.2.2. Substrate and Flow Channels

A typical analysis unit of the invention comprises an inlet region that is part of and feeds or communicates with a main channel, which in turn communicates with an outlet or with two (or more) branch channels at a junction or branch point, forming for example a T-shape or a Y-shape for sorting. Other shapes and channel geometries may be used as desired. The region at or surrounding the junction can also be referred to as a discrimination region, however, precise boundaries for the discrimination region are not required. A detection region is identified within, communicating, or coincident with a portion of the main channel downstream of the inlet region, and in sorting embodiments, at or upstream of the discrimination region or branch point. Precise boundaries for the detection region are not required, but are preferred. The discrimination region may be located immediately downstream of the detection region, or it may be separated by a suitable distance consistent with the size of the molecules, the channel dimensions, and the detection system. It will be appreciated that the channels can have any suitable shape or cross-section, such as tubular or grooved, and can be arranged in any suitable manner, so long as a flow can be directed from inlet to outlet, and from one channel into another, e.g. into at least one of two or more branch channels.

The channels of the invention are microfabricated, for example by etching a silicon chip using conventional photolithography techniques, or using a micromachining technology called "soft lithography", developed in the late 1990's (23). These and other microfabrication methods may be used to provide inexpensive miniaturized devices, and in the case of soft lithography, can provide robust devices having beneficial properties such as improved flexibility, stability, and mechanical strength. When optical detection is employed, the invention also provides minimal light scatter from molecule or cell suspension and chamber material. Devices according to the invention are relatively inexpensive and easy to set up. They can also be disposable, which greatly relieves many of the concerns of gel electrophoresis (for molecules) and for sterilization and permanent adsorption of particles unto the flow chambers and channels of conventional FACS machines (for cells). Using these kinds of techniques, microfabricated fluidic devices can replace the conventional gel electrophoresis and fluidic flow chambers of the prior art.

A microfabricated device of the invention is preferably fabricated from a silicon microchip or silicon elastomer. The dimensions of the chip are those of typical microchips, ranging between about 0.5 cm to about 5 cm per side and about 1 micron to about 1 cm in thickness. A typical device of the invention is one square inch in area. The device contains at least one analysis unit having a main channel with a central hybridization loop and a coincident detection region. Preferably the device also contains at least one inlet region (which may contain an inlet channel) and one or more outlet regions (which may have fluid communication with a branch channel in each region). In a sorting embodiment, at least one detection region cooperates with at least one discrimination point to divert flow via a detector-originated signal. It shall be appreciated that the "regions" and "channels" are in fluid communication with each other, and therefore they may overlap, i.e., there may be no clear boundary where a region or channel begins or ends. A microfabricated device can be transparent and can be covered with a material having transparent properties, e.g., a glass coverslip to permit detection of a reporter for example by an optical device, such as an optical microscope.

The dimensions of the channels and in particular of the detection region are influenced by the size of the molecules or cells under study. For polynucleotides, which are large by molecular standards, a typical length or diameter is about 3.4 angstroms per base pair. Thus, a DNA 49 kpbs long, such as Lambda phage DNA, is about 17 microns long when fully extended. A typical range of sizes for polynucleotides of the invention is from about 1 to about 200 kpbs, or about 0.3 to about 70 microns. Detection regions used for detecting molecules have a cross-sectional area large enough to allow a desired molecule to pass through without being substantially slowed down relative to the flow of the solution carrying it. At the small dimensions of preferred embodiments of the invention, e.g. channels of about 100 μm×10 μm, the Reynolds number is less than one, meaning that there is little or no turbulence. Nevertheless, to avoid "bottlenecks" and/or turbulence, and in embodiments where it is desirable to promote single-file flow, the channel dimensions, particularly in the detection region, should generally be at least about twice, preferably at least about five times as large per side or in diameter as the diameter of the largest molecule that will be passing through it.

For molecules such as DNA, the channels in a device are between about 2 to about 5 microns in width and between about 2 and about 4 or 5 microns in depth. Similarly, the volume of the detection region in a molecular analysis or sorting device is in the range of between about 10 to about 5000 femtoliters (fl), preferably about 40 or 50 fl to about 1000 or 2000 fl, most preferably on the order of about 200 fl. In preferred embodiments, the channels of the device, and particularly the channels of a target or detection loop, are preferably between about 10 μm and about 200 μm in width, typically 50-100 μm, and most preferably about 100 μm. The channels are preferably about 2-20 μm in depth for DNA or polynucleotide analysis, more typically about 10 μm. The detection region in preferred embodiments, e.g. the volume of a target loop, is between about 1 pl and about 1 nl.

To prevent material from adhering to the sides of the channels, the channels (and coverslip, if used) may have a coating which minimizes adhesion. Such a coating may be intrinsic to the material from which the device is manufactured, or it may be applied after the structural aspects of the channels have been microfabricated. "TEFLON" is an example of a coating that has suitable surface properties.

A silicon substrate containing the microfabricated flow channels and other components is preferably covered and sealed, most preferably with a transparent cover, e.g., thin glass or quartz, although other clear or opaque cover materials may be used. When external radiation sources or detectors are employed, the detection region is covered with a clear cover material to allow optical access to the molecules or cells. For example, anodic bonding to a "PYREX" cover slip can be accomplished by washing both components in an aqueous $H_2SO_4/H_2O_2$ bath, rinsing in water, and then, for example, heating to about 350 degrees C. while applying a voltage of 450V.

5.2.3. Switching and Flow Control

Electro-osmotic and pressure-driven flow are examples of methods or systems for flow control, that is, manipulating the flow of molecules cells, particles or reagents in one or more directions and/or into one or more channels of a microfluidic device of the invention (20, 24, 25, 34). Other methods may also be used, for example, electrophoresis and dielectrophoresis. In certain embodiments of the invention, the flow moves in one "forward" direction, e.g. from the inlet region through the main and branch channels to an outlet region. In other embodiments the direction of flow is reversible. Application of these techniques according to the invention provides more rapid and accurate devices and methods for analysis or sorting, for example, because the sorting occurs at or in a discrimination region that can be placed at or immediately after a detection region. This provides a shorter distance for molecules or cells to travel, they can move more rapidly and with less turbulence, and can more readily be moved, examined, and sorted in single file, i.e., one at a time. In a reversible embodiment, potential sorting errors can be avoided, for example by reversing and slowing the flow to re-read or resort a molecule or cell (or a plurality thereof) before irretrievably committing the molecule or cell to the outlet or to a particular branch channel.

Without being bound by any theory, electro-osmosis is believed to produce motion in a stream containing ions, e.g. a liquid such as a buffer, by application of a voltage differential or charge gradient between two or more electrodes. Neutral (uncharged) molecules or cells can be carried by the stream. Electro-osmosis is particularly suitable for rapidly changing the course, direction or speed of flow. Electrophoresis is believed to produce movement of charged objects in a fluid toward one or more electrodes of opposite charge, and away from one on or more electrodes of like charge. Because of its charged nature (2 charges for each base pair) DNA can be conveniently moved by electrophoresis in a buffer of appropriate pH.

Dielectrophoresis is believed to produce movement of dielectric objects, which have no net charge, but have regions that are positively or negatively charged in relation to each other. Alternating, non-homogeneous electric fields in the presence of particles, such as molecules, cells or beads, cause them to become electrically polarized and thus to experience dielectrophoretic forces. Depending on the dielectric polarizability of the particles and the suspending medium, dielectric particles will move either toward the regions of high field strength or low field strength. For example, the polarizability of living cells depends on their composition, morphology, and phenotype and is highly dependent on the frequency of the applied electrical field. Thus, cells of different types and in different physiological states generally possess distinctly different dielectric properties, which may provide a basis for cell separation, e.g., by differential dielectrophoretic forces. According to formulas provided in Fiedler et al. (25), individual manipulation of single particles requires field differences with dimensions close to the particles.

Manipulation is also dependent on permittivity (a dielectric property) of the particles with the suspending medium. Thus, polymer particles and living cells show negative dielectrophoresis at high-field frequencies in water. For example, dielectrophoretic forces experienced by a latex sphere in a 0.5 MV/m field (10V for a 20 micron electrode gap) in water are predicted to be about 0.2 piconewtons (pN) for a 3.4 micron latex sphere to 15 pN for a 15 micron latex sphere (25). These values are mostly greater than the hydrodynamic forces experienced by the sphere in a stream (about 0.3 pN for a 3.4 micron sphere and 1.5 pN for a 15 micron sphere). Therefore, manipulation of individual cells or particles can be accomplished in a streaming fluid, such as in a cell sorter device, using dielectrophoresis. Using conventional semiconductor technologies, electrodes can be microfabricated onto a substrate to control the force fields in a microfabricated sorting device of the invention. Dielectrophoresis is particularly suitable for moving objects that are electrical conductors. The use of AC current is preferred, to prevent permanent alignment of ions. Megahertz frequencies are suitable to provide a net alignment, attractive force, and motion over relatively long distances. E.g. Benecke (60).

Optical tweezers can also be used in the invention to trap and move objects, e.g. molecules or cells, with focused beams of light such as lasers. Flow can also be obtained and controlled by providing a pressure differential or gradient between one or more channels of a device or in a method of the invention.

Molecules or cells can be moved by direct mechanical switching, e.g. with on-off valves, or by squeezing the channels. Pressure control may also be used, for example by raising or lowering an output well to change the pressure inside the channels on the chip. See e.g. the devices and methods described in pending U.S. application Ser. No. 08/932,774 filed Sep. 25, 1997; No. 60/108,894 filed Nov. 17, 1998; No. 60/086,394 filed May 22, 1998; and No. 09/325,667 filed May 21, 1999 (molecular analysis systems). These methods and devices can further be used in combination with the methods and devices described in pending U.S. application Ser. No. 60/141,503 filed Jun. 28, 1999; No. 60/147,199 filed Aug. 3, 1999 and Ser. No. 60/186,856 filed Mar. 3, 2000 entitled "Microfabricated Elastomeric Valve and Pump Systems". Each of these references is hereby incorporated by reference in its entirety.

Different switching and flow control mechanisms can be combined on one chip or in one device and can work independently or together as desired.

5.2.4. Detection and Discrimination for Sorting

The detector can be any device or method for interrogating a molecule or cell as it passes through the detection region. Typically, molecules or cells are to be analyzed or sorted according to a predetermined characteristic that is directly or indirectly detectable, and the detector is selected or adapted to detect that characteristic. A preferred detector is an optical detector, such as a microscope, which may be coupled with a computer and/or other image processing or enhancement devices to process images or information produced by the microscope using known techniques. For example, molecules can be sorted by size or molecular weight. Cells can be sorted for whether they contain or produce a particular protein, by using an optical detector to examine each cell for an optical indication of the presence or amount of that protein. The protein may itself be detectable, for example by a characteristic fluorescence, or it may be labeled or associated with a reporter that produces a detectable signal when the desired protein is present, or is present in at least a threshold amount. There is no limit to the kind or number of molecule or cell characteristics that can be identified or measured using the techniques of the invention, which include without limitation surface characteristics of the cell and intracellular characteristics, provided only that the characteristic or characteristics of interest for sorting can be sufficiently identified and detected or measured to distinguish cells having the desired characteristic(s) from those which do not. For example, any label or reporter as described herein can be used as the basis for sorting molecules or cells, i.e. detecting them to be collected.

In preferred embodiments, the molecules or cells are analyzed and/or separated based on the intensity of a signal from an optically-detectable reporter bound to or associated with them as they pass through a detection window or "detection region" in the device. Molecules or cells having an amount or level of the reporter at a selected threshold or within a selected range can be diverted into a predetermined outlet or branch channel of the device. The reporter signal is collected by a microscope and measured by a photomultiplier tube (PMT). A computer digitizes the PMT signal and controls the flow via valve action or electro-osmotic potentials. Alternatively, the signal can be recorded or quantified, as a measure of the reporter and/or its corresponding characteristic or marker, e.g. for purposes of evaluation without necessarily proceeding to sort the molecules or cells.

In one embodiment, the chip is mounted on an inverted optical microscope. Fluorescence produced by a reporter is excited using a laser beam focused on molecules (e.g. DNA) or cells passing through a detection region. Fluorescent reporters include, e.g., rhodamine, fluorescein, Texas red, Cy 3, Cy 5, phycobiliprotein, green fluorescent protein (GFP), YOYO-1, and PicoGreen. In molecular fingerprinting applications, the reporter labels are preferably a fluorescently-labeled single nucleotides, such as fluorescein-dNTP, rhodamine-dNTP, Cy3-dNTP, Cy5-dNTP, where dNTP represents dATP, dTTP, dUTP or dCTP. The reporter can also be chemically-modified single nucleotides, such as biotin-dNTP. Thus, in one aspect of the invention, the device can determine the size or molecular weight of molecules such as polynucleotide fragments passing through the detection region, or the presence or degree of some other characteristic indicated by a reporter. If desired, the molecules can be sorted based on this analysis.

To detect a reporter or determine whether a molecule has a desired characteristic, the detection region may include an apparatus for stimulating a reporter for that characteristic to emit measurable light energy, e.g., a light source such as a laser, laser diode, high-intensity lamp, (e.g., mercury lamp), and the like. In embodiments where a lamp is used, the channels are preferably shielded from light in all regions except the detection region. In embodiments where a laser is used, the laser can be set to scan across a set of detection regions from different analysis units. In addition, laser diodes may be microfabricated into the same chip that contains the analysis units. Alternatively, laser diodes may be incorporated into a second chip (i.e., a laser diode chip) that is placed adjacent to the microfabricated sorter chip such that the laser light from the diodes shines on the detection region(s).

In preferred embodiments, an integrated semiconductor laser and/or an integrated photodiode detector are included on the silicon wafer in the vicinity of the detection region. This design provides the advantages of compactness and a shorter optical path for exciting and/or emitted radiation, thus minimizing distortion.

5.2.5. Sorting Schemes

According to the invention, molecules or cells are sorted dynamically in a flow stream of microscopic dimensions, based on the detection or measurement of a characteristic, marker or reporter that is associated with the molecules or cells. The stream is typically but not necessarily continuous, and may be stopped and started, reversed, or changed in speed. Prior to sorting, a liquid that does not contain sample molecules or cells can be introduced at an inlet region of the chip (e.g., from an inlet well or channel) and is directed through the device by capillary action, to hydrate and prepare the device for sorting. If desired, the pressure can be adjusted or equalized for example by adding buffer to an outlet region. The liquid typically is an aqueous buffer solution, such as ultrapure water (e.g., 18 mega ohm resistivity, obtained for example by column chromatography), ultrapure water, 10 mM Tris HCL and 1 mM EDTA (TE), phosphate buffer saline (PBS), and acetate buffer. Any liquid or buffer that is physiologically compatible with the population of molecules or cells to be sorted can be used.

A sample solution containing a mixture or population of molecules or cells in a suitable carrier fluid (such as a liquid or buffer described above) is supplied to the inlet region. The capillary force causes the sample to enter the device. The force and direction of flow can be controlled by any desired method for controlling flow, for example, by a pressure differential, by valve action, or by electro-osmotic flow, e.g., produced by electrodes at inlet and outlet channels. This permits the movement of the molecules or cells into one or more desired branch channels or outlet regions.

A "forward" sorting algorithm, according to the invention, includes embodiments where molecules or cells from an inlet channel flow through the device to a predetermined branch or outlet channel (which can be called a "waste channel"), until the level of measurable reporter is above a pre-set threshold. At that time, the flow is diverted to deliver the molecule or cell to another channel. For example, in an electro-osmotic embodiment, where switching is virtually instantaneous and throughput is limited by the highest voltage, the voltages are temporarily changed to divert the chosen molecule or cell to another predetermined outlet channel (which can be called a "collection channel"). Sorting, including synchronizing detection of a reporter and diversion of the flow, can be controlled by various methods including computer or microprocessor control. Different algorithms for sorting in the microfluidic device can be implemented by different computer programs, such as programs used in conventional FACS devices for sorting cells. For example, a programmable card can be used to control switching, such as a Lab PC 1200 Card, available from National Instruments, Austin, Tex. Algorithms as sorting procedures can be programmed using C++, LAB-VIEW, or any suitable software. The method is advantageous, for example, because conventional gel electrophoresis methods are generally not automated or under computer control.

A "reversible" sorting algorithm can be used in place of a "forward" mode, for example in embodiments where switching speed may be limited. For example, a pressure-switched scheme can be used instead of electro-osmotic flow and does not require high voltages and may be more robust for longer runs. However, mechanical constraints may cause the fluid switching speed to become rate-limiting. In a pressure-switched scheme the flow is stopped when a molecule or cell of interest is detected. By the time the flow stops, the molecule or cell may be past the branch point and be part-way down the waste channel. In this situation, a reversible embodiment can be used. The system can be run backwards at a slower (switchable) speed (e.g., from waste to inlet), and the molecule or cell is then switched to a different channel. At that point, a potentially mis-sorted molecule or cell is "saved", and the device can again be run at high speed in the forward direction. This "reversible" sorting method is not possible with standard FACS machines or in gel electrophoresis technologies. FACS machines mostly sort aerosol droplets which cannot be reversed back to the chamber, in order to be redirected. The aerosol droplet sorter are virtually irreversible. In gel electrophoresis, molecules such as polynucleotides are drawn through a gel by an electric current and migrate at different rates proportional to their molecular weights. Individual molecules can not be reversed through the gel, and indeed, altering the rate or direction of migration would prevent meaningful use of the technique. Reversible sorting is particularly useful for identifying rare molecules or cells (e.g., in molecular evolution and cancer cytological identification), or molecules or cells that are few in number, which may be misdirected due to a margin of error inherent to any fluidic device. The reversible nature of the device of the invention permits a reduction in this possible error.

A "reversible" sorting method permits multiple time course measurements of a single molecule or cell. This allows for observations or measurements of the same molecule or cell at different times, because the flow reverses the molecule or cell back into the detection window before directing it to a downstream channel. Measurements can be compared or confirmed, and changes in molecule or cell properties over time can be examined, for example in kinetic studies.

When trying to separate molecules or cells in a sample at a very low ratio to the total number of molecules or cells, a sorting algorithm can be implemented that is not limited by the intrinsic switching speed of the device. Consequently, the molecules or cells flow at the highest possible static (non-switching) speed from the inlet channel to the waste channel. Unwanted molecules or cells can be directed into the waste channel at the highest speed possible, and when a desired molecule or cell is detected, the flow can be slowed down and then reversed, to direct it back into the detection region, from where it can be redirected (i.e. to accomplish efficient switching). Hence the molecules or cells can flow at the highest possible static speed.

Preferably, the fluid carrying the molecules or cells has a relatively low Reynolds Number, for example $10^{-2}$. The Reynolds Number represents an inverse relationship between the density and velocity of a fluid and its viscosity in a channel of given length. More viscous, less dense, slower moving fluids over a shorter distance will have a lower Reynolds Number, and are easier to divert, stop, start, or reverse without turbulence. Because of the small sizes and slow velocities, microfabricated fluid systems are often in a low Reynolds number regime ($<<1$). In this regime, inertial effects, which cause turbulence and secondary flows, are negligible; viscous effects dominate the dynamics. These conditions are advantageous for sorting, and are provided by microfabricated devices of the invention. Accordingly the microfabricated devices of the invention are preferably if not exclusively operated at a low or very low Reynold's number. Exemplary sorting schemes are shown diagrammatically in FIGS. 11A and B and FIGS. 12A and B.

6. EXAMPLES

6.1. Microfabricated Polynucleotide Sorting Device

Figure 1:
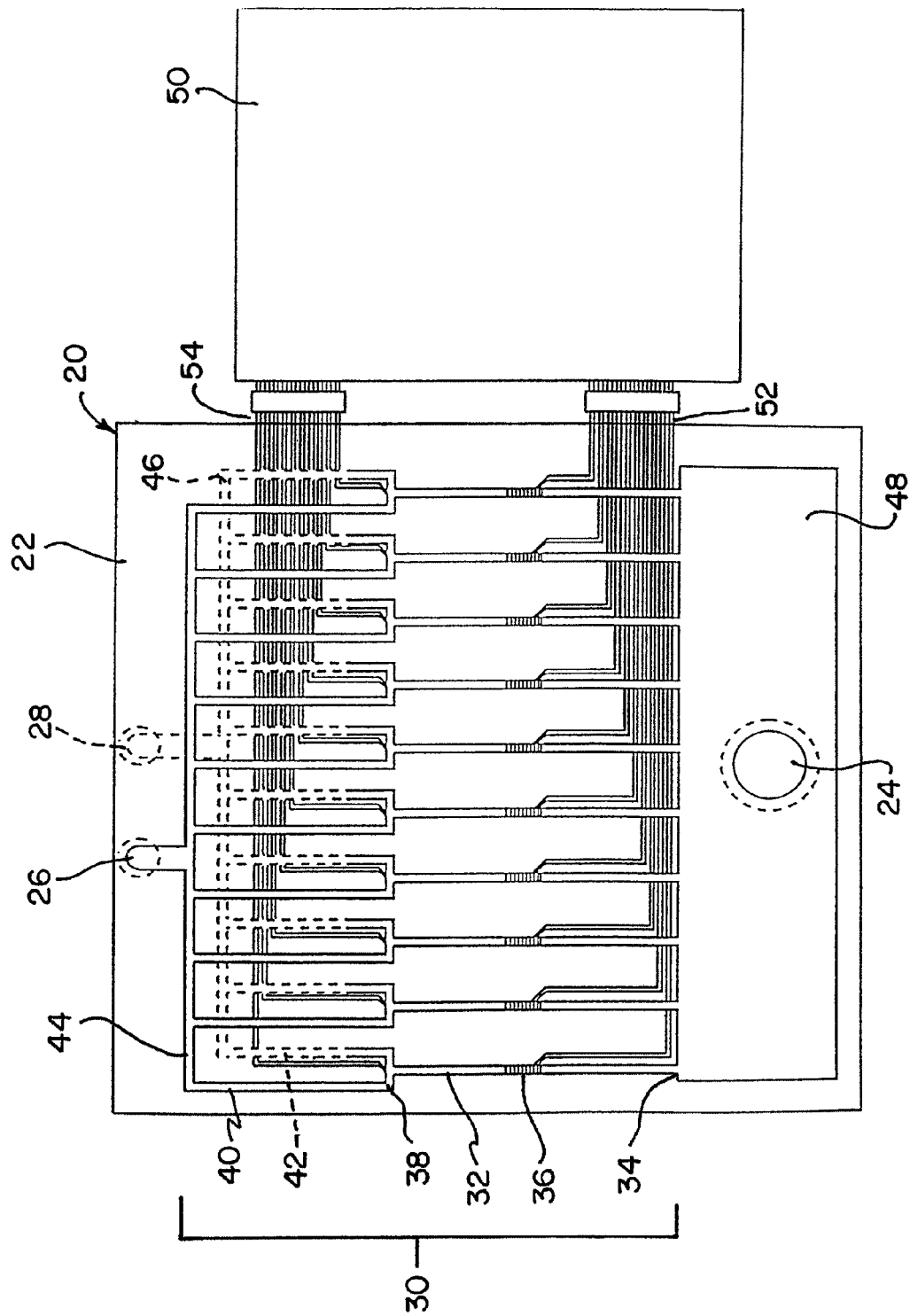
FIG. 1 shows a nucleic acid sorting device in accordance with one embodiment of the invention.

FIG. 1 shows an embodiment of a microfabricated polynucleotide sorting device 20 in accordance with the invention. The device is preferably fabricated from a silicon microchip 22. The dimensions of the chip are those of typical microchips, ranging between about 0.5 cm to about 5 cm per side and about 0.1 mm to about 1 cm in thickness. The device contains a solution inlet 24, two or more solution outlets, e.g. outlets 26 and 28, and at least one analysis unit, such as the unit at 30.

Each analysis unit includes a main channel 32 having at one end a sample inlet 34, and downstream of the sample inlet, a detection region 36, and downstream of the detection region 36 a discrimination region 38. A plurality of branch channels, such as channels 40 and 42, are in fluid communication with and branch out from the discrimination region. The dimensions of the main and branch channels are typically between about 1 μm and 10 μm per side, but may vary at various points to facilitate analysis, sorting and/or collection of molecules.

In embodiments such as shown in FIG. 1, where the device contains a plurality of analysis units, the device may further contain collection manifolds, such as manifolds 44 and 46, to facilitate collection of sample from corresponding branch channels of different analysis units for routing to the appropriate solution outlet. The manifolds are preferably microfabricated into different levels of the device, as indicated by the dotted line representing manifold 46. Similarly, such embodiments may include a sample solution reservoir, such as reservoir 48, to facilitate introduction of sample into the sample inlet of each analysis unit.

Also included with the device is a processor, such as processor 50. The processor can be integrated into the same chip as contains the analysis unit(s), or it can be separate, e.g., an independent microchip connected to the analysis unit-containing chip via electronic leads, such as leads 52 (connected to the detection region(s) and 54 (connected to the discrimination region(s)).

Figure 2:
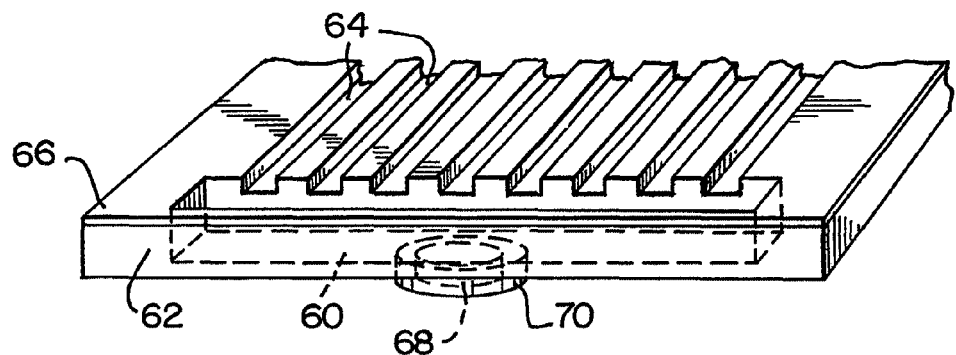
FIG. 2 shows a partial perspective view of a nucleic acid sorting device, showing a sample solution reservoir and sample inlet.

As mentioned above, the device may be microfabricated with a sample solution reservoir to facilitate introduction of a polynucleotide solution into the device and into the sample inlet of each analysis unit. With reference to FIG. 2, the reservoir is microfabricated into the silicon substrate of the chip 62, and is covered, along with the channels (such as main channel 64) of the analysis units, with a glass coverslip 66. The device solution inlet comprises an opening 68 in the floor of the microchip. The inlet may further contain a connector 70 adapted to receive a suitable piece of tubing, such as liquid chromatography or HPLC tubing, through which the sample may be supplied. Such an arrangement facilitates introducing the sample solution under positive pressure, to achieve a desired flow rate through the channels as described below.

Downstream of the sample inlet of the main channel of each analysis unit is the detection region, designed to detect the level of an optically-detectable reporter associated with polynucleotides present in the region. Exemplary embodiments of detection regions in devices of the invention are shown in FIGS. 3A and 3B.

6.2. Photodiode Detectors

Figure 3A:
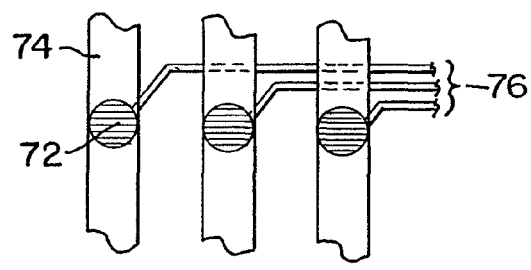
FIG. 3A shows one embodiment of a detection region used in a nucleic acid sorting device, having an integrated photodiode detector.
Figure 3B:
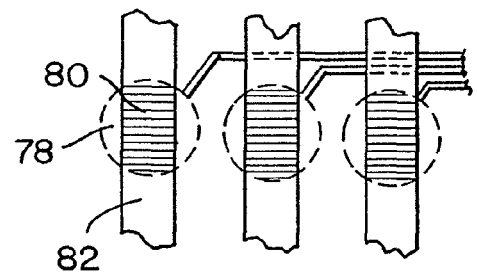
FIG. 3B shows another embodiment of a detection region, having an integrated photodiode detector, and providing a larger detection volume (than the embodiment of FIG. 3A).

With reference to FIG. 3A, each detection region is formed of a portion of the main channel of an analysis unit and a photodiode, such as photodiode 72, located in the floor of the main channel. In this embodiment, the area detectable by the detection region is the circular portion each channel defined by the receptive field of the photodiode in that channel. The volume of the detection region is the volume of a cylinder with a diameter equal to the receptive field of the photodiode and a height equal to the depth of the channel above the photodiode.

The signals from the photodiodes are carried via output lines 76 to the processor (not shown), which processes the signals into values corresponding to the length of the polynucleotide giving rise to the signal. The processor then uses this information, for example, to control active elements in the discrimination region. The processor may process the signals into values for comparison with a predetermined or reference set of values for analysis or sorting.

When more than one detection region is used, the photodiodes in the laser diode chip are preferably spaced apart relative to the spacing of the detection regions in the analysis unit. That is, for more accurate detection, the photodiodes are placed apart at the same spacing as the spacing of the detection region.

The processor can be integrated into the same chip that contains the analysis unit(s), or it can be separate, e.g., an independent microchip connected to the analysis unit-containing chip via electronic leads that connect to the detection region(s) and/or to the discrimination region(s), such as by a photodiode. The processor can be a computer or microprocessor, and is typically connected to a data storage unit, such as computer memory, hard disk, or the like, and/or a data output unit, such as a display monitor, printer and/or plotter.

The types and numbers of molecules or cells, based on detection of a reporter associated with or bound to the molecules or cells passing through the detection region, can be calculated or determined, and the data obtained can be stored in the data storage unit. This information can then be further processed or routed to the data outlet unit for presentation, e.g. histograms, of the types of molecules or cells (or levels of a cell protein, saccharide), or some other characteristic. The data can also be presented in real time as the sample is flowing through the device.

With reference to FIG. 3B, the photodiode 78 can be larger in diameter than the width of the main channel, forming a detection region 80 that is longer (along the length of the main channel 82) than it is wide. The volume of such a detection region is approximately equal to the cross-sectional area of the channel above the diode multiplied by the diameter of the diode.

In a preferred sorting embodiment the detection region is connected by the main channel to the discrimination region. The discrimination region may be located immediately downstream of the detection region, or may be separated by a suitable length of channel. Constraints on the length of channel between the detection and discrimination regions are discussed below, with respect to the operation of the device. This length is typically between about 1 μm and about 2 cm. The discrimination region is at the junction of the main channel and the branch channels. It comprises the physical location where molecules are directed into a selected branch channel. The means by which the molecules or cells are directed into a selected branch channel may (i) be present in the discrimination region, as in, e.g., electrophoretic or microvalve-based discrimination, or (ii) be present at a distant location, as in, e.g., electroosmotic or flow stoppage-based discrimination.

If desired, the device may contain a plurality of analysis units, i.e., more than one detection and discrimination region, and a plurality of branch channels which are in fluid communication with and branch out from the discrimination regions. It will be appreciated that the position and fate of molecules or cells in the discrimination region can be monitored by additional detection regions installed, for example, immediately upstream of the discrimination region and/or within the branch channels immediately downstream of the branch point. The information obtained by the additional detection regions can be used by a processor to continuously revise estimates of the velocity of the molecules or cells in the channels and to confirm that molecules or cells having a selected characteristic enter the desired branch channel.

A group of manifolds (a region consisting of several channels which lead to or from a common channel) can be included to facilitate movement of sample from the different analysis units, through the plurality of branch channels and to the appropriate solution outlet. Manifolds are preferably microfabricated into the chip at different levels of depth. Thus, devices of the invention having a plurality of analysis units can collect the solution from associated branch channels of each unit into a manifold, which routes the flow of solution to an outlet. The outlet can be adapted for receiving, for example, a segment of tubing or a sample tube, such as a standard 1.5 ml centrifuge tube. Collection can also be done using micropipettes.

6.3. Valve Structures

Figure 4A:
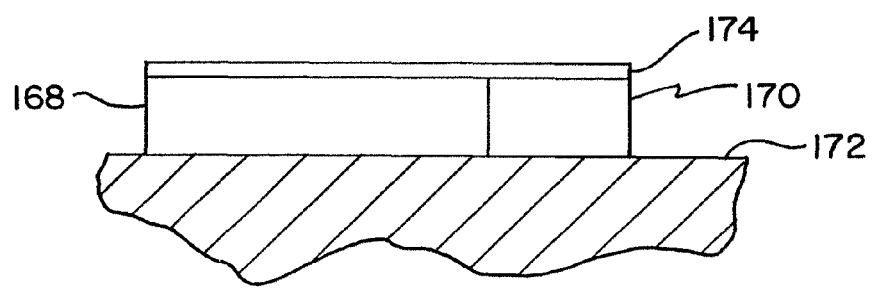
FIGS. 4A-4B show one embodiment of a valve within a branch channel of a nucleic acid sorting device, and steps in fabrication of the valve.
Figure 4B:
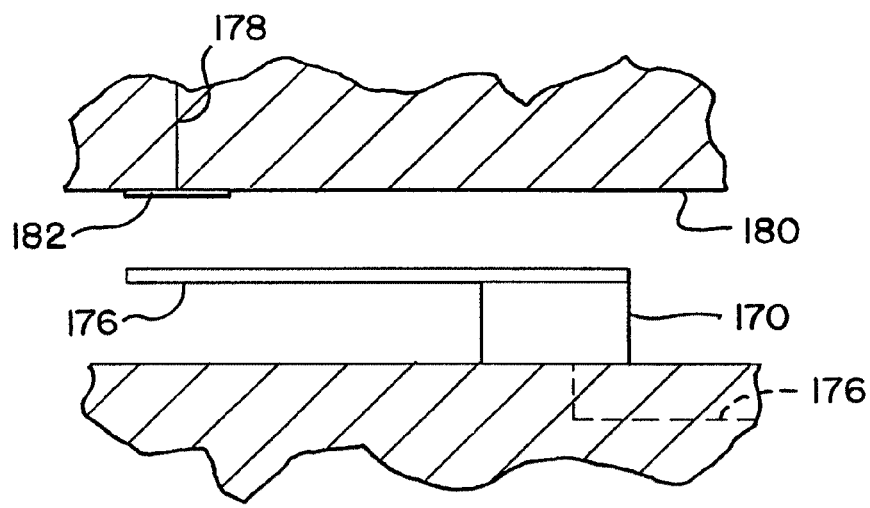

In an embodiment where pressurized flow is used, valves can be used to block or unblock the pressurized flow of molecules or cells through selected channels. A thin cantilever, for example, may be included within a branch point, as shown in FIGS. 4A and 4B, such that it may be displaced towards one or the other wall of the main channel, typically by electrostatic attraction, thus closing off a selected branch channel. Electrodes are on the walls of the channel adjacent to the end of the cantilever. Suitable electrical contacts for applying a potential to the cantilever are also provided in a similar manner as the electrodes. Because the cantilever in FIG. 4B is parallel to the direction of etching, it may be formed of a thin layer of silicon by incorporating the element into the original photoresist pattern. The cantilever is preferably coated with a dielectric material such as silicon nitride, as described in Wise, et al., 1995 (46), for example, to prevent short circuiting between the conductive surfaces.

Alternatively, a valve may be situated within each branch channel, rather than at the branch point, to close off and terminate pressurized flow through selected channels. Because the valves are located downstream of the discrimination region, the channels in this region may be formed having a greater width than in the discrimination region, which simplifies the formation of valves.

A valve within a channel may be microfabricated, if desired, in the form of an electrostatically operated cantilever or diaphragm. Techniques for forming such elements are well known in the art (e.g., 24, 40, 46, 47, 48). Typical processes include the use of selectively etched sacrificial layers in a multilayer structure or, for example, the undercutting of a layer of silicon dioxide via anisotropic etching. For example, to form a cantilever within a channel, as illustrated in FIGS. 4A and 4B, a sacrificial layer 168 may be formed adjacent to a small section of a non-etchable material 170, using known photolithography methods, on the floor of a channel, as shown in FIG. 4A. Both layers can then be coated with, for example, silicon dioxide or another non-etchable layer, as shown at 172. Etching of the sacrificial layer deposits the cantilever member 174 within the channel, as shown in FIG. 4B. Suitable materials for the sacrificial layer, non-etchable layers and etchant include undoped silicon, p-doped silicon and silicon dioxide, and the etchant EDP (ethylene diamine/pyrocatechol), respectively. Because the cantilever in FIG. 4B is parallel to the direction of etching, it may be formed of a thin layer of silicon by incorporating the element into the original photoresist pattern. The cantilever is preferably coated with a dielectric material such as silicon nitride, as described in (46) for example, to prevent short circuiting between the conductive surfaces.

The width of the cantilever or diaphragm should approximately equal that of the channel, allowing for movement within the channel. If desired, the element may be coated with a more malleable material, such as a metal, to allow for a better seal. Such coating may also be employed to render a non-conductive material, such as silicon dioxide, conductive.

As above, suitable electrical contacts are provided for displacing the cantilever or diaphragm towards the opposing surface of the channel. When the upper surface is a glass cover plate, as described below, electrodes and contacts may be deposited onto the glass.

It will be apparent to one of skill in the field that other types of valves or switches can be designed and fabricated, using well known photolithographic or other microfabrication techniques, for controlling flow within the channels of the device. Multiple layers of channels can also be prepared.

Operation of the valves or charging of the electrodes, in response to the level of fluorescence measured from an analyte molecule, is controlled by the processor, which receives this information from the detector. All of these components are operably connected in the apparatus, and electrical contacts are included as necessary, using standard microchip circuitry.

In preferred embodiments, an integrated semiconductor laser and/or an integrated photodiode detector are included on the silicon wafer in the vicinity of the detection region. This design provides the advantages of compactness and a shorter optical path for exciting and/or emitted radiation, thus minimizing distortion.

The silicon substrate containing the microfabricated flow channels and other components is covered and sealed, preferably with a thin glass or quartz cover, although other clear or opaque cover materials may be used when external radiation sources or detectors are employed, the interrogation region is covered with a clear cover material to allow optical access to the analyte molecules. Anodic bonding to a "PYREX" cover slip may be accomplished by washing both components in an aqueous $H_2SO_4/H_2O_2$ bath, rinsing in water, and then heating to about 350° C. while applying a voltage of, e.g., 450V.

6.4. Examples of Microchip Architecture For Sorting

As illustrated with respect to FIGS. 5A-5D, there are a number of ways in which cells can be routed or sorted into a selected branch channel.

Figure 5A:
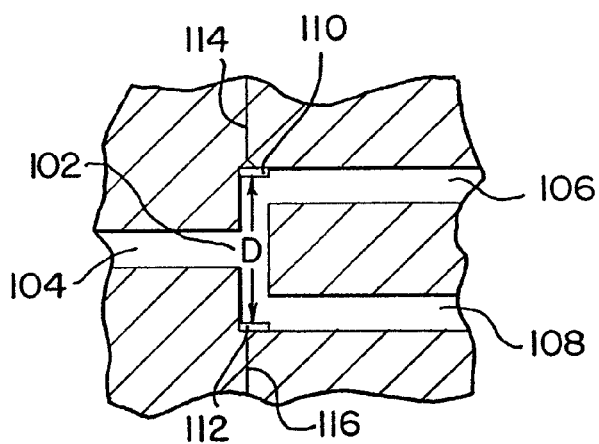
FIG. 5A shows one embodiment of a discrimination region used in a nucleic acid sorting device, having electrodes disposed within the channels for electrophoretic discrimination.

FIG. 5A shows a discrimination region 102, which is suitable for electrophoretic discrimination as the sorting technique. The discrimination region is preceded by a main channel 104. A junction divides the main channel into two branch channels 106 and 108. The discrimination region 102 includes electrodes 110 and 112, positioned on outer side walls of the branch channels 106 and 108, and which connect to leads 114 and 116. The leads are connected to a voltage source (not shown) incorporated into or controlled by a processor (not shown), as described, infra. The distance (D) between the electrodes is preferably less than the average distance separating the cells during flow through the main channel. The dimensions of the electrodes are typically the same as the dimensions of the channels in which they are positioned, e.e such that the electrodes are as high and wide as the channel.

Figure 5B:
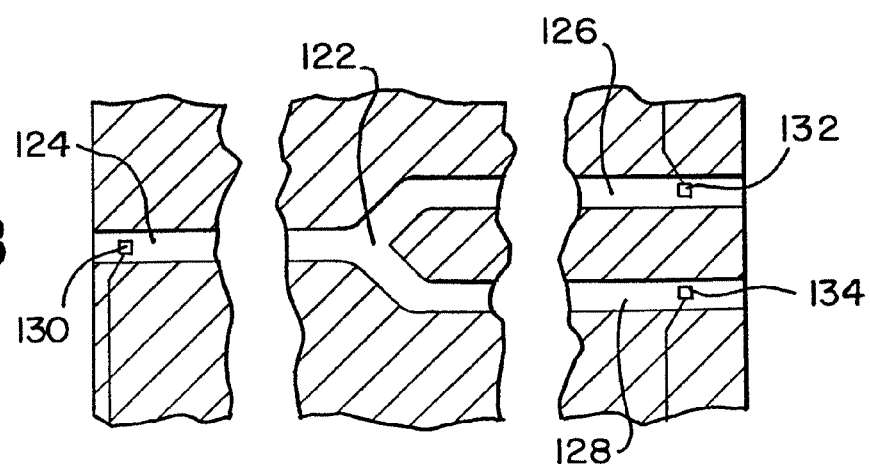
FIG. 5B shows another embodiment of a discrimination region used in a nucleic acid sorting device, having electrodes disposed for electroosmotic discrimination.

The discrimination region shown in FIG. 5B is suitable for use in a device that employs electro-osmotic flow, to move the molecules or cells and bulk solution through the device. FIG. 4B shows a discrimination region 122 which is preceded by a main channel 124. The main channel contains a junction that divides the main channel into two branch channels 126 and 128. An electrode 130 is placed downstream of the junction of the main channel, for example near the sample inlet of main channel. Electrodes are also placed in each branch channel electrodes 132 and 134). The electrode 130 can be negative and electrodes 132 and 134 can be positive (or vice versa) to establish bulk solution flow according to well-established principles of electro-osmotic flow (1E974: 25).

After a molecule or cell passes the detection region (not shown) and enters the discrimination region 122 (e.g. between the main channel and the two branch channels) the voltage to one of the electrodes 132 or 134 can be shut off, leaving a single attractive force that acts on the solution and the molecule or cell to influence it into the selected branch channel. As above, the appropriate electrodes are activated after the molecule or cell has committed to the selected branch channel in order to continue bulk flow through both channels. In one embodiment, the electrodes are charged to divert the flow into one branch channel, for example channel 126, which can be called a waste channel. In response to a signal indicating that a molecule or cell has been identified or selected for collection, the charge on the electrodes can be changed to divert the selected molecule or cell into the other channel (channel 128), which can be called a collection channel.

Figure 5C:
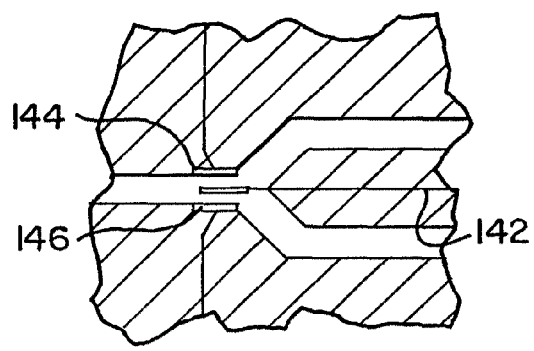
FIGS. 5C and 5D show two further embodiments of a discrimination region, having valves disposed for pressure electrophoretic separation, where the valves are within the branch point, as shown in 4C, or within the branch channels, as shown in 4D.

In another embodiment of the invention, shown in FIG. 5C, the molecules or cells are directed into a predetermined branch channel via a valve 140 in the discrimination region. The valve 140 comprises a thin extension of material to which a charge can be applied via an electrode lead 142. The valve 140 is shown with both channels open, and can be deflected to close either branch channel by application of a voltage across electrodes 144 and 146. A molecule or cell is detected and chosen for sorting in the detection region (not shown), and can be directed to the appropriate channel by closing off the other channel, e.g. by applying, removing or changing a voltage applied to the electrodes. The valve can also be configured to close one channel in the presence of a voltage, and to close the other channel in the absence of a voltage.

Figure 5D:
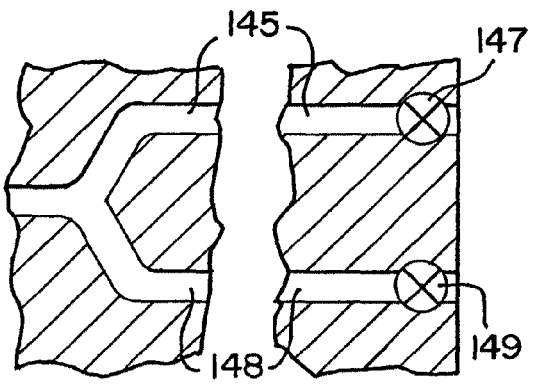

FIG. 5D shows another embodiment of a discrimination region of the invention, which uses flow stoppage in one or more branch channels as the discrimination means. The sample solution moves through the device by application of positive pressure at an end where the solution inlet is located. Discrimination or routing of the molecules or cells is affected by simply blocking a branch channel (145 or 148) or a branch channel sample outlet using valves in a pressure-driven flow (147 or 149). Due to the small size scale of the channels and the incompressibility of liquids, blocking the solution flow creates an effective "plug" in the non-selected branch channel, thereby temporarily routing the molecule or cell together with the bulk solution flow into the selected channel. Valve structures can be incorporated downstream from the discrimination region, which are controlled by the detection region, as described herein.

Alternatively, the discrimination function represented in FIG. 51D may be controlled by changing the hydrostatic pressure at the sample outlets of one or both branch channels 145 or 148. If the branch channels in a particular analysis unit have the same resistance to fluid flow, and the pressure at the sample inlet of the main channel of an analysis unit is P, then the fluid flow out of any selected branch channel can be stopped by applying a pressure P/n at the sample outlet of the desired branch channel, where n is the number of branch channels in the analysis unit. Accordingly, in an analysis unit having two branch channels, the pressure applied at the outlet of the branch to be blocked is P/2.

As shown in FIG. 5D, a valve is situated within each branch channel, rather than at the branch point, to close off and terminate pressurized flow through selected channels. Because the valves are located at a point downstream from the discrimination region, the channels in this region may be formed having a greater width than in the discrimination region in order to simplify the formation of valves. The width of the cantilever or diaphragm should approximately equal the width of the channel, allowing for movement within the channel. If desired, the element may be coated with a more malleable material, such as a metal, to allow for a better seal. Such coating may also be employed to render a non-conductive material, such as silicon dioxide, conductive. As above, suitable electrical contacts are provided for displacing the cantilever or diaphragm towards the opposing surface of the channel. When the upper surface is a glass cover plate, electrodes and contacts may be deposited onto the glass.

6.5. Cascade Device

Figure 6:
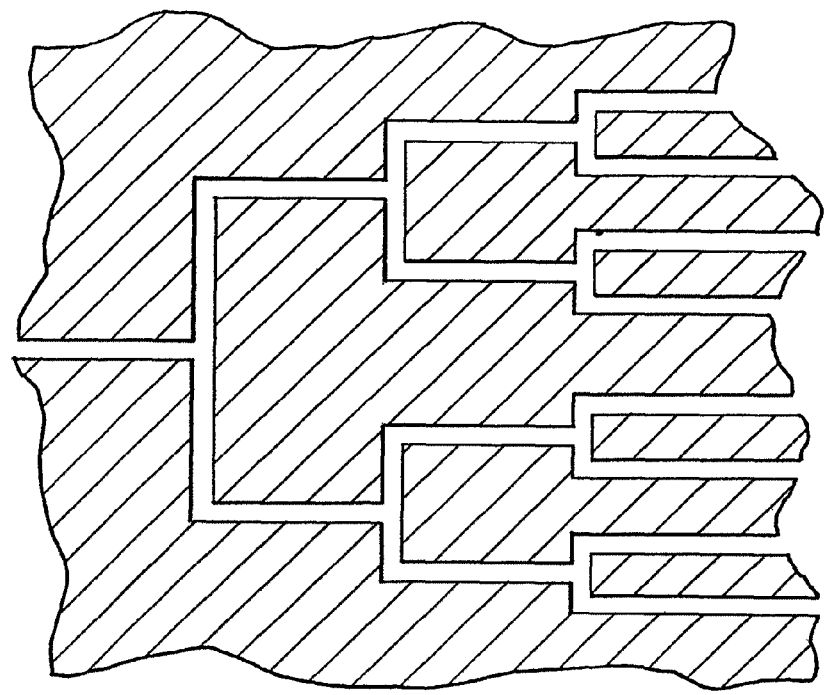
FIG. 6 shows a device with analysis units containing a cascade of detection and discrimination regions suitable for successive rounds of polynucleotide or cell sorting.

FIG. 6 shows a device with analysis units containing a cascade of detection and discrimination regions suitable for successive rounds of polynucleotide or cell sorting. Such a configuration may be used, for example, with a polynucleotide or cells sorting device to generate a series of samples containing "fractions" of polynucleotides, where each fraction contains a specific size range of polynucleotide fragments (e.g., the first fraction contains 100-500 bp fragments, the next 500-1000 bp fragments, and so on). In a cell sorting device, such a cascade configuration may be used to sequentially assay the cell for, e.g., three different fluorescent dyes corresponding to expression of three different molecular markers. Samples collected at the outlets of the different branch channels contain pools of cells expressing defined levels of each of the three markers. The number of reporters employed, and therefore the number of markers of interest, can be varied as desired, e.g. to meet the needs of a particular experiment or application.

6.6. Microfabricated Polynucleotide Analysis Device

Also included in the present invention is a microfabricated polynucleotide analysis device suitable for quantitation and analysis of the size distribution of polynucleotide fragments in solution. Such a device is a simplified version of the sorting device described above, in that analysis units in the device need not contain a discrimination region or branch channels, and the device need not contain a means for directing molecules to selected branch channels. Each analysis unit comprises a single main channel containing a detection region as described above. Since the optics which collect the optical signal (e.g., fluorescence) can be situated immediately adjacent the flow stream (e.g., diode embedded in the channel of a microscope objective adjacent a glass coverslip covering the channel), the signal-to-noise ratio of the signal collected using a microfabricated polynucleotide analysis device of the invention is high relative to other types of devices. Specifically, the invention allows, e.g., the use of oil-immersion high numerical aperture (N.A.) microscope objectives to collect the light (e.g., 1.4 N.A.) Since the collection of light is proportional to the square of the N.A., a 1.4 N.A. objective provides about a four-fold better signal than an 0.8 N.A. objective.

6.7. Microfabricated Cell Sorting Device

The invention also includes a microfabricated device for sorting reporter-labeled cells by the level of reporter they contain. The device is similar to polynucleotide-sorting devices described above, but is adapted for handling particles on the size scale of cells rather than molecules. This difference is manifested mainly in the dimensions of the microfabricated channels, detection and discrimination regions. Specifically, the channels in the device are typically between about 20 μm and about 500 μm in width and between about 20 μm and about 500 μm in depth, to allow for an orderly flow of cells in the channels. Similarly, the volume of the detection region in a cell sorting device is larger than that of the polynucleotide sorting device, typically being in the range of between about 10 pl and 100 nl. To prevent the cells from adhering to the sides of the channels, the channels (and coverslip) preferably contain a coating which minimizes cell adhesion. Such a coating may be intrinsic to the material from which the device is manufactured, or it may be applied after the structural aspects of the channels have been microfabricated. An exemplary coating has the surface properties of a material such as "TEFLON".

The device may be used to sort any procaryotic (e.g., bacterial) or eukaryotic (e.g., mammalian) cells which can be labeled (e.g., via antibodies) with optically-detectable reporter molecules (e.g., fluorescent dyes). Exemplary mammalian cells include human blood cells, such as human peripheral blood mononuclear cells (PBMCs). The cells can be labeled with antibodies directed against any of a variety of cell marker antigens (e.g., HLA DR, CD3, CD4, CD8, CD11a, CD11c, CD14, CD16, CD20, CD45, CD45RA, CD62L, etc.), and the antibodies can in turn be detected using an optically-detectable reporter (either via directly conjugated reporters or via labeled secondary antibodies) according to methods known in the art.

It will be appreciated that the cell sorting device and method described above can be used simultaneously with multiple optically-detectable reporters having distinct optical properties. For example, the fluorescent dyes fluorescein (FITC), phycoerythrin (PE), and "CYCHROME" (Cy5-PE) can be used simultaneously due to their different excitation and emission spectra. The different dyes may be assayed, for example, at successive detection and discrimination regions. Such regions may be cascaded as shown in FIG. 6 to provide samples of cells having a selected amount of signal from each dye.

6.8. Microfabrication of a Silicon Device

Analytical devices having microscale flow channels, valves and other elements can be designed and fabricated from a solid substrate material. Silicon is a preferred substrate material because of the well developed technology permitting its precise and efficient fabrication, but other materials may be used, including polymers such as polytetrafluoroethylenes. Micromachining methods well known in the art include film deposition processes, such as spin coating and chemical vapor deposition, laser fabrication or photolithographic techniques, or etching methods, which may be performed by either wet chemical or plasma processes. (See, for example, Angell et al. (48) and Manz et al. (49).

FIGS. 7A-7D illustrate the initial steps in microfabricating the discrimination region portion of a nucleic acid sorting device (e.g. Device 20 in FIG. 1) by photolithographic techniques. As shown, the structure includes a silicon substrate 160. The silicon wafer which forms the substrate is typically washed in a 4:1 $H_2SO_4/H_2O$ bath, rinsed in water and spun dry. A layer 162 of silicon dioxide, preferably about 0.5 µm in thickness, is formed on the silicon, typically by heating the silicon wafer to 800-1200° C. in an atmosphere of steam. The oxide layer is then coated with a photoresist layer 164, preferably about 1 µm inch-thickness. Suitable negative or positive resist materials are well known. Common negative resist materials include two-component bisarylazide/rubber resists. Positive resist materials include polymethyl-methacrylate (PMMA) and two component diazoquinone/phenolic resin materials. See, e.g., "Introduction to microlithography", Thompson (47).

The coated laminate is irradiated through a photomask 166 imprinted with a pattern corresponding in size and layout to the desired pattern of the microchannel. Methods for forming photomask having desired photomask patterns are well known. For example, the mask can be prepared by printing the desired layout on an overhead transparency using a high resolution (3000 dpi) printer. Exposure is carried out on standard equipment such as a Karl Sass contact lithography machine.

Figure 7A:
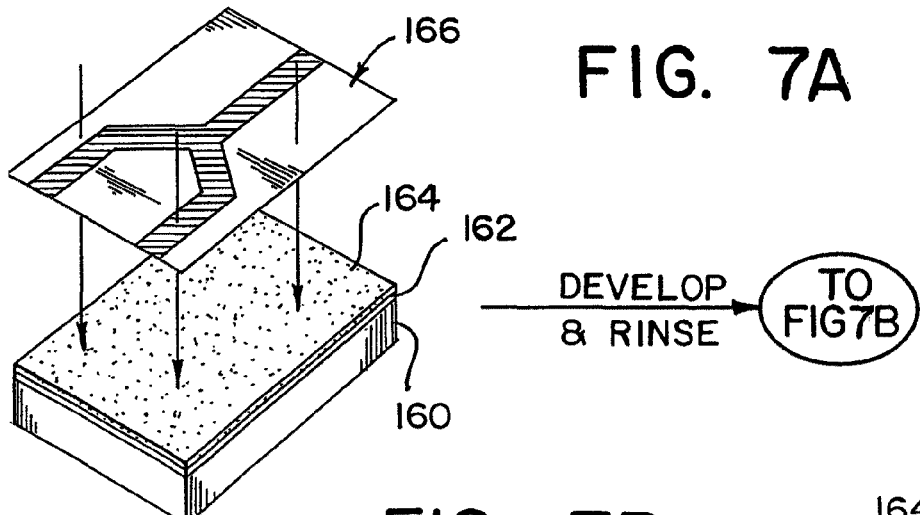
FIGS. 7A-7D show initial steps in photolithographic microfabrication of a nucleic acid sorting device from a silicon wafer, using photolithography and several stages of etching.
Figure 7B:
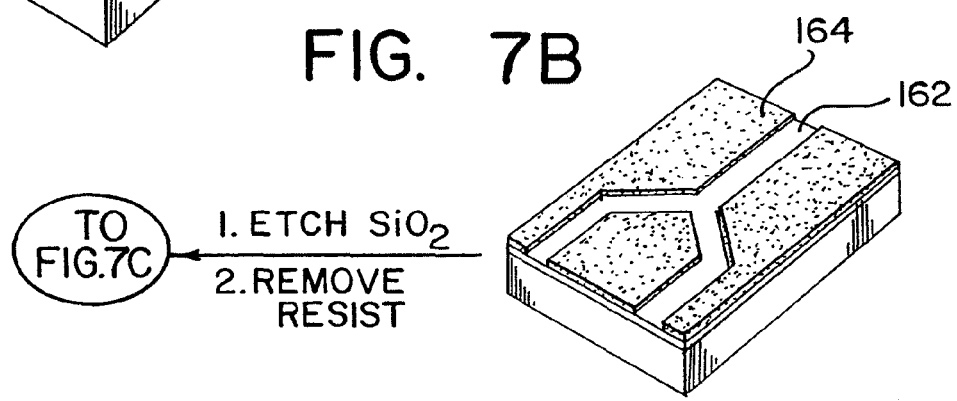
Figure 7C:
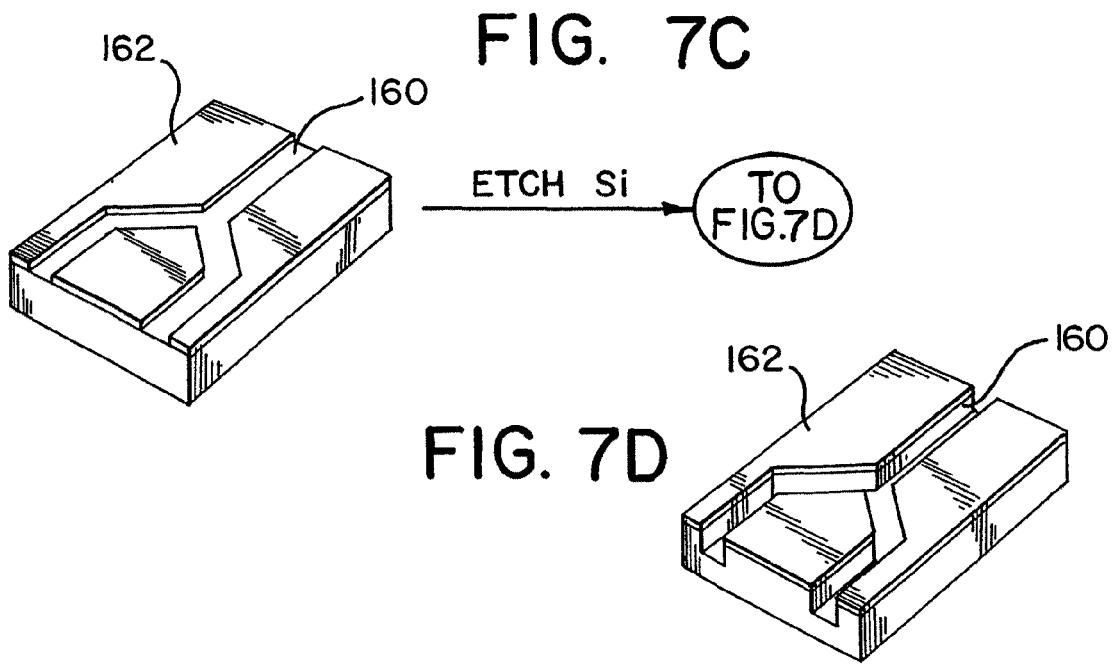
Figure 7D:
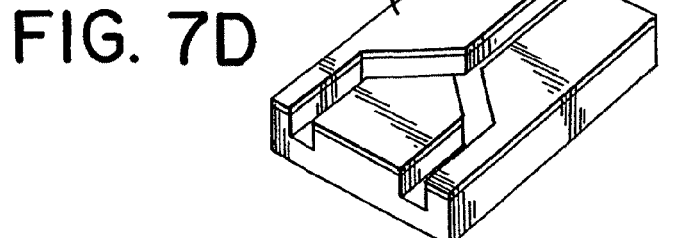

In the method illustrated in FIGS. 7A-5D, the photoresist is a negative resist, meaning that exposure of the resist to a selected wavelength, e.g., UV, light produces a chemical change that renders the exposed resist material resistant to the subsequent etching step. Treatment with a suitable etchant removes the unexposed areas of the resist, leaving a pattern of bare and resist-coated silicon oxide on the wafer surface, corresponding to the layout and dimensions of the desired micro structures. In this example, because a negative resist was used, the bare areas correspond to the printed layout on the photomask. The wafer is now treated with a second etchant material, such as a reactive ion etch. (R.E.), effective to dissolve the exposed areas of silicon dioxide. The remaining resist is removed, typically with hot aqueous $H_2SO_4$. The remaining pattern of silicon dioxide (162) now serves as a mask for the silicon (160). The channels are etched in the unmasked areas of the silicon substrate by treating with a KO etching solution. Depth of etching is controlled by time of treatment. Additional microcomponents may also be formed within the channels by further photolithography and etching steps, as discussed below.

Depending on the method to be used for directing the flow of molecules through the device, electrodes and/or valves are fabricated into the flow channels. A number of different techniques are available for applying thin metal coatings to a substrate in a desired pattern. These are reviewed in, for example, Krutenat, Kirk-Othmer 3rd ed., Vol. 15, pp. 241-274 (43), incorporated herein by reference. A convenient and common technique used in fabrication of microelectronic circuitry is vacuum deposition. For example, metal electrodes or contacts may be evaporated onto a substrate using vacuum deposition and a contact mask made from, e.g., a "MYLAR" sheet. Various metals such as platinum, gold, silver or indium/tin oxide (ITO) may be used for the electrodes.

Deposition techniques allowing precise control of the area of deposition are preferred for application of electrodes to the side walls of the channels in the device. Such techniques are described, for example, in Krutenat (43), above, and references cited therein. They include plasma spraying, where a plasma gun accelerates molten metal particles in a carrier gas towards the substrate, and physical vapor deposition using an electron beam, where atoms are delivered on line-of-sight to the substrate from a virtual point source. In laser coating, a laser is focused onto the target point on the substrate, and a carrier gas projects powdered coating material into the beam, so that the molten particles are accelerated toward the substrate.

Another technique allowing precise targeting uses an electron beam to induce selective decomposition of a previously deposited substance, such as a metal salt, to a metal. This technique has been used to produce sub-micron circuit paths (e.g., 37).

6.9. Elastomeric Microfabricated Device

This Example demonstrates the manufacture of a disposable microfabricated device, which can function as a stand-alone device or as a component of an integrated microanalytical chip, in sorting molecules or cells. In particular, this example describes exemplary microfluidic devices that are manufactured from an elastomer material (e.g., a silicone elastomer). Other elastomer materials that may be used include silicone elastomers such as polydimethylsiloxane (PDMS) (see, e.g., Subsection 6.12.1, infra). Such materials are particularly preferred in embodiments, e.g., wherein the features of a microfluidic device (e.g., channel widths and depths, valves and pumps, etc.) have sizes that approach or are below the limits of optical diffraction and are therefore smaller than can be obtained through traditional optical lithography techniques.

Micrometer or nanometer scale microfluidic devices may be readily microfabricated with such materials, e.g., using the replica molding or "soft lithography" techniques described herein and by Xia and Whitesides (24). However, other microfabrication techniques are also known in the art and may be used to fabricate microfluidic devices of this invention; e.g., "nano-imprint lithography" techniques (86, 87). Additional materials and methods that can be used to manufacture microfluidic devices of this invention are disclosed in U.S. Provisional Patent Application Ser. No. 60/249,362, filed Nov. 16, 2000 and incorporated herein, by reference, in its entirety.

6.9.1. Preparation of the Microfabricated Device

A silicon wafer was etched and fabricated as described above and in (27). After standard contact photolithography techniques to pattern the oxide surface of the silicon wafer, a $C_2F_2/CHF_3$ gas mixture was used to etch the wafer by R.E. The silicon wafer was then subjected to further etch with KO to expose the silicon underneath the oxide layer, thereby forming a mold for the silicone elastomer. The silicon mold forms a "T" arrangement of channels. The dimensions of the channels may range broadly, having approximately 5×4 µm dimension.

Figure 8:
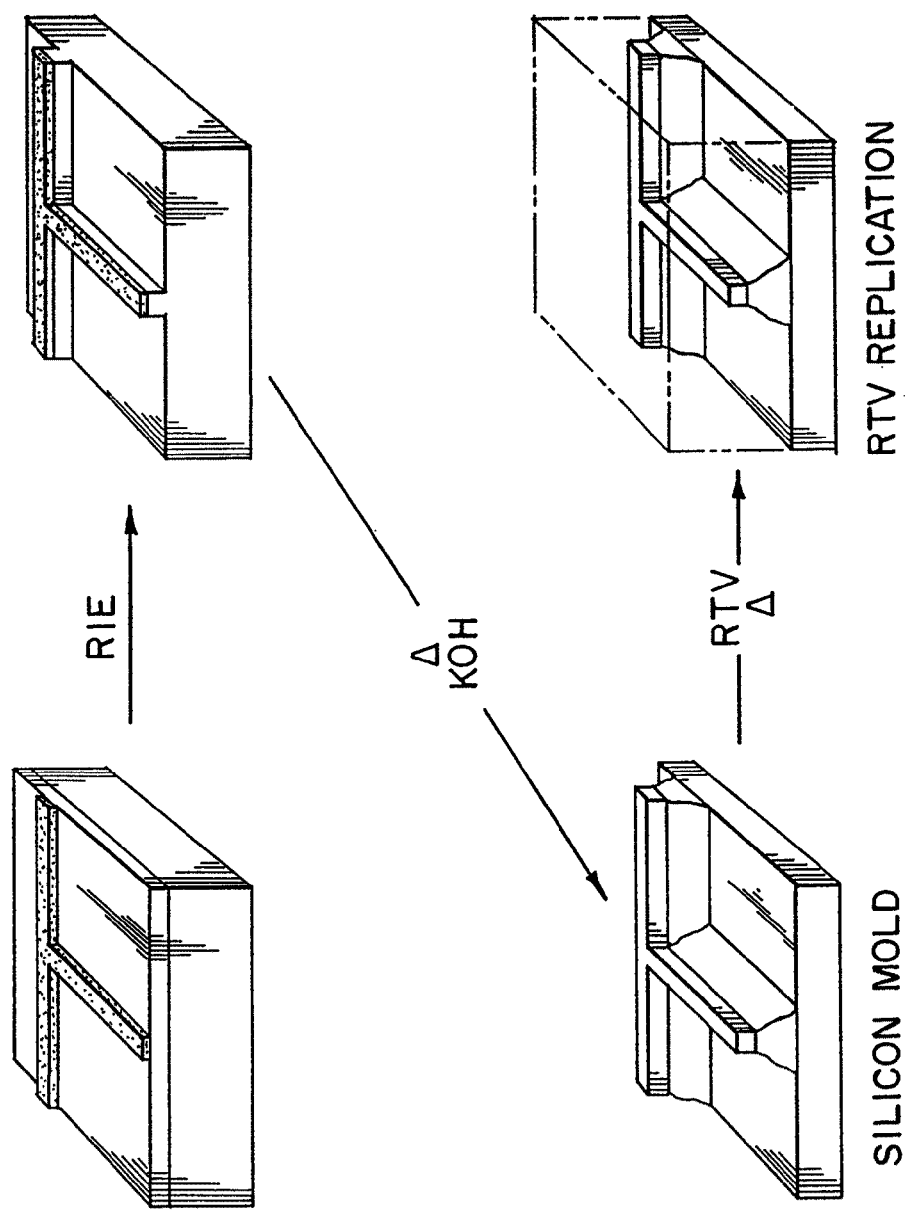
FIG. 8 shows a schematic representation of a process for obtaining a silicone elastomer impression of a silicon mold to provide a microfabricated chip according to the invention.

The etching process is shown schematically in FIG. 8. Standard micromachining techniques were used to create a negative master mold out of a silicon wafer. The disposable silicone elastomer chip was made by mixing General Electric RTV 615 components (32) together and pouring onto the etched silicon wafer. After curing in an oven for 2 hours at 80° C., the elastomer was peeled from the wafer and bonded hermetically to a glass cover slip for sorting. To make the elastomer hydrophilic the elastomer chip was immersed in HCl (pH=2.7) at 60 degrees C. for 40 to 60 min. Alternatively, the surface could have been coated with polyurethane (3% w/v in 95% ethanol and diluted 10× in ethanol). It is noted that the master wafer can be reused indefinitely. The device shown has channels that are 100 µm wide at the wells, narrowing to 3 µm at the sorting junction (discrimination region). The channel depth is 4 µm, and the wells are 2 mm in diameter. These dimensions can be modified according to the size range of the molecules or cells to be analyzed or sorted.

6.9.2. Detection Apparatus

Figure 9:
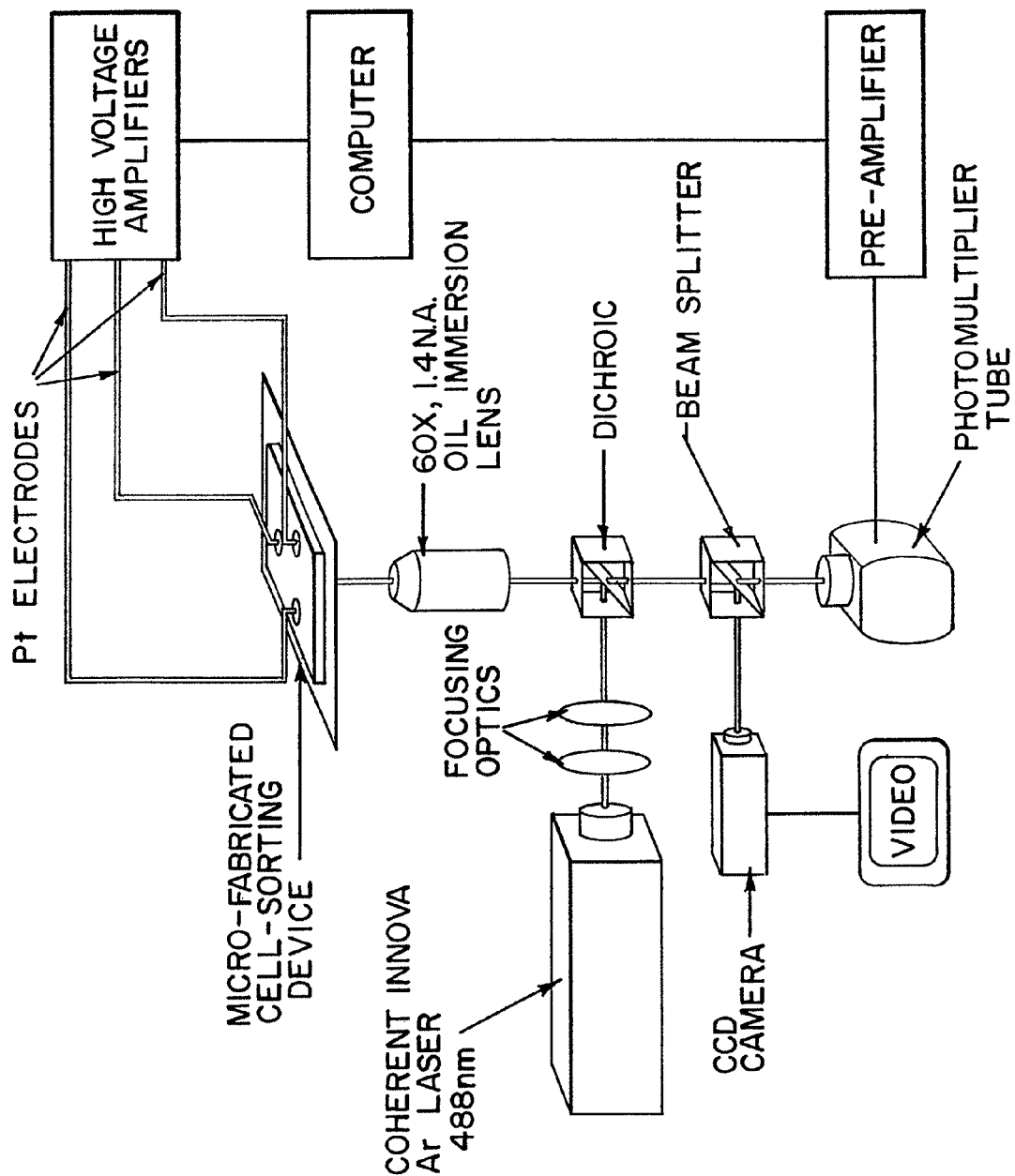
FIG. 9 shows a schematic representation of an apparatus of the invention, in which a silicone elastomer chip is mounted on an inverted microscope for optical detection of a laser-stimulated reporter. Electrodes are used to direct cells in response to the microscope detection.
Figure 10:
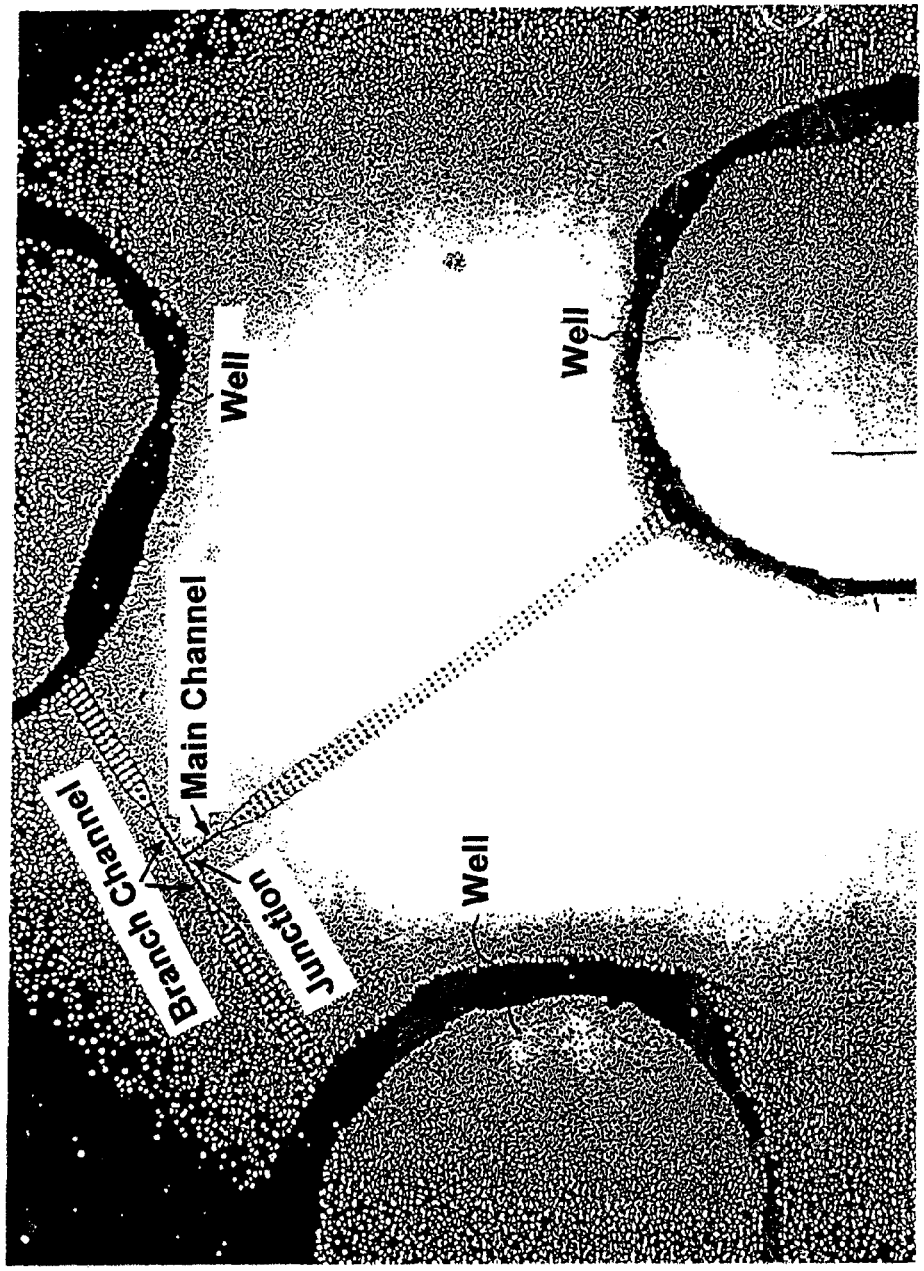
FIG. 10 is a photograph of an apparatus of the invention, showing a chip with an inlet channel and reservoir, a detection region, a branch point, and two outlet channels with reservoirs.

In this embodiment the device was mounted on an inverted optical microscope (Zeiss Axiovert 35) as shown in FIG. 9. In this system, the flow control can be provided by voltage electrodes for electro-osmotic control or by capillaries for pressure-driven control. The detection system can be photomultiplier tubes or photodiodes, depending upon the application. The inlet well and two collection wells were incorporated into the elastomer chip on three sides of the "T" forming three channels (FIG. 7). The chip was adhered to a glass coverslip and mounted onto the microscope.

6.10. Operation of a Microfabricated Polynucleotide Analysis Device

The operation of a polynucleotide analysis chip is described. This example refers to polynucleotides, but it will be appreciated that other molecules may be analyzed or sorted using similar methods and devices. Likewise, cells can be processed using similar methods and devices, adapted to the appropriate size.

A solution of reporter-labeled polynucleotides is prepared as described below and introduced into the sample inlet end(s) of the analysis unit(s). The solution may be conveniently introduced into a reservoir, such as reservoir 48 of FIG. 1, via a port or connector, such as connector 70 in FIG. 2, adapted for attachment to a segment of tubing, such as liquid chromatography or HPLC tubing.

It is typically advantageous to "hydrate" the device (i.e., fill the channels of the device with the solvent, e.g., water or a buffer solution, in which the polynucleotides will be suspended) prior to introducing the polynucleotide-containing solution. Such hydrating can be achieved by supplying water or the buffer solution to the device reservoir and applying hydrostatic pressure to force the fluid through the analysis unit(s).

Following such hydration, the polynucleotide-containing solution is introduced into the sample inlets of the analysis unit(s) of the device. As the stream of labeled polynucleotides (e.g., tagged with a reporter such as a fluorescent dye) is passed in a single file manner through the detection region, the optical signal (e.g., fluorescence) from the optically-detectable reporter moieties on each molecule are quantitated by an optical detector and converted into a number used in calculating the approximate length of polynucleotide in the detection region.

Exemplary reporter moieties, described below in reference to sample preparation, include fluorescent moieties which can be excited to emit light of characteristic wavelengths by an excitation light source. Fluorescent moieties have an advantage in that each molecule can emit a large number of photons (e.g., upward of 106) in response to exciting radiation. Suitable light sources include lasers, laser diodes, high-intensity lamps, e.g., mercury lamps, and the like. In embodiments where a lamp is used, the channels are preferably shielded from the light in all regions except the detection region, to avoid bleaching of the label. In embodiments where a laser is used, the laser can be set to scan across a set of detection regions from different analysis units. Other optically-detectable reporter moieties include chemiluminescent moieties, which can be used without an excitation light source.

Where laser diodes are used as a light source, the diodes may be microfabricated into the same chip that contains the analysis units. Alternatively, the laser diodes may be incorporated into a second chip (laser diode chip; LDC) that is placed adjacent to the chip such that the laser light from the diodes shines on the detection regions. The photodiodes in the LDC are preferably placed at a spacing that corresponds to the spacing of the detection regions in the chip.

The level of reporter signal is measured using an optical detector, such as a photodiode (e.g., an avalanche photodiode), a fiber-optic light guide leading, e.g., to a photomultiplier tube, a microscope with a high numerical aperture (N.A.) objective and an intensified video camera, such as a SIT camera, or the like. The detector may be microfabricated or placed into the PAC itself (e.g., a photodiode as illustrated in FIGS. 3A and 3B), or it may be a separate element, such as a microscope objective.

In cases where the optical detector is a separate element, it is generally necessary to restrict the collection of signal from the detection region of a single analysis unit. It may also be advantageous to scan or move the detector relative to the polynucleotide analysis unit ("PAC"), preferably by automation. For example, the PAC can be secured in a movable mount (e.g., a motorized/computer-controlled micromanipulator) and scanned under the objective. A fluorescence microscope, which has the advantage of a built-in excitation light source (epifluorescence), is preferably employed for detection of a fluorescent reporter.

Since current microfabrication technology enables the creation of sub-micron structures employing the elements described herein, the dimensions of the detection region are influenced primarily by the size of the molecules under study. These molecules can be rather large by molecular standards. For example, lambda DNA (~50 kb) in solution has a diameter of approximately 0.5 µm. Accordingly, detection regions used for detecting polynucleotides in this size range have a cross-sectional area large enough to allow such a molecule to pass through without being substantially slowed down relative to the flow of the solution carrying it and causing a "bottle neck". The dimensions of a channel should thus be at least about twice, preferably at least about five times as large per side or in diameter as the diameter of the largest molecule that will be passing through it.

Another factor important to consider in the practice of the invention is the optimal concentration of polynucleotides in the sample solution, particularly in embodiments which process or analyze one molecule or cell at a time. The concentration should be dilute enough so that a large majority of the polynucleotide molecules pass through the detection region one by one, with only a small statistical chance that two or more molecules pass through the region simultaneously. This is to insure that for the large majority of measurements, the level of reporter measured in the detection region corresponds to a single molecule, rather than two individual molecules.

The parameters which govern this relationship are the volume of the detection region and the concentration of molecules in the sample solution. The probability that the detection region will contain two or more molecules ($P_{\geq 2}$) can be expressed as $$P_{\geq 2} = 1 - \{1 + [DNA]*V\} * e^{-[DNA]*V}$$

where [DNA] is the concentration of polynucleotides in units of molecules per $\mu m^3$ and V is the volume of the detection region in units of $\mu m^3$.

It will be appreciated that $P_{\geq 2}$ can be minimized by decreasing the concentration of polynucleotides in the sample solution. However, decreasing the concentration of polynucleotides in the sample solution also results in increased volume of solution processed through the device and can result in longer run times. Accordingly, the objectives of minimizing the simultaneous presence of multiple molecules in the detection chamber (to increase the accuracy of the sorting) needs to be balanced with the objective of generating a sorted sample in a reasonable time in a reasonable volume containing an acceptable concentration of polynucleotide molecules.

The maximum tolerable $P_{\geq 2}$ depends on the desired "purity" of the sorted sample. The "purity" in this case refers to the fraction of sorted polynucleotides that are in the specified size range, and is inversely proportional to $P_{\geq 2}$.

For example, in applications where high purity is not required, such as the purification of a particular restriction fragment from an enzymatic digest of a portion of vector DNA, a relatively high $P_{\geq 2}$ (e.g., $P_{\geq 2}$=0.2) may be acceptable. For most applications, maintaining $P_{\geq 2}$ at or below about 0.1 provides satisfactory results.

In an example where $P_{\geq 2}$ is equal. 0.1, it is expected that in about 10% of measurements, the signal from the detection region will be due to the presence of two or more polynucleotide molecules. If the total signal from these molecules is in the range corresponding to the desired size fragment, these (smaller) molecules will be sorted into the channel or tube containing the desired size fragments.

The DNA concentration needed to achieve a particular value $P_{\geq 2}$ in a particular detection volume can be calculated from the above equation. For example, a detection region in the shape of a cube 1 $\mu m^3$ per side has a volume of 1 femtoliter (fl). A concentration of molecules resulting, on average, in one molecule per fl, is about 1.7 nM. Using a $P_{\geq 2}$ of about 0.1, the polynucleotide concentration in a sample analyzed or processed using such a 1 fl detection region volume is approximately 0.85 nM, or roughly one DNA molecule per 2 detection volumes ([DNA]*V=~0.5). If the concentration of DNA is such that [DNA]*V is 0.1, $P_{\geq 2}$ is less than 0.005; i.e., there is less than a one half of one percent chance that the detection region will at any given time contain two of more fragments.

The signal from the optical detector is routed, e.g., via electrical traces and pins on the chip, to a processor, which processes the signals into values corresponding to the length of the polynucleotide giving rise to the signal. These values are then compared, by the processor, to pre-loaded instructions containing information on which branch channel molecules of a particular size range will be routed into. Following a delay period that allows the molecule from which the reporter signal originated to arrive at the discrimination region, the processor sends a signal to actuate the active elements in the discrimination region such that the molecule is routed into the appropriate branch channel.

The delay period is determined by the rate at which the molecules move through the channel (their velocity relative to the walls of the channel) and the length of the channel between the detection region and the discrimination region. In cases where the sample solution is moved through the device using hydrostatic pressure (applied, e.g., as pressure at the inlet end and/or suction at the outlet end), the velocity is typically the flow rate of the solution. In cases where the molecules are pulled through the device using some other means, such as via electro-osmotic flow with an electric field set up between the inlet end and the outlet end, the velocity as a function of molecule size can be determined empirically by running standards, and the velocity for a specific molecule calculated based on the size calculated for it from the reporter signal measurement.

A relevant consideration with respect to the velocity at which the polynucleotide molecules move through the device is the shear force that they may be subject to. At the channel dimensions contemplated herein, the flow through the channels of the device is primarily laminar flow with an approximately parabolic velocity profile. Since the cross-sectional area of the channels in the device can be on the same order of magnitude as the diameter of the molecules being analyzed, situations may arise where a portion of a particular molecule is very near the wall of the channel, and is therefore in a low-velocity region, while another portion of the molecule is near the center of the channel, i.e., in a high-velocity region. This situation creates a shear force (F) on the molecule, which can be estimated using the following expression:

$$F = 6\pi\eta R_\lambda V$$

where $R_\lambda$ is the radius of the molecule and $\eta$ is the viscosity of the solution. This expression assumes that the molecule is immobilized on a stationary surface and subject to uniform flow of velocity V.

The amount of force necessary to break a double stranded fragment of DNA is approximately 100 pN. Accordingly, the maximal shear force that the molecules are subjected to should preferably be kept below this value. Substituting appropriate values for the variables in the above expression for lambda DNA yields a maximum velocity of about 1 cm/sec for a channel 1 $\mu m$ in radius (i.e., a channel of a dimension where one portion of the lambda molecule can be at or near the wall of the channel with the opposite side in the center of the channel). Since devices designed for use with such large molecules will typically have channels that are considerably larger in diameter, the maximum "safe" velocity will typically be greater than 1 cm/sec.

As discussed above, the sample solution introduced into a device of the invention should be dilute enough such that there is a high likelihood that only a single molecule occupies the detection region at any given time. It follows then that as the solution flows through the device between the detection and discrimination regions, the molecules will be in "single file" separated by stretches of polynucleotide-free solution. The length of the channel between the detection and discrimination region should therefore not be so long as to allow random thermal diffusion to substantially alter the spacing between the molecules. In particular, the length should be short enough that it can be traversed in a time short enough such that even the smallest molecules being analyzed will typically not be able to diffuse and "switch places" in the line of molecules.

The diffusion constant of a 1 kb molecule is approximately 5 µm²/sec; the diffusion equation gives the distance that the molecule diffuses in time t as $$<X^2> \sim Dt$$

Using this relationship, it can be appreciated that a 1 kbp fragment takes about 0.2 seconds to diffuse 1 µm. The average spacing of molecules in the channel is a function of the cross-sectional area of the channel and the molecule concentration, the latter being typically determined in view of acceptable values of $P_{\geq 2}$ (see above). From the above relationships, it is then straightforward to calculate the maximum channel length between the detection and discrimination region which would ensure that molecules don't "switch places". In practice, the channel length between the detection and discrimination regions is between about 1 µm and about 2 cm.

As illustrated above with respect to FIGS. 5A-D, there are a number of ways in which molecules can be routed or sorted into a selected branch channel. For example, in a device employing the discrimination region shown in FIG. 4A, the solution is preferably moved through the device by hydrostatic pressure. Absent any field applied across electrodes 110 and 112, a molecule would have an equal probability of entering one or the other of the two branch channels 106 and 108. The sorting is accomplished by the processor temporarily activating a voltage source connected to the electrode leads 114 and 116 just before or at the time the molecule to be routed enters the junction of the main channel and the two branch channels. The resulting electric field exerts a force on the negatively-charged DNA molecule biasing it toward the positively-charged electrode. The molecule will then be carried down the branch channel containing the positively-charged electrode by the bulk solution flow. The electric field is turned off when the molecule has committed itself to the selected channel. As soon as the molecule clears the corner from the discrimination region and into the branch channel, it escapes effects of the electric field that will be applied to the next molecule in the solution stream.

The discrimination region shown in FIG. 5B is designed for use in a device that employs electroosmotic flow, rather than flow induced by hydrostatic pressure, to move both the polynucleotides and bulk solution through the device. Electrodes are set up in the channels at the inlet and outlet ends of the device. Application of an electric field at the ends of the channels (with electrode 130 being negative, and electrodes 132 and 134 being positive) sets up bulk solution flow according to well-established principles of electroosmotic flow (see, e.g., 36). When a specific polynucleotide molecule enters the junction region between the main channel and the two branch channels, the voltage to one of either electrodes 132 or 134 is shut off, leaving a single attractive force, acting on the solution and the DNA molecule, into the selected branch channel. As above, both branch channel electrodes are activated after the molecule has committed to the selected branch channel in order to continue bulk flow through both channels.

In another embodiment of the invention the polynucleotides are directed into a selected branch channel via a valve in the discrimination region. An exemplary valve is shown in FIG. 5C. The valve consists of a thin extension of material 140 which can be charged via an electrode 142. The extension can then be deflected to close one or the other of the branch channels by application of an appropriate voltage across electrodes 144 and 146. As above, once the molecule has committed, the voltage can be turned off.

In a device in which the sample solution is moved through the device by application of positive pressure at the sample inlet end(s) of the analysis unit(s), the discrimination function may be affected by simply blocking branch channel sample outlets into which the sample is not supposed to go, and leaving the selected outlet open. Due to the small size scale of the channels and the incompressibility of liquids, blocking the solution flow creates an effective "plug" in the unselected branch channels, routing the molecule along with the bulk solution flow into the selected channel. This embodiment is illustrated in FIG. 4D. It can be achieved by, for example, incorporating valve structures downstream of the discrimination region.

Alternatively, the discrimination function may be affected by changing the hydrostatic pressure at the sample outlets of the branch channels into which the sample is not supposed to go. Specifically, if the branch channels in a particular analysis unit all offer the same resistance to fluid flow, and the pressure at the sample inlet of the main channel of an analysis unit is P, then the fluid flow out of any selected branch channel can be stopped by applying a pressure P/n at the sample outlet of that branch channel, where n is the number of branch channels in that analysis unit. Accordingly, in an analysis unit having two branch channels, the pressure applied at the outlet of the branch to be blocked is P/2.

It will be appreciated that the position and fate of the molecules in the discrimination region can be monitored by additional detection regions installed, e.g., immediately upstream of the discrimination region and/or in the branch channels immediately downstream of the branch point. This information be used by the processor to continuously revise estimates of the velocity of the molecules in the channels and to confirm that molecules having selected size characteristics end up in the selected branch channel.

Solution from the branch channels is collected at the outlet ends of the analysis units. As described above, devices with a plurality of analysis units typically collect the solution from corresponding branch channels of each unit into a manifold, which routes the solution flow to an outlet port, which can be adapted for receiving, e.g., a segment of tubing or a sample tube, such as a standard 1.5 ml centrifuge tube.

The time required to isolate a desired quantity of polynucleotide depends on a number of factors, including the size of the polynucleotide, the rate at which each analysis unit can process the individual fragments, and the number of analysis units per chip, and can be easily calculated using basic formulas. For example, a chip containing 1000 analysis units, each of which can sort 1000 fragments per second, could isolate 0.1 µg of 10 kb DNA in about 2.5 hours.

6.11. Other Microfabricated Devices of the Invention

Operation of a microfabricated cell sorting device is essentially as described above with respect to the polynucleotide sorting device. Since cells typically do not have predictable a net charge, the directing means are preferably ones employing a valve in the discrimination region as described above, or flow stoppage, either by valve or hydrostatic pressure.

Operation of a microfabricated analysis device is accomplished essentially as is described above, except that functions relating to sorting polynucleotide molecules into branch channels don't need to be performed. The processor of such analysis devices is typically connected to a data storage unit, such as computer memory, hard disk or the like, as well as to a data output unit, such as a display monitor, printer and/or plotter. The sizes of the polynucleotide molecules passing through the detection region are calculated and stored in the data storage unit. This information can then be further processed and/or routed to the data output unit for presentation as, e.g., histograms of the size distribution of DNA molecules in the sample. The data can, of course, be presented in real time as the sample is flowing through the device, allowing the practitioner of the invention to continue the run only as long as is necessary to obtain the desired information.

In preferred molecular (e.g. DNA, polynucleotide or polypeptide) analysis and sorting embodiments, a microfabricated chip of the invention has a detection volume of about 10 to about 5000 femtoliters (fl), preferably about 50 to about 1000 fl, and most preferably on the order of about 200 fl. In preferred cell analysis and sorting embodiments, a microfabricated chip of the invention has a detection volume of approximately 1 to 1,000,000 femtoliters (fl), preferably about 200 to 500 fl and most preferably about 375 fl.

6.12. Exemplary Embodiment and Additional Parameters

6.12.1. Microfluidic Chip Fabrication

In a preferred embodiment, the invention provides a "T" on "Y" shaped series of channels molded into optically transparent silicone rubber or PolyDiMethylSiloxane (PDMS), preferably PDMS. This is cast from a mold made by etching the negative image of these channels into the same type of crystalline silicon wafer used in semiconductor fabrication. As described above, the same techniques for patterning semiconductor features are used to form the pattern of the channels. The uncured liquid silicone rubber is poured onto these molds placed in the bottom of a Petri dish. To speed the curing, these poured molds are baked. After the PDMS has cured, it is removed from on top of the mold and trimmed. In a chip with one set of channels forming a "T", three holes are cut into the silicone rubber at the ends of the "T", for example using a hole cutter similar to that used for cutting holes in cork, and sometimes called cork borers. These holes form the sample, waste and collection wells in the completed device. In this example, the hole at the bottom end of the T is used to load the sample. The hole at one arm of the T is used for collecting the sorted sample while the opposite arm is treated as waste. Before use, the PDMS device is placed in a hot bath of HCl to make the surface hydrophilic. The device is then placed onto a No. 1 (150 μm thick) (25×25 mm) square microscope cover slip. The cover slip forms the floor (or the roof) for all three channels and wells. The chip has a detection region as described above.

Note that any of or all of these manufacturing and preparation steps can be done by hand, or they can be automated, as can the operation and use of the device.

The above assembly is placed on an inverted Zeiss microscope. A carrier holds the cover slip so that it can be manipulated by the microscope's x-y positioning mechanism. This carrier also has mounting surfaces which support three electrodes, which implement the electro-osmotic and/or electrophoretic manipulation of the cells or particles to be analyzed and sorted. The electrodes are lengths of platinum wire taped onto a small piece of glass cut from a microscope slide. The wire is bent into a hook shape, which allows it to reach into one of the wells from above. The cut glass acts as a support platform for each of the electrodes. They are attached to the custom carrier with double-sided tape. This allows flexible positioning of the electrodes. Platinum wire is preferred for its low rate of consumption (long life) in electrophoretic and electro-osmotic applications, although other metals such as gold wire may also be used.

6.12.2. Device Loading

To operate the device for sorting, one of the wells, e.g. the collection or waste well, is first filled with buffer. All three channels, starting with the channel, connected to the filled well, wick in buffer via capillary action and gravity. Preferably, no other well is loaded until all the channels fill with buffer, to avoid the formation of air pockets. After the channels fill the remaining wells can be loaded with buffer, as needed, to fill or equilibrate the device. The input or sample well is typically loaded last so that the flow of liquid in the channels is initially directed towards it. Generally, equal volumes of buffer or sample are loaded into each well. This is done in order to prevent a net flow of liquid in any direction once all of the wells are loaded, including loading the sample well with sample. In this embodiment, it is preferred that the flow of material through the device (i.e. the flow of sample) be driven only by the electrodes, e.g. using electro-osmotic and/or electrophoretic forces. The electrodes may be in place during loading, or they can be placed into the wells after loading, to contact the buffer.

6.12.3. Electrodes

Two of the above electrodes are driven by high voltage operational amplifiers (op-amps) capable of supplying voltages of +−150 V. The third electrode is connected to the electrical ground (or zero volts) of the high voltage op-amp electronics. For sorting operation the driven electrodes are placed in the collection and waste wells. The ground electrode is placed in the sample well. The op-amps amplify, by a factor of 30, a control voltage generated by two digital to analog converters DACs). The maximum voltage these DACs generate is +−5 V, which determines the amplification factor of 30. The 150 V limit is determined by the power supply to the amplifiers, which are rated for +−175 V. These DACs reside on a card (a Lab PC 1200 Card, available from National Instruments, Austin, Tex.) mounted in a personal computer. The card also contains multiple channels of analog to digital converters (ADC's) one of which is used for measuring the signal generated by photomultiplier tubes (PMTs). This card contains two DACs. A third DAC can be used to drive the third electrode with an additional high voltage op amp. This would provide a larger voltage gradient, if desired, and some additional operational flexibility.

Without being bound by any theory, it is believed that the electrodes drive the flow of sample through the device using electro-osmotic or electrophoretic forces, or both. To start the movement of molecules, cells or particles to be sorted, a voltage gradient is established in the channels. This is done by generating a voltage difference between electrodes.

In this example, the voltage of the two driven electrodes is raised or lowered with respect to the grounded electrode. The voltage polarity depends on the charge of the molecules, cells or particles to be sorted (if they are charged), on the ions in the buffer, and on the desired direction of flow. Because the electrode at the sample well in the examples is always at zero volts with respect to the other two electrodes, the voltage at the "T" intersection or branch point will be at a voltage above or below zero volts, whenever the voltage of the other two electrodes is raised or lowered. Typically, the voltage is set or optimized, usually empirically, to produce a flow from the sample well, toward a downstream junction or branch point where two or more channels meet In this example, where two channels are used, one channel is typically a waste channel and terminates in a waste well, the other channel is a collection channel and terminates in a collection well.

To direct the molecules, particles or cells to a particular channel or arm of the "T" (e.g. collection or waste), the voltage at the electrode in one well (or multiple wells, in multi-channel embodiments) is made the same as the voltage at the junction or branch point, where the channels meet. The voltage of the electrode at one well (of the two or more wells is raised or lowered, to produce a gradient between that well and the branch point. This causes the flow to move down the channel towards and into the well, in the direction produced by the gradient. Typically, the voltage of the electrode at the waste well is raised or lowered with respect to the voltage at the collecting well, to direct the flow into the waste channel and the waste well, until a molecule, particle or cell is identified for collection. The flow is diverted into the collection channel and collection well by adjusting the voltages at the electrodes to eliminate or reduce the gradient toward the waste well, and provide or increase the gradient toward the collection well. For example, in response to a signal indicating that a molecule or cell has been detected for sorting, by examination in a detection region upstream of the branch point, the voltage at the waste and collection points can be switched, to divert the flow from one channel and well to the other.

The voltage at the branch point (the intersection voltage) is determined by the voltage gradient desired (e.g. Volts/mm) times the distance from the sample well electrode to the branch point (gradient×distance), which in this example is placed where all of the channels of the "T" intersect. The gradient also determines the voltage at the waste or collection electrode (gradient×distance from sample well to collection well).

Conceptually, the channels and wells of the "T" can be treated as a network of three resistors. Each segment of the "T" behaves as a resistor whose resistance is determined by the conductivity of the buffer and the dimensions of the channel. A voltage difference is provided across two of the resistors, but not the third. If the electrodes in each of the three wells is equidistant from the branch point, then each channel will have the same resistance.

For example, assume that each section of the "T" has 100 K ohms of resistance. If 100 volts is applied across two of the resistors and the third resistor is left unconnected, the current at the junction of the two resistors would be 50 volts. If a voltage source of 50 volts is connected to the end of the third resistor, the voltage at the junction does not change. That is, a net of zero volts is established across the third resistor; there is no voltage gradient and a flow is not initiated or changed. If a different voltage is applied, a gradient can be established to initiate or direct the flow into one channel or another. For example, to change the direction of flow from one arm of the "T" to the other, the voltage values of the two driven electrodes are swapped. The junction voltage remains the same. If the electrode distances from the "T" intersection are not equal, then the voltages can be adjusted to accommodate the resulting differences in the effective channel resistance. The end result is still the same. The electrode in the well of the channel which is temporarily designated not to receive particles or cells is set at the voltage of the "T" intersection. The voltage at the other driven electrode is set to provide a gradient that directs molecule, cell or particle flow into that well. Thus, cells or particles can be sent down one channel or another, and ultimately into one well or another, by effectively opening one channel with a net or relative voltage gradient while keeping the other channel or channels closed by a net or relative voltage gradient of zero.

In a preferred embodiment for sorting according to the invention, a slight flow down the channel that is turned "off" is desired. This keeps the molecules or cells moving away from the branch point (the "T" junction), particularly those which have already been directed to that channel. Thus, a small non-zero gradient is preferably established in the "off" or unselected channel. The selected channel is provided with a significantly higher gradient, to quickly and effectively divert the desired molecules or cells into that channel.

The placement of the wells and their electrodes with respect to the branch point, and in particular their distance from the branch point, is an important factor in driving the flow of molecules or cells as desired. As the wells and electrodes are brought closer to the branch point, it becomes more important to precisely place the electrodes, or precisely adjust the voltages.

6.12.4. Detection Optics

In this example, a Ziess Axiovert 35 inverted microscope is used for detection of molecules or cells for sorting. The objective lens of this microscope faces up, and is directed at the detection region of the described microfluidic chip, through the coverslip which in this example is the floor of the device. This microscope contains all the components for epifluorescence microscopy. See, Inoue pp 67-70, 91-97 (63). In this embodiment a mercury arc lamp or argon ion laser is used as the light source. The mercury lamp provides a broad spectrum of light that can excite many different fluorophores. The argon ion laser has greater intensity, which improves the detection sensitivity but is generally restricted to fluorophores that excite at 488 or 514 nm. The mercury lamp is used, for example, to sort beads as described elsewhere herein. The laser is used for sorting GFP *E. coli* bacterial cells as described elsewhere herein. The high power argon ion beam is expanded to fill the illumination port of the microscope, which matches the optical characteristics of the mercury arc lamp and provides a fairly uniform illumination of the entire image area in a manner similar to the mercury lamp. However, it is somewhat wasteful of the laser light. If a lower powered laser is used, the laser light is focused down to coincide with the detection region of the chip, to achieve the same or similar illumination intensity and uniformity with less power consumption.

The objective used in the example is an Olympus PlanApo 60x 1.4 N.A oil immersion lens. The optics are of the infinity corrected type. An oil immersion lens enables collecting a substantial percentage of the 180 degree hemisphere of emitted light from the sample. This enables some of the highest sensitivity possible in fluorescence detection. This microscope has 4 optical ports including the ocular view port. Each port, except the ocular, taps ~20% of the available light collected from the sample when switched into the optical path. Only the ocular port can view 100% of the light collected by the objective. In this embodiment, a color video camera is mounted on one port, another has a Zeiss adjustable slit whose total light output is measured with a photomultiplier tube (PMT). The fourth port is not used.

The microscope focuses the image of the sample onto the plane of the adjustable slit. An achromatic lens collimates the light from the slit image onto the active area of the PMT. Immediately in front of the PMT window an optical band pass filter is placed specific to the fluorescence to be detected. The PMT is a side on-type and does not have a highly uniform sensitivity across its active area. By relaying the image to the PMT with the achromat, this non-uniformity is averaged and its effect on the measured signal is greatly minimized. This also enables near ideal performance of the bandpass filter. A 20% beam splitter has been placed in the light path between the achromat and filter. An ocular with a reticle re-images this portion of the collimated light. This enables viewing the adjustable slit directly, to insure that the detection area that the PMT measures is in focus and aligned. The adjustable slit allows windowing a specific area of the channel for detection. Its width, height, and x,y position are adjustable, and conceptually define a detection region on the chip. In this embodiment, the microscope is typically set to view a 5 μm (micron) length of the channel directly below the "T" intersection.

The PMT is a current output device. The current is proportional to the amount of light incident on the photocathode. A transimpedance amplifier converts this photo-current to a voltage that is digitized by the Lab PC 1200 card. This allows for interpreting the image to select cells or particles having an optical reporter for sorting, as they pass through the detection region, based for example on the amount of light or fluorescence measured as an indication of whether a cell or particle has a predetermined level of reporter and should be chosen for collection. Voltages at the electrodes of the chip can be adjusted or switched according to this determination, for example by signals initiated by or under the control of a personal computer acting in concert with the Lab PC 1200 card.

6.12.5. Absorbance Detection

In another embodiment for detecting cells or molecules, absorbance detection is employed, which typically uses relatively longer wavelengths of light, e.g., ultraviolet (UV). Thus, for example, a UV light source can be employed. Additional objective lenses can be used to image a detection region, such that the lenses are preferably positioned from the top surface if the PDMS device is made reasonably thin. Measurement of the light transmitted, i.e., not absorbed by the particle or cell, using an adjustable slit, e.g., a Zeiss adjustable slit as described above, is similar to that used in fluorescence detection. A spectrophotometer may also be used. As molecules, particles or cells pass through the detection window they attenuate the light, permitting detection of a desired characteristic or the lack thereof. This can improve the accuracy of the particle sorting, for example, when sorting based on an amount of a characteristic, rather than presence of the characteristic alone, or to confirm a signal.

It is noted that in some cases, detection by absorbance may be detrimental at certain wavelengths of light to some biological material, e.g., *E. coli* cells at shorter (UV) wavelengths. Therefore, biological material to be sorted in this manner should first be tested first under various wavelengths of light using routine methods in the art. Preferably, a longer wavelength can be selected which does not damage the biological material of interest, but is sufficiently absorbed for detection.

6.12.6. Optical Trapping

In another embodiment, an optical trap, or laser tweezers, may be used to sort or direct molecules or cells in a PDMS device of the invention. One exemplary method to accomplish this is to prepare an optical trap, methods for which are well known in the art, that is focused at the "T" intersection proximate to, and preferably downstream of, the detection region. Different pressure gradients are established in each branch. A larger gradient at one branch channel creates a dominant flow of molecules, particles or cells, which should be directed into the waste channel. A second, smaller gradient at another branch channel should be established to create a slower flow of fluid from the "T" intersection to another channel for collection. The optical trap remains in an "off" mode until a desired particle is detected at the detection region. After detection of a desired characteristic, the particle or cell is "trapped", and thereby directed or moved into the predetermined branch channel for collection. The molecule or cell is released after it is committed to the collection channel by turning off the trap laser. The movement of the cell or molecule is further controlled by the flow into the collection well. The optical trap retains its focus on the "T" intersection until the detection region detects the next molecule, cell or particle.

Flow control by optical trapping permits similar flexibility in buffer selection as a pressure driven system. In addition, the pressure gradients can be easily established by adjusting the volume of liquid added to the wells. However, it is noted that the flow rate will not be as fast when the pressure in one channel is above ambient pressure and pressure in another is below.

6.12.7. Forward Sorting

In an electrode-driven embodiment, prior to loading the wells with sample and buffer and placing the electrodes, the electrode voltages are set to zero. Once the sample is loaded and the electrodes placed, voltages for the driven electrodes are set, for example using computer control with software that prompts for the desired voltages, for example the voltage differential between the sample and waste electrodes. If the three wells are equidistant from the "T" intersection, one voltage will be slightly more than half the other. In a typical run, the voltages are set by the program to start with directing the molecules, particles or cells to the waste channel. The user is prompted for the threshold voltage of the PMT signal, to identify a molecule, particle or cell for sorting, i.e. diversion to the collection channel and well. A delay time is also set. If the PMT voltage exceeds the set threshold, the driven electrode voltages are swapped and then, after the specified delay time, the voltages are swapped back. The delay allows the selected molecule, particle or cell enough time to travel down the collection channel so that it will not be redirected or lost when the voltages are switched back. As described above, a slight gradient is maintained in the waste channel, when the voltages are switched, to provide continuity in the flow. This is not strong enough to keep the molecule, particle or cell moving into the other or "off" channel it if is too close to or is still at the branch point.

The value of this delay depends primarily on the velocity of the molecules, particles or cells, which is usually linearly dependent on the voltage gradients. It is believed that momentum effects do not influence the delay time or the sorting process. The molecules, particles or cells change direction almost instantaneously with changes in the direction of the voltage gradients. Unexpectedly, experiments have so far failed to vary the voltages faster than the particles or cells can respond. Similarly, experiments have so far shown that the dimensions of the channels do not effect the delay, on the distance and time scales described, and using the described electronics. In addition the speed with which the cells change direction even at high voltage gradients is significantly less than needed to move them down the appropriate channel, when using a forward sorting algorithm.

Once the voltage and delay value are entered the program, it enters a sorting loop, in which the ADC of the Lab PC 1200 card is polled until the threshold value is exceeded. During that time, the flow of particles or cells is directed into one of the channels, typically a waste channel. Once the threshold is detected, the above voltage switching sequence is initiated. This directs a selected cell or particle (usually and most preferably one at a time) into the other channel, typically a collection channel. It will be appreciated that the cells or particles are being sorted and separated according to the threshold criteria, without regard for which channel or well is considered "waste" or "collection". Thus, molecules or cells can be removed from a sample for further use, or they can be discarded as impurities in the sample.

After the switching cycle is complete (i.e. after the delay), the program returns to the ADC polling loop. A counter has also been implemented in the switching sequence which keeps track of the number of times the switching sequence is executed during one run of the program. This should represent the number of molecules, cells or particles detected and sorted. However, there is a statistical chance that two molecules, cells or particles can pass through simultaneously and be counted as one. In this embodiment, the program continues in this polling loop indefinitely until the user exits the loop, e.g. by typing a key on the computer keyboard. This sets the DACs (and the electrodes) to zero volts, and the sorting process stops.

6.12.8. Reverse Sorting

The reverse sorting program is similar to the forward sorting program, and provides additional flexibility and an error correction resource. In the event of a significant delay in changing the direction of flow in response to a signal to divert a selected molecules, cell or particle, for example due to momentum effects, reversible sorting can change the overall direction of flow to recover and redirect a molecule, cell or particle that is initially diverted into the wrong channel. Experiments using the described electrode array show a delay problem and an error rate that are low enough (i.e. virtually non-existent), so that reversible sorting does not appear necessary. The algorithm and method may be beneficial, however, for other embodiments such as those using pressure driven flow, which though benefitting from an avoidance of electrical polarities and high voltages, may be more susceptible to momentum effects.

If a molecule or cell is detected for separation from the flow, and switching is not fast enough, the molecule or cell will end up going down the waste channel with all of the other undistinguished cells. However, if the flow is stopped as soon as possible after detection, the molecule or cell will not go too far. A lower driving force can then be used to slowly drive the particle in the reverse direction back into the detection window. Once detected for a second time, the flow can be changed again, this time directing the molecule or cell to the collection channel. Having captured the desired molecule or cell, the higher speed flow can be resumed until the next cell is detected for sorting. This is achieved by altering the voltages at the electrodes, or altering the analogous pressure gradient, according to the principles described above.

To move molecules or cells at higher velocities, for faster and more efficient sorting, higher voltages may be needed, which could be damaging to molecules or cells, and can be fatal to living cells. Preliminary experiments indicate that there may be a limit to the trade-off of voltage and speed in an electrode driven system. Consequently, a pressure driven flow may be advantageous for certain embodiments and applications of the invention. Reversible sorting may be advantageous or preferred in a pressure driven system, as hydraulic flow switching may not be done as rapidly as voltage switching. However, if a main or waste flow can move fast enough, there may be a net gain in speed or efficiency over voltage switching even though the flow is temporarily reversed and slowed to provide accurate sorting. Pressure driven applications may also offer wider flexibility in the use of buffers or carriers for sample flow, for example because a response to electrodes is not needed.

6.13. Design and Microfabrication of a Multiparameter Chip

This device incorporates a built-in microfluidic system constructed by multi-layer soft lithography (27) using techniques such as those described in Example 9. The integrated fluidic system has an input well, a main channel which incorporates a central hybridization loop, an output well, inlet and outlet on/off valves, and a peristaltic pump. Micrographs of an exemplary device are shown in FIGS. 13A and B.

6.13.1. Chip Architecture

In a departure from conventional systems, this embodiment of the invention does not rely on DNA probes on a substrate that are passively exposed to a sample. This chip incorporates a built-in fluidic system that actively contacts probes and sample. The fluidic system is made by multi-layer soft lithography as described herein. See also, Example 9, Unger et al. (6), and U.S. Pat. No. 5,661,222 (32). In this example, GE Silicone RTV 615A and 615B are mixed and then poured onto two different molds, a fluid or treatment channel mold and an air or control channel mold. Part A contains vinyl groups and catalyst; part B contains silicon hydride (Si—H) groups. The conventional ratio for RTV 615 is 10 parts A to one part B (10:1). For bonding, one layer may be made with 30A:1B (excess vinyl groups) and the other with 3A:1B (excess Si—H groups). Each layer is cured separately. When the two layers are brought into contact and cured at elevated temperature, they bond irreversibly forming a monolithic elastomeric substrate. On these two molds, there are intrusive (negative) patterns, which define the final indent fluid or air channels in the cured RTV silicone devices. After partial curing in an oven, RTV from the air channel mold is peeled off and placed on top of the fluid channel mold. With a second baking, these two RTV faces bond together, forming an integrated fluidic system. In this example, the system has two layers, although multiple layers are possible. Air and fluid channels in their respective layers are embedded inside the whole assembly. Air channels are above and proximate to fluid channels over some portion of their length. The air channels do not connect with the fluid channels directly. However, they do interact with each other at intersections where a microvalve is formed.

In this example the air channels are about 100 or 200 μm wide and about 10 μm deep (FIGS. 13A and 13B). Suitable air channel dimensions include those ranging from about 50-2001 m wide and are from about 2-50 μm deep, preferably about 10-50 μm. A preferred depth is about 10 μm. The fluid channels are about 100 μm wide and about 10 μm deep. Suitable fluid channel dimensions include those ranging from about 10-200 µm wide and from about 2-50 µm deep, more preferably about 2-20 µm deep. A preferred depth is about 10 µm.

When sufficient air pressure is applied in the air channel, the RTV membrane between the air and fluid channels is pushed down, acting as a microvalve, and restricts or closes the bottom fluid channel. The pumping pressure or force is not critical. Exemplary pressures are in the range of 5-50 psi, but any pressure may be used that is sufficient to close microvalves on the chip without damaging the device (e.g. challenging the seal between an elastomeric layer and an adjacent layer or substrate. Fluid speed tends to be determined less by pressure than by the frequency of valve cycling. Frequencies of about 75-100-Hz, preferably 75 Hz are suitable in certain preferred embodiments. In some preferred embodiments, valves are restricted but not fully closed, particularly valves comprising a pump. This approach avoids contact by valve membranes with the opposing face of the channel, e.g. with the probe substrate. Possible disturbance of the probes is prevented, while still providing rapid and efficient pumping action within the loop. By controlling external 3-way pneumatic valves such as LHDA1211111H from the Lee Company, (Westbrook, Conn.) the on/off state of each individual microvalve on the chip can be manipulated. Three microvalves in a series become a peristaltic pump when an appropriate on/off pumping sequence is applied.

The integrated fluidic system has an input well, an output well, inlet and outlet on/off valves, a central hybridization or target loop, and a peristaltic pump built in with the central loop. Photographs of components of an assembled device are shown in FIGS. 13A and 13B.

FIG. 13A shows an input or handling assembly 1 of an integrated microfluidic chip. The device has a fluid layer (bottom layer) with an input mixing T-channel 5, junction 9 and feed channel 15. The air channel layer (top layer in this example) has six air channels 7, forming a microvalve 17 where each air channel intersects input channel 5. The bottom wide 100-µm air channel 3 is used to close the inlet 15 via a microvalve created at intersection 13, when the peristaltic pump at the loop or ring of FIG. 13B starts operating for hybridization. The feed channel 15 at the bottom of FIG. 13A connects to the top channel 15 of FIG. 13B.

FIG. 13B shows a treatment assembly 20. A treatment layer with fluid channels is shown. The treatment layer of this example has a target or hybridization loop 28, which in this example forms a circular shape in a plane of the chip. In one embodiment of the invention, the center ring or target loop 28 is used for DNA hybridization with a sample introduced to loop 28 from the feed channel 15. Sample can exit the loop at channel 30. This channel can also be closed, for example to selectively keep fluid in a closed loop 28, by using another microvalve (not shown) in cooperation with valve 13. Air channels 22 appear as radial fingers in this example, and can form microvalves 32 where each air channel intersect loop 28. Any three of these channels 22 and valves 32 can be used in series to provide a peristaltic pump.

In this embodiment the control layer and air channels are above or on top of the treatment layer and fluid channels. This is depicted in FIGS. 13A and 13B. The air channels can be seen overlapping the fluid channels in the view shown in the figures. It should be noted, however, that "up," "down", "top" and "bottom" are convenient relative terms. The chip and assemblies of the invention, and the layers and channels, can be oriented in any desired direction. As one example, the device may be flipping over to change a "top" layer or face in a "bottom" layer or face.

Except for air channel 3, which is 100 µm wide, the channel width of both the fluid channels and air channels in this example is about 50 µm wide and 10 µm deep. The entire device in this example is about 1" by 1" in size.

The central loop or detection region 28 of FIG. 13A is where DNA hybridization probes are laid down along the ring, preferably on a glass substrate (not shown), following all or part of a path corresponding to all or part of the loop. DNA samples and fluorescent intercalating dyes can enter from the branches of the channel shown in FIG. 13A. On/off states of each microvalves are controlled by external pneumatic valves (e.g. Lee LHDA1211111H), which either apply 50 or 100-kPa air pressure to the microvalves or vent them to the atmosphere. A cycling frequency of up to 75 Hz has been demonstrated with complete opening and closing of the valves (75). An alignment structure 24 can be provided on each layer of the microfabricated device, to assist in properly aligning adjacent layers when they are overlayed and bonded together. Such structures can function in two dimensions, e.g. length×width for visual alignment, or in three-dimensions, e.g. length×width×depth for a physical or "lock-in-key" alignment.

In this example, channels molded into the RTV are at different depths or layers, but are exposed to a common face of the chip when peeled off from the supporting mold, because the elastomer is transparent. The multilayer assembly (here a two-layer RTV assembly) is aligned and bonded to a transparent (e.g. glass) substrate (not shown). The bond in this example forms a hermetic seal when the RTV and glass substrate are contacted shortly after removing the RTV from the mold. In this example, the glass substrate is patterned in advance with a desired set of DNA probes. For example, the entire DNA probes for a number of different diseases are laid down along a path on the glass substrate that corresponds and communicates with the loop 28.

A chip of the kind depicted in FIG. 13 is shown schematically in FIG. 17. Fluid lines 101 carry a sample, typically an aqueous solution, into a detection loop 105. The detection loop 105 is provided with diagnostic spots 110, which for example are DNA or antibody probes affixed to a substrate and presented to the fluid in the loop channel 105. Control lines 115 are above or below the fluid lines 101, and typically carry a gas, preferably air, under pressure. As described herein, microvalve 120 is formed where the control lines 115 and fluid lines 101 or 105 intersect. Three valves 120 in series along the loop channel 105 provide a peristaltic pump in response to an appropriate on/off or open/close sequence. The peristaltic pump circulates fluid within the loop 105. The loop 105 can be closed or isolated from other fluid channels 101 by closing the valves on the in and/or out sides of the loop 105.

6.13.2. Chip Fabrication

Air and fluid mother molds were fabricated on silicon wafers by photolithography. Photoresist (Shipley SJR5740) was spun onto a silicon substrate at spin rates corresponding to the desired channel heights. After photolithography, intrusive channels made of photoresist were formed. Fluid channel molds were baked on a hot plate of 200° C. for 30 minutes so that the photoresist could reflow and form a rounded shape, which in this embodiment is important for complete valve closure (76). A one minute trimethylchlorosilane (TMCS) vapor treatment was applied to these molds before each RTV replication process to prevent adhesion of cured RTV to the photoresist. With this protective coating, molds can be reused many times. A mixture of GE RTV 615 components, in an RTV ratio of 615A:615B of 30:1 was spun on a fluid channel mold at 2,000 RPM, which covers the photoresist channel and leaves a thin membrane on top of it. At the same time, 3:1 GE-RTV 615A:61 dB was poured onto an air channel mold. After baking both molds in an oven at 80° C. for 20 minutes, the block of 3:1 RTV with air channels at the bottom was peeled off from the second mold. Air supply through-holes were punched. Aligned to the fluid pattern under a microscope, the air channel layer was then pressed against the thin 30:1 RTV on the first mold. A post-bake of an hour at 80° C. made the two silicone pieces or layers chemically bond to each other. After peeling the assembly off from the remaining mold and punching the fluid through-holes, the monolithic RTV device could seal hermetically to a glass cover slip. This glass cover slip can be chemically patterned in advance, to make an active diagnostic chip. If high-resolution transparency photomask are used (minimum feature size: ~10 μm), the whole process from the design to the final products can be accomplished very quickly, even without automation, e.g. in one day.

6.13.3. Operation of a DNA Hybridization Embodiment

In operation, a few microliters of sample, containing perhaps as few as 50 or 100 molecules of DNA, are loaded from an input well (not shown) via inlet 5 of handling assembly 1, and fill the fluid channels of the device by capillary action. After the central loop 28 is completely filled, inlet and outlet valves (not shown) associated with channels 26 and 32 are closed. The peristaltic pump is turned on, via microvalves 22, to move the fluid around and around loop 28 in a closed circle. Instead of a passive diffusion process, the target DNA fragments polynucleotides or molecules contained inside the sample are actively pumped to pass each individual hybridization spot. The sample passed every probe several times, so that almost all DNA that targets a probe will find the right spots to hybridize with. Very little sample is needed. This is a significant improvement over conventional passive DNA chips.

Improved Accuracy. Intermittent heating can also be applied to denature false hybridization and thus obtain an even more accurate diagnostic result. This approach improves the signal-to-noise ratio in certain embodiments. Another technique to improve accuracy, and (for example) to avoid false positives, is to provide additional hybridization spots, before or within the target loop, to extract common DNA, leaving unmatched sample DNA to bind with target probes on other hybridization spots in the detection loop, for labeling and/or detection. In this way, DNA that is known not to match any of the target DNA probes can be screened or filtered out.

Optical Detection. After hybridization, the chip can be checked under an optical microscope easily, because the whole body of the chip is transparent. Intercalating dyes, incorporation of fluorescent-labeled single nucleotides, DNA beacons or other well-established detection schemes can be used to determine the final diagnostic results.

In one preferred embodiment, intercalating dye is used. Fluorescent intercalating dyes, such as YOYO-1, TOTO-1 and PicoGreen from Molecular Probes, have been demonstrated to have very high affinity to double-stranded DNA (dsDNA), big excitation cross-sections and high quantum efficiency. Most important of all is that their fluorescence is enhanced more than one-thousand fold when bound to dsDNA fragments (7, 8), and shows a relatively high selectivity to dsDNA compared to single-stranded DNA probe (ssDNA). When concentration of dsDNA is below 100 pg/ml, 10× more concentration of ssDNA results in no more than a 10% change in the signal intensity of PicoGreen stained DNA (10). This means that at least 100-fold discrimination between dsDNA and ssDNA has been demonstrated. With such a high specificity and binding enhancement, these dyes are highly suitable as an indicator of hybridized DNA probes. Detection of individual stained dsDNA molecules using laser excitation has been reported, e.g. (8,9), but is not necessary. An optical microscope with a mercury illumination lamp and a CCD camera gives a reasonable justification between hybridized and non-hybridized spots as long as a few seconds of exposure is applied to obtain a similar signal level.

In one embodiment, the target loop (e.g. loop 28) is provided with a second inlet valve and/or inlet channel, to deliver an additional flow or additional materials or reagents, such as a buffer or sample-free medium. After hybridization, this valve (not shown) and an outlet valve for channel 30 (not shown) are opened. Buffer with dye molecules can then be introduced to flush the loop 28, to remove free DNA in the solution, and also to stain the hybridized fragments at the bottom. After a few minutes of incubation, the whole chip can be checked under an optical microscope, as described herein. A computer program can be used to determine the existence of certain disease targets by a threshold algorithm. Severity of the infection can be also determined according to the fluorescent intensity of the corresponding hybridization spot.

DNA beacons are a special kind of hybridization probes, and are commercially available for example from Integrated DNA Technologies, Inc, (Coralville, Iowa); Oswel Rearch Products Ltd. (UK), Cruachem, Inc. and Research Genetics, Inc. When not hybridized with their complimentary DNA fragments (target DNA), they are self-annealed to themselves and thus quench their own fluorescence. Therefore, no additional staining step is required for a final diagnosis. However, these probes are more expensive, and special probing sequences have to be carefully chosen in order for the self-annealing mechanism to take place. In-situ enzymatic labeling with fluorescent molecules is another well-known method and is obviously compatible with the design of this lab-on-a-chip device. These and other reporter and labeling techniques can be used in concert with the microfluidic devices and methods of the invention.

In addition to the diagnostic design described above, other functions can be incorporated into the integrated device as needed. Switching valves and mixing chambers can be designed and built into the chip. For example, an automatic inline restriction and denaturing process can be included before the hybridization process, to reduce handling labors. For an extremely small quantity of target samples, a PCR chamber can built into the device, and reactions can be carried out by an external or an inline thermal cycler (11). Other enzymatic labeling and reactions can be easily incorporated into it just like the way we described above for DNA fluorescent staining.

A device of the invention is shown schematically in FIG. 14. A microfluidic assembly 40 comprises a fluid or treatment layer 44 and a control or air layer 46. In this embodiment, fluid channels are microfabricated into the treatment layer 44, and air channels are microfabricated into the control layer 46. The control layer is on top of and is bonded or sandwiched to the treatment layer. These layers overlap, and are typically but not necessarily coplanar or coextensive. In this embodiment the layers are transparent, and the control layer is bonded on its upper face, in whole or in part, to a transparent cover layer 48, preferably glass (e.g. pyrex).

In the treatment layer 44, a sample inlet channel 50 communicates with a target hybridization loop 58, which in turn communicated with an outlet channel 68. A reagent channel 52 communicates with the sample inlet channel 50. The control layer 46 has a first air channel 54, which forms a microvalve 72 to open and close the sample inlet channel 50, particularly with respect to the target loop 58. Similarly, a second air channel 66 provides a microvalve 74 to open and close the outlet channel 68. At least three pump channels 56 providing microvalves 78 are on the control layer. Using air in the pump channels 56, e.g. by changing the pressure, the valves 78 can be opened and closed in a series or cycle, to create a pumping action in the target loop 58, represented by the four arrows in FIG. 14 showing a counterclockwise motion. The heavy arrows represent fluid, e.g. sample, in the fluid channels. The lighter arrows represent air in the air channels, e.g. to actuate the microvalves.

The cover layer 48 (e.g. a glass substrate) is patterned with target molecules (e.g. DNA probes) in distinct spots 60, 64 on the inward face of the cover layer, i.e. toward the other layers. The pattern of spots follows a path that corresponds to the path of the target loop 58, and the fluid channel comprising the loop 58 is open or exposed to, and typically is sealed by, the inward face of the cover layer. Thus, the cover layer 48 forms a ceiling, wall or floor of the fluid channels, depending on the orientation of the assembly 40. In the view shown in FIG. 14, the cover layer 48 forms a ceiling for loop 58, and may be extended to cover other channels, the entire assembly, or may extend beyond the assembly (not shown). In a preferred embodiment, all three layers (treatment, control and cover) are coplanar and coextensive).

In operation, a sample is loaded into inlet channel 50, and the fluid channels are allowed to fill by capillary action. Channel 54 may be used to add reagents or buffer, or to wash the fluid channel, as and when desired. The microvalves 72 and 74 are closed, to isolate the loop 58. At least three microvalves 56 are actuated to form a peristaltic pump, which circulates sample inside the loop, for repeated and active exposure to the probes at the hybridization spots 60, 64. The black spots 60 represent a component of the sample (e.g. a DNA fragment) binding to a corresponding target probe on the cover layer. The white spots 64 represent target probes fixed to the cover layer and exposed to circulating sample.

In a preferred DNA hybridization embodiment, the chip is washed (e.g. with buffer), loaded with sample, the loop is closed, the sample is circulated around the loop, and the chip is heated up to a temperature that is near but below the lowest annealing temperature of the probe DNA. The heat acts to prevent or reverse false hybridization, by breaking weak bonds between sample molecules and non-matching probes, without denaturing the DNA of the sample or the probes. Each primer has an annealing temperature, which can be determined or calculated by known means, for example using commercially available probe design software. Mismatched hybridization may be a function of annealing temperature, and accordingly, maintaining a temperature that is below the annealing temperature tends to minimize false hybridization. Typically, the annealing temperatures are such that the operating temperature is set in the range of about 55-70° C. The hybridization cycle is completed by opening valve 74 to drain the loop of sample, following by a washing step, in which buffer or other reagent in fed to the loop from channel 52 by opening valve 72. Washing conditions can be optimized to remove sample, leaving behind the positive hybridization spots 60, where sample molecules are bound to or associated with target probes. Alternatively, washing conditions can be optimized to flush the loop for a fresh round of sample and testing. Loading, treatment, detection, and washing cycles can be repeated as desired, in any order, for any length of time, and according to any protocol.

In one embodiment, fluorescent labeled nucleotides and polymerase are introduced to the loop (e.g. via channel 52 and valve 72) to extend the hybridized samples and provide a detectable reporter, followed by a washing step. For example, a positive hybridization can be detected by observing any hybridization spots that fluoresce, for example using an optical microscope. The microscope can be used with a charge coupled device (CCD) to image the loop, and processing, imaging, and analysis can be automated or assisted by a computer, e.g. a personal computer.

This method is suitable for samples of very low volume, e.g. 1-50 μl, typically 10 μl. In certain embodiments it may be desirable to dilute or concentrate the sample. For example, in embodiments where primer extension is done on the chip (at the hybridization spots), dilution or additional samples may be needed If the extension length of a primer is about 5K, hybridization can be imaged (e.g. using a CCD) from as few as about 10 extended DNA molecules on each spot. Accounting for possible loss of sample, e.g. during device or target loop loading, a minimum of about 20 molecules in the loaded sample is preferred. More typically, a minimum of about 30 to 100 molecules is preferred.

6.14. Surface Patterning of a Multiparameter Chip

This example describes the surface patterning of a microfluidic device of the invention, using two different kinds of surface chemistries. These devices are useful, for example, to measure gene expression and detect the presence of pathogenic DNA. As described above, the microfluidic devices pump solutions of target DNA over a set of anchored probes in order to ensure that all of the target DNA is exposed to each of the probes. This provides increased sensitivity as well as decreasing the amount of time needed for hybridization. Chips with high sensitivity are useful for measuring single cell gene expression. This higher sensitivity may eliminate the need for PCR in many cases, e.g. of pathogen detection. Such devices can provide multiple analysis or disease diagnosis with one integrated lab-on-a-chip.

The microfluidic devices of the invention are compatible in structure, material and manufacturing with the delicate surface chemistry required to anchor or synthesize DNA probes onto the chip. The desired patterning or surface chemistry is used to place probes on the chip, for example in a detection or target loop as described above. Small amounts of material are manipulated in order to perform biochemical reactions on the chip, including the ability to pump a sample over probes that are patterned on the chip.

The soft lithography techniques described herein are suitable for handling DNA and reactions involving DNA, and for patterning a substrate with DNA probes. The elastomeric devices of the invention provide a number of important advantages over conventional micromachining, such as ease of fabrication, room temperature sealing of devices to glass substrates, good optical properties, and low materials cost. Microfluidic networks fabricated in such a manner can easily be sealed to substrates with delicate surface chemistry. Another aspect of soft lithography is the ability to chemically pattern surfaces using fluid flow (78, 79). The multilayer fabrication process in silicone elastomer, described herein, furnishes the easy fabrication of devices with moving parts, including microfluidic valves and pumps (U.S. Patent Application Ser. No. 60/186,856, filed Mar. 3, 2000 entitled "Microfabricated Elastomeric Valve and Pump Systems".)

In this example, a microfluidic device of the invention has surfaces that are chemically patterned with biotin/avidin and DNA using fluidic networks that are compatible with further fluidic processing. Pumps can be incorporated into the device to both meter reagents and pump fluid in a closed loop.

Multilayer soft lithography, described herein, is used to make 3-D monolithic elastomer devices with a combination of air and fluid channels. The devices of this example were made as described in Example 13. When an air channel passes above another fluid channel, the thin membrane between these two channels becomes a valve. By applying air pressure in the air channel, the membrane collapses and stops the fluid flow. Releasing the pressure then re-opens this valve. Three valves in series become a peristaltic pump when an appropriate on/off air pressures are applied in a sequence. For example, three valves in series can be represented by the letters "XYZ," with 0 representing a closed valve and 1 representing an open valve. As shown in the following table, the XYZ sequence 100, 110, 010, 011, 001, 101 pumps water to the right, e.g. from opened (on) valves toward closed (off) ones. These and other sequences can be used to direct and control fluid flow, change flow direction, start and stop flow, etc. For example, the table below specifies an exemplary sequence of six steps or "words" that can be used to pump fluid through a microfabricated rotamer loop.

|      | Valve |       |       |
| ---- | ----- | ----- | ----- |
| Step | X     | Y     | Z     |
| 1    | 1-on  | 0-off | 0-off |
| 2    | 1-on  | 1-on  | 0-off |
| 3    | 0-off | 1-on  | 0-off |
| 4    | 0-off | 1-on  | 1-on  |
| 5    | 0-off | 0-off | 1-on  |
| 6    | 1-on  | 0-off | 1-on  |

Three word pumping sequences may also be used, for example the sequence 001, 010, 100 or, alternatively, the sequence 011, 110, 101. Performance between these different sequences is relative similar when the peristaltic pump is operated at the linear regime; i.e. when the cycling frequency is less than about 75 Hz.

A schematic diagram of a peristaltic pump of the invention is shown in FIG. 15. In this exemplary embodiment, the distance between the air channels and the fluid channels, where they intersect, is a vertical gap of about 30 μm. The fluid and air channels are preferably disposed at an angle to one another with a small membrane of elastomeric material separating the top of one channel (e.g. an air channel) from the bottom of another channel (e.g. a fluid channel).

Two independent methods of surface patterning are disclosed. The first method provides patterning of the protein streptavidin, a common biochemical "glue" that binds biotin with nearly covalent strength. Using the streptavidin surfaces, biotin-labeled reagents are selectively anchored, including proteins and nucleic acids. The second method provides direct attachment of amine-modified DNA molecules to a surface using a commercially available surface chemistry from the company Surmodics, Eden Prarie, Minn.

6.14.1. Straptavidin Binding

In the first method, half of the surface of a glass cover slip (VWR #1, from VWR Scientific Products, Inc., Chester, Pa.) was derivatized with biotin. The coverslip was aligned and contacted with the fluid channels of a silicon elastomer layer, as described above, and the channels were flowed with avidin-fluorescein conjugate, after which the channels were flushed with water and removed from contact with the coverslip. The coverslip was washed. As shown in FIG. 16A, the avidin molecules bound to the derivatized part of the glass surface with a high affinity in the regions defined by the channels, forming fluorescent detectable stripes in a distinctive line pattern. Regions which were not derivatized with biotin function as a control and showed a much lower level of avidin binding.

The substrate surface can be successively patterned. In this embodiment, the surface was patterned with non-fluorescent streptavidin by bonding an elastomeric device with channels to the substrate and flowing streptavidin down the channels. As before, streptavidin bound selectively to the surfaces that were exposed to the channels, and not to the elastomer surfaces. Since streptavidin is a tetramer, each molecule has at least two exposed groups free to bind more biotin. This was demonstrated by removing the elastomeric channels and re-bonding in an orientation that was rotated by 90 degrees. Biotin-fluorescein conjugates were flowed down the channels and then washed with water. As shown in FIG. 16B, the fluorescent biotin binds selectively to the regions that are derivatized with streptavidin. A checkerboard pattern was obtained in this figure by flowing streptavidin horizontally (200 μm) and biotin-fluorescein conjugates vertically (100 μm).

6.14.2. Covalent Immobilization of DNA

Surfaces can be prepared and patterned with DNA using commercially available silanized slides, such 3D-Link, provided by Surmodics. In this example, DNA samples were prepared by PCR of a 2 kpb region of lambda phage DNA using amino-terminated primers. The DNA was attached in situ by flowing it through an elastomeric channel replica made from the air channel mold of the diagnosis chip, i.e. the finger patterns in FIG. 13B. After overnight incubation, the elastomeric device was peeled off from the slide, and washing and immobilization steps were followed according to the manufacturer's protocol. To show that the DNA was attached and patterned to the surface, a diagnostic RTV device (as shown in FIGS. 13A and 13B) was aligned and attached to the same slide. Then, the DNA intercalating dye PicoGreen (Molecular Probes P-7581) was flowed through the bottom fluid channels 15, 28, 30, of which the central ring 28 intersected with every DNA finger pattern on the slide. The intersection of the channels fluoresced, as shown in FIG. 16C. Although this particular example uses DNA, protein-binding assays and other molecular affinity assays can also be used with these fluidic systems.

The DNA diagnostic chip in this example has a junction 9 for mixing and metering reagents (FIG. 13A), which then leads into a fluidic loop 28. In this embodiment, probe molecules are anchored or immobilized in the loop, via bonding to an aligned substrate, so that the sample (or probe target) can circulate around. The loop has air channels 22 forming peristaltic pumps to control circulation. The fluidic connections into and out of the loop 28 are controlled by input and output valves, respectively. (In other embodiments, probes may circulate freely in a target loop, or may be fixed to a surface such as beads, for circulation in the target loop, exposure to sample, and later imaging or detection at a detection region of the device.)

Mixing and metering occurs in the first part of the chip (FIG. 13A). A solution containing fluorescent dye is mixed with an aqueous solution, for example using flows that can be alternated with different (e.g. two) valve-firing schemes. If the valves are opened and closed in synchrony, the fluid mixing is controlled by diffusion. There are two segregated flows when the valves are open, which quickly mix by diffusion when the valves are closed. If the valves are opened and closed alternately, slugs or droplets of fluid are injected into the stream.

Fluid is circulated within the closed loop using the peristaltic pumps on the perimeter. The channels were loaded with fluorescent beads (2.5 μm in diameter). The beads could be visualized as the fluid circulated around the loop and clearly showed rotary motion with no net flux into or out of the loop. Thus reagents can be repetitively exposed to diagnostic probes anchored on the surface, and their binding is not limited by diffusion. All or substantially all target DNA in a sample is eventually captured by corresponding probes after several passages. Such a device can also be used to rapidly mix viscous liquids, since the parabolic flow profile of the fluid will tend to "wrap" the two fluids around each other.

In these experiments, surfaces were chemically patterned with biotin/avidin and DNA using fluidic networks in a way that is compatible with further fluidic processing. Experiments also show how pumps can be incorporated into an integrated device to both meter reagents and pump fluid in a closed loop. Fast in-line mixing and rotary pumping were demonstrated to overcome the slow hybridization process.

In a microfluidic device with a closed loop and peristaltic pump, as described, avidin coated 1-μm beads were captured onto biotin spots within 4 minutes after the pump was activated. In contrast, when using passive diffusion, only beads very local to the reaction spots were captured even after hours of waiting time.

Rotary flow in a closed loop cannot be achieved by the electrophoresis or electroosmotic flow used in the conventional and most common lab-on-a-chip devices, because of the existence of two electric polarities. The problem of buffer depletion due to electrolysis in electroosmotic or electrophoretic flow control does not exist in pump and valve devices. However, it should be noted that electoosmotic or electrophoretic flow control systems, and/or other flow control systems, can be used in combination with the pumps and valves disclosed herein. For example, other flow control systems can be used to move fluids on other parts of a multifunction chip, or from one chip to another in a device comprising cooperating microfluidic chips, layers, units or subunits.

6.15. In-Line Rotary Mixing

The exemplary device of FIG. 13 has a junction 9 for mixing and metering reagents, which then leads into a fluidic loop 28 via inlet channel 15. In this example, mixing and metering in the first part of the chip (FIG. 13A) is described. A solution containing fluorescent dye was mixed or metered with an aqueous solution. For example, the flows can be alternated with two different valve-fring schemes. If valves 7 are opened and closed in synchrony, fluid mixing is controlled by diffusion. Two segregated flows are observed when the valves are open. These flows quickly mix by diffusion when the valves are closed. If the valves are opened and closed alternately, then slugs or droplets of fluid are injected into the stream.

Fluid was pumped within the closed loop 28 using the peristaltic pumps on the perimeter. The channels were loaded with fluorescent beads (2.5 μm in diameter). The beads could be visualized as the fluid circulated around the loop and showed rotary motion with no net flux into or out of the loop. Thus reagents can be repetitively exposed to diagnostic probes anchored on the surface, and their binding will not be limited by diffusion. Likewise, all target molecules in a sample (e.g. DNA) are exposed to and eventually (and relatively quickly) interact with or are captured by their corresponding probes after several passages or turns around the loop. There is little or no loss of sample, and in many or even most cases PCR amplification of the sample is not needed.

Mixing within the loop can also be done without the presence of probes in the loop, for example to facilitate a chemical reaction or combination of different flows or ingredients in different flows introduced upon a mixing protocol as described above.

The loop can contain or be provided with any material or reactant, immobilized or not, for any reaction or interaction with any other material or reactant provided to the loop. Immobilized reactants may be attached to any substrate, fixed or mobile, including carrier molecules, beads, or a substrate (e.g. glass) communicating with the elastomeric loop channel 28.

A device of FIG. 13 was also used to rapidly mix viscous liquids. The peristaltic pump provides a flow profile (e.g. parabolic) whereby two (or more) fluids tend to "wrap" around each other to provide in-line rotary mixing, as shown in FIG. 18.

No Pumping Action. In FIG. 18A, buffer containing fluorescent beads came in from the left input channel at the T-junction while buffer containing the fluorescent dye FITC came in from the other side (FIG. 18A). Because of a laminar flow profile, these two fluids did not mix with each other and actually split the flow channel into halves, one side with only beads and the other side with fluorescent dye. When they enter the central ring or loop, without pumping, the ring was also split into two distinct parts. On the left-hand side, there were just beads flowing through and on the right-hand side, there was only bright and uniform fluorescent dye. At the bottom of the ring, these two flows met with each other again (FIG. 18A). The channel was split into two distinct portions again. The inset illustrates the flow pattern shown in the photograph.

Pumping Activated. When peristaltic pumping was turned on at the central ring, the situation changed significantly. As shown in FIG. 18B, both dye and fluorescent beads were well mixed at the output channel. Part of the fluid was actually pumped back to the input of the ring and forced the two distinct streams to mix with each other. This fast in-line mixing by rotary pumping is useful in many microfluidic systems particularly where time and space is critical, and when fluid contains substances with small diffusion constants, such as DNA and micron-sized beads.

6.16. Model Biotin and Avidin System

A biotin/avidin model system demonstrated the difference, in terms of detection efficiency, between a passive and an active diagnosis chip. An RCA-cleaned cover slip was first patterned by flowing biotinylation solution though an attached RTV device with eight finger channels made from an air-channel mold as in FIG. 13. After overnight incubation, the RTV device was peeled off and the cover slip was washed with DI water. A multiple disease diagnosis device (FIG. 13) was then attached with its center aligned to the center of the biotinylated fingers. Therefore, the central ring was able to intersect with all biotin fingers and formed eight diagnostic spots. The pattern shown in FIG. 16C was made in the same manner except that the DNA molecules were anchored on the surface instead of biotin molecules.

After this biotin/avidin diagnosis device was made, 1-μm fluorescent beads (F-8776 from Molecular Probes) coated with NeutrAvidin, a derivative of avidin with less nonspecific binding, were introduced into the mixing loop or ring from the input channel. Once the ring was filled, the flow was shut off right away. Because of the strong affinity between avidin and biotin, beads that were close to the biotinylated spots are "grabbed" onto them and show positive diagnostic signals.

In trials without circulation in the loop (without rotary pumping), and thus under the action of passive diffusion only, no difference of bead concentration between biotinylated spots and the rest of the channel was observed even after we waited for 30 minutes. In one experiment, the first appearance of differentiated biotinylated spots was not observed until after four hours. Most of the beads reaching within a distance of about 50 µm to the biotin pad or spot were grabbed onto it. This is a very slow process, and beads on one side of the ring would have little or no chance to get onto the (biotinylated) detection spots on the other side, a necessary condition for sensitive multiple disease diagnostics. (The diffusion constant D of 1-µm beads is $\sim 2.5 \times 10^{-9}$ cm$^2$/s (85), which is 40 times slower than 1-kpb DNA molecules (D is $\sim 1 \times 10^{-7}$ cm$^2$/s). So, 4 hours for the beads would be about 6 minutes for 1-kbp DNA molecules—still a slow process for diffusion across a 50 µm space. This particularly so in comparison with the active pumping scheme, which can cover several millimeters in 4 minutes. At least two orders of magnitude in speed can be achieved even for 1-kbp DNA molecules.)

When the peristaltic pump was activated, beads were actively moved in the loop now. Within 4 minutes, more than 80% of the beads in the central ring were quickly grabbed onto biotinylated spots, as shown in FIG. 19. Thus, the active detection scheme of the invention provides significant advantages in speed and efficiency. These devices and methods can also be advantageously used to provide improved (e.g. faster, more accurate and less costly) affinity purification systems.

6.17. Operation of A Multiparameter Chip

A few microliters (e.g. 1-50 µl) of sample are loaded from the input well and fill the fluid channels by capillary action. After the central loop is completely filled, inlet and outlet valves are closed and the peristaltic pump is turned on which move the fluid around in a circle. Instead of passive diffusion process as used in conventional chips, the target DNA in the sample is actively pumped to pass each individual complementary fragment on the surface of the substrate. With small channel dimension, 100 µm×10 µm typically, the hybridization rate and efficiency are enhanced significantly (2). The size of the channels is typically 50 to 100 µm wide and 10 µm deep. It takes only 10 seconds for a 1-kbp DNA fragment to diffuse 10 µm, all the way from the top of the channel to reach the hybridization probes at the bottom.

Moreover, since the sample will pass every probe several times, almost all target DNA will locate and hybridize with the corresponding DNA probes. Also, very little sample will be wasted during this hybridization process, which is a significant improvement over conventional passive DNA chips. Hybridization of the sample to complementary DNA probes is easily visualized under an optical microscope because the whole body of the device is transparent. Intercalating dyes, incorporation of fluorescent-labeled single nucleotides, and DNA beacons or other well-established detection schemes can be used to determine the final diagnostic results. Examples of Fluorescent dyes, particularly those that intercalate between the polynucleotide backbone, include, but are not limited to, Hoechst 33258, Hoechst 33342, DAPI (4',6-diamidino-2-phenylindole HC1), propidium iodide, dihydroethidium, acridine orange, ethidium bromide, ethidium homodimers (e.g., EthD-1, EthD-2), acridine-ethidium heterodimer (AEthD) and the thiazole orange derivatives PO-PRO, BOPRO, YO-PRO, TO-PRO, as well as their dimeric analogs POPO, BOBO, YOYO, and TOTO. The dimeric analogs, especially YOYO-1 and TOTO-1, are particular suitable for use with the present invention due to their high binding affinity for nucleic acids, which results in extremely high detection sensitivity. All of these compounds can be obtained from Molecular Probes (Eugene, Oreg.). Extensive information on their spectral properties, use, and the like is provided in Haugland, 1992, incorporated herein by reference.

Fluorescent intercalating dyes, such as YOYO-1, TOTO-1 and PicoGreen (Molecular Probes) are generally preferred because they have been demonstrated to have very high affinity to double-stranded DNA (dsDNA), large excitation cross-sections and high quantum efficiency. Their fluorescence is enhanced more than 1,000 fold when bound to double-stranded DNA (dsDNA) fragments (7,41) and they have relatively high selectivity to dsDNA compared to single-stranded DNA probe (ssDNA) (3). This high specificity and binding efficiency makes them very suitable for use as an indicator of hybridized DNA probes. Detection of individually stained dsDNA molecule using laser excitation has been reported in many places (7,8). However, an optical microscope with a mercury illumination lamp and a good CCD camera gives a reasonable justification between hybridized and non-hybridized spots as long as a few seconds of exposure is applied to obtain a similar signal level (FIG. 9).

A second inlet valve incorporated within the central hybridization loop is used because, after hybridization, this valve and the outlet valve can be opened and buffer with dye molecules can be flushed into the loop. This flushing action removes DNA molecules that do not hybridize to the DNA probes and are therefore free in the solution, but which will also stain the hybridized fragments retained in the loop. After a few minutes of incubation, the whole chip can be checked under an optical microscope as described above. A computer program can be used to determine the existence of certain disease targets by a threshold algorithm. Such algorithms are known and can be determined empirically, for example by comparing the fluorescence of a probe and sample combination (in a fluorescent reporter embodiment) with a known reference standard. Severity of the infection can also be determined according to the fluorescent intensity of the corresponding hybridization spot.

Commercially available DNA beacons are very useful as hybridization probes because if they do not hybridize with their complimentary DNA fragments (target DNA), they self-anneal to themselves and thus quench their own fluorescence. Therefore, no additional staining step is required for the final diagnosis. In-situ enzymatic labeling with fluorescent molecules is another well-known method and is obviously compatible with this device.

Polypeptides such as antibodies, antigens, receptors etc. can also be coupled to surface of the solid substrate of the chip. Examples of fluorescent dyes that can be coupled to these proteins are discussed in Example 7

6.18. Additional Embodiments

6.18.1. Additional Structures and Functions

The analysis unit of the invention, including a target loop detection region, can be combined with other structures and features on one or more chips, in an integrated design. In addition to diagnostic designs described above, additional functions can be incorporated into the integrated device as needed. Switching valves and mixing chambers can be easily designed and built into it. An automatic in-line restriction digest and denaturing process can be included before the hybridization process to save the handling labors. For an extremely small quantity of target samples, a PCR chamber can also be built into the device and the PCR reaction can be easily carried out by an external or an inline thermal cycler. The thermal cycler can also be used to apply intermittent heating to reduce non-specific binding during the hybridization process and thus obtain more accurate diagnostic results. Other enzymatic labeling and reactions can be easily incorporated into the device as described above for DNA fluorescent staining.

6.18.2. Additional Loop Channel Shapes and Geometries

Although in one preferred embodiment of the invention, illustrated in FIG. 13B, the loop channel in a microfluidic device forms a circular loop, a loop channel may actually form any shape of loop. For instance, FIG. 14 shows another exemplary embodiment where the loop channel forms a rectangular (e.g., a square) loop. The invention also provides preferred embodiments, however, wherein the loop channel forms a shape that optimizes the length of the channel through the loop. In particular, the invention provides preferred embodiments where the loop channel forms a shape that increases or maximizes the perimeter around the loop.

In more detail, in many embodiments of the invention it is desirable to increase the length of a loop channel in a microfluidic device. For example, in embodiments where the loop channel contains one or more target-molecules (for example, one or more nucleic acid probes, or one or more antibody probes, etc.), by increasing the length of a loop channel a user may simultaneously increase the number of target molecules within the loop channel, thereby increasing the number of different molecules (e.g., different nucleic acid sequences or peptides and/or polypeptides) in a sample that may be detected. Conversely, however, the microfluidic devices of the invention are preferably small (e.g., between 0.5 cm and 5.0 cm on each side, more preferably about 1 cm on each side, and between about 0.1 mm and 10 mm thick). The loop channel in a microfluidic device, therefore, preferably forms a loop enclosing a limited area. For example, in preferred embodiment the loop covers an area that is no more than about 5 cm long on either side, more preferably is no longer than about 1 cm on either side, and still more preferably is less than about 5 mm long on either side. In one particular embodiment, for example, a microfluidic device of the invention is designed for combination with standard 96-well or 384-well microtiter plates. In such embodiments, a loop channel preferably encloses an area no wider than the area of an individual microtiter well (e.g., 9 mm×9 mm for 96-well plates, or about 4.5 mm×4.5 mm for 384-well plates). It is therefore extremely desirable to configure the loop channel in a microfluidic device of this invention so that the channel forms a loop having the greatest possible perimeter within a given area. Such loop geometries allow a user to increase or maximize the length of the loop channel while simultaneously confining the loop to the very small dimensions of a microfluidic device.

FIG. 20 illustrates one exemplary embodiment of such a preferred loop channel geometry. The loop channel (201) encompasses a rectangular (e.g., square) area, and comprises a plurality of interconnected microfluidic channels (202-210). Microchannels 202-209 are a series of parallel and antiparallel channels, connected at their ends, that cover the rectangular surface area of the loop. Microchannel 210, which is perpendicular to the plurality of parallel and antiparallel channels 202-209 runs along the outer parameter on one side of the rectangular loop area.

As used here to describe channel geometries, the terms parallel and anti-parallel refer to channels that do not intersect and through which fluid travels in opposite directions (or is designed to travel in opposite directions). In more detail, a pair of microchannels is said here to be parallel if the two channels do not intersect, and either fluid flows through the channels in the same direction or the channels are designed so that fluid flows through the same channels in the same direction. A pair of microchannels is said here to be antiparallel if the two channels do not intersect, and either fluid flows through the two channels in the opposite direction or the channels are designed so that fluid will flow in opposite directions through the two channels. Thus, assuming a counter-clockwise flow of fluid through loop channel 201, fluid travels from left to right through microchannels 202, 204, 206, and 208. These channels are therefore said to be parallel to each other. Fluid travels from right to left through microchannels 203, 205, 207 and 209. These odd numbered channels are therefore antiparallel to the even number channels shown in FIG. 20. It is noted that the designation of any pair of channels in FIG. 20 as parallel or anti-parallel will not be affected by the direction of fluid flow (e.g., either clockwise or counterclockwise) through loop channel 201.

6.18.3. Additional Uses

Besides diagnosis of infectious diseases, such as tuberculosis, hepatitis and HIV, the device can be also used for detection of human genetic defects, such as cystic fibrosis, phenylketonuria and breast cancer genes (11). Moreover, multiple chemical reactions and other biological diagnosis can also be done using an appropriate set of probes and a suitable operating protocol. All of these can be considered as extensions of its applications.

6.18.4. Cell Analysis

In another embodiment, a cell or tissue sample can be processed and analyzed on an integrated chip. Cells are introduced to a first treatment chamber from a well or reservoir, on or off the chip. The first chamber includes a soap or other reagent to break or lyse the cell membrane. In a second treatment chamber the lysed cell material is treated with a digestion enzyme. In a third chamber, cell debris and protein can be washed away, leaving denatured (fragmented) DNA, which is then delivered to a target loop detection region, as described above. Also, magnetic beads coated with mixed desired probes can be used to hybridize and pull down DNA of interest, or alternatively, a pool of DNA that is not of interest, leaving other DNA for further analysis.

Besides diagnosis of infectious diseases, such as tuberculosis, hepatitis and HIV, the device can be also used for detection of human genetic defects, such as cystic fibrosis, phenylketonuria and breast cancer genes (12). Multiple chemical reactions and other biological diagnosis can also be done using an appropriate set of probes and a suitable operating protocol.

The lab-on-a-chip device of the invention uses a sample size that is several orders of magnitude less than is needed for conventional methods. Instead of many cubic centimeters or "ccs" of a blood sample, a few droplets (2-100 µl) is sufficient. The active, design of the device speeds up the detection process significantly. Multiple disease diagnostics can be done in just minutes. This device is also economical and disposable due to the material and the easy molding process.

Automatic computer control can be easily integrated by controlling the external switching of pneumatic valves via electronic driving circuits. Manual labors and chances of errors are greatly reduced. Because of the great flexibility of design and fabrication, many functions can also be incorporated into it easily.

6.19. Pump and Valve Structures

The invention provides systems for fabricating and operating microfabricated structures such as on/off valves, switching valves and pumps made out of various layers of elastomer bonded together. These structures are suitable for controlling and fluid movement in the described devices, e.g. flow control in the fluid or treatment channels and circulation in a target hybridization loop.

As described, the invention uses multilayer soft lithography to build integrated (i.e.: monolithic) microfabricated elastomeric structures. Layers of soft elastomeric materials are bound together, resulting in biocompatible devices that are reduced by more than two orders of magnitude in size, compared to conventional silicon-based devices. The preferred elastomeric material is a two-component addition cure material in which one layer (e.g. a bottom layer) has an excess of one component, while another adjacent layer has an excess of another component. In an exemplary embodiment the elastomer used is silicone rubber. Two layers of elastomer are cured separately. Each layer is separately cured before the top layer is positioned on the bottom layer. The two layers are then re-cured to bond the layers together. Each layer preferably has an excess of one of the two components, such that reactive molecules remain at the interface between the layers. The top layer is assembled on top of the bottom layer and heated. The two layers bond irreversibly such that the strength of the interface approximates or equals the strength of the bulk elastomer. This creates a monolithic three-dimensional patterned structure composed entirely of two layers of bonded together elastomer. When the layers are composed of the same material, interlayer adhesion failures and thermal stress problems are avoided. Additional layers may be added by repeating the process, wherein new layers, each having a layer of opposite "polarity" are cured and bonded together.

Thus, in a preferred aspect, the various layers of elastomer are bound together in a heterogenous (A to B) bonding. Alternatively, a homogenous (A to A) bonding may be used in which all layers would be of the same chemistry. Thirdly, the respective elastomer layers may optionally be glued together by an adhesive instead.

Elastomeric layers may be created by spin coating an RTV mixture on a mold at 2000 rpms for 30 seconds yielding a thickness of approximately 40 microns. Layers may be separately baked or cured at about 80° C. for 1.5 hours. One elastomeric layer may be bonded onto another by baking at about 80° C. for about 1.5 hours. Micromachined molds may be patterned with a photoresist on silicon wafers. In an exemplary aspect, a Shipley SJR 5740 photoresist was spun at 2000 rpms patterned with a high resolution transparency film as a mask and then developed yielding an inverse channel of approximately 10 microns in height. When baked at 2000° C. for about 30 minutes, the photoresist reflows and the inverse channels become rounded. In preferred aspects, the molds may be treated with trimethylchlorosilane (TMCS) vapor for about a minute before each use in order to prevent adhesion of silicone rubber.

In another preferred aspect, a first photoresist layer is deposited on top of a first elastomeric layer. The first photoresist layer is then patterned to leave a line or pattern of lines of photoresist on the top surface of the first elastomeric layer. Another layer of elastomer is then added and cured, encapsulating the line or pattern of lines of photoresist. A second photoresist layer is added and patterned, and another layer of elastomer added and cured, leaving line and patterns of lines of photoresist encapsulated in a monolithic elastomer structure. Thereafter, the photoresist is removed leaving flow channel(s) and control line(s) in the spaces which had been occupied by the photoresist. Tetrabutylaminonium is one photoresist etchant that is compatible with a preferred RTV 615 elastomer. An advantage of patterning moderate sized features (10 microns) using a photoresist method is that a high resolution transparency film can be used as a contact mask. This allows a single researcher to design, print, pattern the mold, and create a new set of cast elastomer devices, typically all within 24 hours.

A preferred elastomeric material is GE RTV 615 elastomer or a silicone rubber that is transparent to visible light, making multilayer optical trains possible. This allows optical interrogation of various channels or chambers in the microfluidic device. In addition, GE RTV 615 elastomer is biocompatible. Being soft, closed valves form a good seal even if there are small particulates in the flow channel. Silicone rubber is also biocompatible and inexpensive, especially when compared with a crystal silicon.

The systems of the invention may be fabricated from a wide variety of elastomers, such as the described silicon rubber and RTV 615. However, other suitable elastomeric materials may also be used. GE RTV 615 (formulation) is a vinyl silane crosslinked (type) silicone elastomer (family). The invention is not limited to this formulation, type or even this family of polymer; rather, nearly any elastomeric polymer is suitable. An important requirement for the preferred method of fabrication of the present microvalves is the ability to bond multiple-layers of elastomers together. In the case of multilayer soft lithography, layers of elastomer are cured separately and then bonded together. This scheme requires that cured layers possess sufficient reactivity to bond together. Either the layers may be of the same type, and are capable of bonding to themselves (A to A), or they may be of two different types, and are capable of bonding to each other (A to B). (Another possibility is to use an adhesive between layers.)

Given the tremendous diversity of polymer chemistries, precursors, synthetic methods, reaction conditions, and potential additives, there are a huge number of possible elastomer systems that could be used to make monolithic elastomeric microvalves and pumps. Variations in the materials used will most likely be driven by the need for particular material properties, i.e. solvent resistance, stiffness, gas permeability, or temperature stability. There are many, many types of elastomeric polymers. A brief description of the most common classes of elastomers is presented here, with the intent of showing that even with relatively "standard" polymers, many possibilities for bonding exist. Common elastomeric polymers include polyisoprene, polybutadiene, polychloroprene, polyisobutylene, poly(styrene-butadiene-styrene), the polyurethanes, and silicones. See e.g., Ser. No. 60/186,856 filed Mar. 3, 2000.

In addition to the use of "simple" or "pure" polymers, crosslinking agents may be added. Some agents (like the monomers bearing pendant double bonds for vulcanization) are suitable for allowing homogeneous (A to A) multilayer soft lithography or photoresist encapsulation; complementary agents (i.e. one monomer bearing a pendant double bond, and another bearing a pendant Si—H group) are suitable for heterogeneous (A to B) multilayer soft lithography.

Materials such as chlorosilanes such as methyl-, ethyl-, and phenylsilanes, for example polydimethylsiloxane (PDMS) such as Dow Chemical Copr. Sylgard 1,82, 184 or 186, or alipathic urethane diacrylates such as (but not limited to) Ebecryl 270 or Irr 245 from UBC Chemical may also be used. Elastomers may also be "doped" with uncrosslinkable polymer chains of the same class. For instance RTV 615 may be diluted with GE SF96-50 Silicone Fluid. This serves to reduce the viscosity of the uncured elastomer and reduces the Young's modulus of the cured elastomer. Essentially, the crosslink-capable polymer chains are spread further apart by the addition of "Inert" polymer chains, so this is called "dilution". RTV 615 cures at up to 90% dilution, with a dramatic reduction in Young's modulus.

The described monolithic elastomeric structures valves and pumps can be actuated at very high speeds. For example, the present inventors have achieved a response time for a valve with aqueous solution therein on the order of one millisecond, such that the valve opens and closes at speeds approaching 100 Hz. The small size of these pumps and valves makes them fast and their softness contributes to making them durable. Moreover, as they close linearly with differential applied pressure, this allows fluid metering and valve closing in spite of high back pressures.

In various aspects of the invention, a plurality of first flow channels pass through the elastomeric structure with a second flow channel, also referred to as an air channel or control line, extending across and above a first flow channel. In this aspect of the invention, a thin membrane of elastomer separates the first and second flow channels. Movement of this membrane (due to the second flow channel being pressurized) will cut off flow passing through the lower flow channel. Typically, this movement is downward from a the interface with top control layer into an closing an underlying first flow channel.

A plurality of individually addressable valves can be formed and connected together in an elastomeric structure, and are then activated in sequence such that peristaltic pumping is achieved. In other optional preferred aspects, magnetic or conductive materials can be added to make layers of the elastomer magnetic or electrically conducting, thus enabling the creation of elastomeric electromagnetic devices.

In preferred aspects, channels of the invention have width-to-depth ratios of about 10:1. In an exemplary aspect, fluid and/or air channels have widths of about 1 to 1000 microns, and more preferably 10-200 microns and most preferably 50-100 microns. Preferred depths are about 1 to 100 microns, and more preferably 2-10 microns, and most preferably 5 to 10 microns.

In preferred aspects, an elastomeric layer has a thickness of about 2 to 2000 microns, and more preferably 5 to 50 microns, and most preferably 40 microns. Elastomeric layers may be cast thick for mechanical stability. In an exemplary embodiment, one or more layers is 50 microns to several centimeters thick, and more preferably approximately 4 mm thick. Membrane separating fluid and air channels has a typical thickness of about 30 nm. In one embodiment the thickness of one elastomeric layer (e.g. at top or control layer) is about 10 times the thickness of an adjacent layer (e.g. a fluid or bottom layer).

A typical RTV valve of the invention is 100 µm×100 µm×10, connected to an off-chip pneumatic valve by a 10-cm-long air tube. In one example, the pressure applied on the control line is 100 kPa, which is substantially higher than the approximately 40 kPa required to close the valve. Thus, when closing, the valve in this example is pushed closed with a pressure 60 kPa greater than required. When opening, however, the valve is driven back to its rest position only by its own spring force, which is less than or equal to about 40 kPa). A signal to open or close the valve is effected by changing the pressure accordingly. In this example there is a lag between the control signal and the control pressure response, due to the limitations of the miniature valve used to control the pressure. To accommodate this lag, these exemplary valves run comfortably at 75 Hz when filled with aqueous solution. If one used another actuation method which did not have an opening and closing lag, this valve would run at about 375 Hz. Note also that the spring constant can be adjusted by changing the membrane thickness; this allows optimization for either fast opening or fast closing.

The flow channels of the present invention may optionally be designed with different cross sectional sizes and shapes, offering different advantages, depending upon their desired application. For example, the cross sectional shape of a lower fluid channel may have a curved upper surface, either along its entire length or in the region disposed under an upper air channel or cross channel. In certain embodiments a curved upper surface facilitates valve sealing. In an alternate aspect, the bottom of a fluid channel is rounded such that its curved surface mates with the curved upper wall upon valve closure.

6.20. Arrayable Rotary Mixer

This example describes a preferred embodiment of a microfluidic device. In particular, the example describes a microfluidic device that has a plurality (i.e., at least two) of hybridization or target loops, with the fluid flow in each hybridization or target loop being driven by a peristaltic pump. Each target loop in the device may be connected to a separate input well and/or a separate output well (e.g., via separate input and/or output channels) to permit simultaneous loading and analysis of several samples in the microfluidic device.

Alternatively, several of the hybridization or target loops may be connected to common input and/or output wells; for example, by common input and/or output channels that branch into several branch channels, with each branch channel connecting to a different hybridization or target loop in the microfluidic device. A single sample (e.g., a single biological sample, such as a nucleic acid sample from a single patient) may then be loaded into the microfluidic device via an input well, and a plurality of different assays may be simultaneously performed on the sample. In particular, each hybridization or target loop may perform a separate biological assay, such as detecting the presence of a different nucleic acid (e.g., the presence of a different gene or a different mutation of a particular gene or genes).

In particularly preferred embodiment, such a microfluidic device may be combined with standard microtiter plates, for example standard 96-well or 384-well microtiter plates, that are widely used in most biological laboratories. Such a device will then be compatible with most existing loading and/or reading systems of loading and analyzing biological samples.

FIGS. 21A and 21B illustrate two preferred embodiments of single hybridization or target loops and their associated peristaltic pumps which can be arrayed to form a microfluidic device of this example. The device comprises a fluid or "treatment" layer (bottom layer) containing the loop channel (2101) and an air channel or "control" layer (top layer) having a plurality of air channels (2102). The plurality of air channels in the air channel layer form microvalves (2103) where each air channel intersects the loop channel.

In this example, the fluid channels are about 300 µm wide and about 30 µm deep. Suitable fluid channels are identical to those described elsewhere in this specification for microfluidic devices (see, e.g., Section 6.14). Typical fluid channel dimensions include those ranging from about 5-1000 μm wide and from about 1-50 μm deep, more preferably about 10-200 μm wide and about 2-30 μm deep. A preferred depth is about 10 μm.

The exemplary loop channels shown in FIGS. 21A and 21B form loops having the geometry described in Section 6.18.2, supra, and illustrated in FIG. 20. However, the loop channels may form any shape of loop, including any of the particular shapes described in this specification. For example, the hybridization or target loops may be circular loops (as shown in FIG. 13B) or they may be rectangular (e.g., square) loops (as shown in FIG. 14). Loops having a geometry as described in Section 6.18.2 (e.g., the geometry illustrated in FIG. 20) are preferred.

The air channels (2102) in this example are about 100 to 300 μm wide and about 30 μm deep. Suitable air channel dimensions include those ranging from about 10-1000 μm wide (more preferably about 50-200 μm wide) and about 2-50 μm deep (more preferably about 10-50 μm deep). A preferred particularly depth is about 20 μm. In this embodiment, the air channels are preferably parallel (or antiparallel) and do not intersect. The air channels preferably run across the entire target or hybridization loop formed by the loop channel (i.e., they completely traverse the area encompassed by the loop).

In preferred embodiments, the loop channels in a microfluidic device have at least one, and more preferably a plurality of channel supports (2104). In general, a channel support (2104) is located in the loop channel at a point where an air channel (2102) intersects the loop channel. The channel support supports the membrane above the fluid channel (i.e., between the air channel layer and the fluid channel layer) without blocking the fluid channel; e.g. fluid can flows through the fluid channel around the channel support. Where an air channel intersects a fluid channel at a point (2103) not having a channel support, the membrane between the air and fluid channels is not pushed down by application of a sufficient air pressure in the air channel. Thus, application of the air pressure causes the air channel to function as a microvalve and restrict or close the fluid channel at point 2103. However, where an air channel intersects a fluid channel at a point having a channel support 2104, the channel support prevents the air channel from restricting or closing the fluid channel. Thus, these points do not function as microvalves.

Microchannels having channel supports may be readily obtained, e.g., using any of the microfabrication techniques described supra. For example, in preferred embodiments individual layers for a microfluidic device are prepared from fluid molds fabricated on silicon wafers using photolithography (see, e.g., Sections 6.9 and 6.13.2, supra). In such embodiments, standard micromachining-techniques may be used, e.g., to create a negative master mold out of a silicon wafer. The mold may have a positive channel contour (see, e.g., FIG. 8) with a "hole" in its center. Curing a silicone elastomer (e.g., RTV 615) over such a mold thereby creates a microfluidic layer with a negative channel having a channel support therein. In other embodiments, microchannel supports may be manufactured in the control layer (e.g., in air channels) instead of or in addition to the fluid channels. Alternatively, functionally equivalent channel supports may be obtained by decreasing the width of a fluid channel, an air channel or both at a point where the fluid channel and the air channel intersect.

The microchannel supports may be any shape. However, circular or square support shapes are preferred. Preferably, the supports are about 2-100 μm wide, and are more preferably about 5-30 μm wide. The skilled artisan will further appreciate that the invention may include embodiments where multiple supports are located at a channel intersection (e.g., two or more, three or more, four or more, or five or more supports). A skilled artisan can readily determine appropriate spacing between multiple supports according to the channel depth and actuation pressure (e.g. the force per unit area) in the air channel of a particular microfluidic device. However, typical support spacing is between about 5-500 μm, and is more preferably between 10-100 μm.

FIG. 21A shows one embodiment of an arrayble loop channel which is traverse by three parallel air channels (2102). Although each channel typically intersects the loop channel at two or more points, only one intersection point is not blocked or occluded by a channel supports. Thus, each air channel intersects a loop channel at only one microvalve (2103).

An alternative embodiments of an arrayble loop channel is illustrated in FIG. 21B. The loop channel of this particular embodiment is traversed by four parallel air channels (2102) which have a wider width (e.g., about 20-1000 μm) at points where they intersect the loop channel to form microvalves (2103). However, the air channels have narrower widths (e.g., about 5-100 μm) at other points where they intersect the loop channel (2101), thereby forming structures that function as "channel supports" (2104) and prevent restriction or closing of the fluid channel when pressure is applied to the air channels. In the particular embodiment illustrated in FIG. 21B, the air channels may also traverse the loop channel along channel walls and/or between parallel and antiparallel microchannels (2105 and 2106). Preferably, the air channels are narrower (e.g., between about 5-100 μm wide) and, more preferably, are no wider than the separation distance between the parallel and antiparalell channels.

Although any number of air channels may traverse or intersect an arrayble loop channel, there are preferably at least three air channels traverse a given loop channel to form at least three microvalves. There may, however, be 4, 5, 6, 7 or more air channels intersecting a loop channel to form 4, 5, 6, 7 or more microvalves.

FIGS. 22A and 22B illustrate an exemplary microfluidic device that comprises arrays of target or hybridization loops 2201. FIG. 22A shows one preferred embodiment of such a device that comprises an array of 96 target or hybridization loops which are compatible with the wells of a standard 96-well microtiter plate. FIG. 22B is an exemplary "4-cell" microfluidic device (i.e., a microfluidic device comprising four target or hybridization loops).

As with other microfluidic devices of this invention, these microfluidic devices comprise a fluid channel or "treatment" layer (bottom layer) that contains the microfluidic channels (including the loop channels), and an air channel layer or "control" (top layer). The air channel layer in the device comprises a plurality of parallel air channels (2202) that each traverse a plurality of the loop channels (2201). As each air channel 2202 traverse a loop channel 2201 it preferably intersects the loop channel at one point that does not have a channel support, thereby forming a microvalve (2203). The fluid layer in such microfluidic devices preferably comprises one or more additional fluid channels (2204), such as an inlet channel and/or an outlet channel feeding into each loop channel of the device. The inlet and/or outlet channels may be in fluid connection with a single inlet well or outlet well (e.g., for feeding a single sample into each of the target or hybridization loops). Alternatively, the inlet channel, the outlet channel or both the inlet and the outlet channels for each target or hybridization loop may be in fluid connection with a separate sample inlet or with a separate sample outlet (e.g., so that a separate sample may be loaded and/or analyzed in each target or hybridization loop).

As with other embodiments of this invention, target molecules (e.g., DNA hybridization probes or antibody probes) are preferably laid down along the loop channels, e.g., on a glass substrate (2205) which lies beneath the fluid channel layer. Preferably, different target molecules (e.g., DNA hybridization probes having different nucleic acid sequences) are laid down along each loop channel. For example, as with the embodiments described in Section 6.13, supra, the channels of the microfluidic devices are preferably exposed to a common face of a chip. The multiplayer assembly (for example an RTV assembly, as described in Section 6.13 supra) may be aligned and bonded to a substrate (e.g., a glass or other transparent substrate) so that a hermetic seal forms between the fluid channels and the substrate. The substrate is preferably patterned in advance with one or more different target molecules (e.g., one or more sets of DNA or antibody probes) at positions corresponding to the loop channels (2201).

A variety of additional microfluidic structures and functions may also be incorporated in such microfluidic devices, including any of the other microfluidic structures and functions described herein. For example, FIG. 22B illustrates a microfluidic device having additional channels which may be used, e.g., for the delivery of common samples, reagents, buffers or other chemicals to the target or hybridization loops. Other channels may be included, e.g., for the removal of sample, reagents, buffers, etc. from the target or hybridization loops (e.g. waste channels). Microvalves and/or channel supports may also be microfabricated and/or incorporated into such other channels.

In particularly preferred embodiments, a microfluidic device such as the one shown in FIG. 22A is readily designed so that the spacing and dimensions of the target loop channels correspond to and/or are compatible with the wells of a standard microtiter plates (e.g., a standard 96-well or 384-well plate). Each well of a microtiter plate can be loaded with target molecules (preferably different target molecules) and the fluid channel layer for the device are laid over and, optionally, bonded to the microtiter plate.

Using such microfluidic devices, the amount of sample volume needed for analysis is greatly reduced. For example, in preferred embodiments sample volumes between about 1-500 µl, and more preferably between about 1-100 µl, can be loaded into a sample well of the microfluidic device. In other embodiments, sample volumes of less than 1 µl can be used. For example, in preferred embodiments the sample volume may be from about 1-1000 nl, more preferably between about 1-500 nl, still more preferably between about 1-100 nl, and even more preferably from about 1 nl to about 10 nl, about 20 nl, or about 50 nl. In particularly preferred embodiments, the sample volume loaded into a microfluidic device may be as low as 500 pl or less (e.g., as low as 200 pl, 100 pl, 50 pl, or less). In addition, because the pumps and valves of microfluidic devices in this invention have negligible volumes, they are able to transport fluids at up to a few femtoliters per second, and more preferably at up to a few nanoliters per second.

Thus, smaller volumes of sample may be analyzed in parallel in large numbers of microtiter wells. Accordingly, in one embodiment, a microfluidic device of the invention comprises an array of 96-loop channels and/or are compatible with a 96-well plate. In another preferred embodiment, a microfluidic device of the invention comprises an array of 384 loop channels and/or is compatible with a 384-well plate. In other embodiments, the devices comprise even more numbers of loop channels and may be used with even larger microtiter plates. For example, in another preferred embodiment the device comprises 1536 loop channels and/or is compatible with a 1536-well plate.

6.21. Rotary Puming and Inline Mixing

This example presents experimental data that were obtained using a microfluidic device having a chip architecture as described in Section 6.13, supra. Specifically, the microfluidic device used in this example is one having a rotary loop and driven by a peristaltic pump. The data presented here confirm that fluids may be rapidly mixed using such a device. As such, the devices of this invention offer superior results compared to similar devices that are currently available.

6.21.1. Device Design and Fabrication

The microfluidic device used in this example comprised the same architecture and was identical to the device illustrated in FIG. 14 and described in Section 6.13, above. FIG. 17 is a schematic diagram of the device used in these experiments. A photograph of that device is provided in FIG. 13. Briefly, the device consists of two layers: a first or "bottom" layer comprising fluid channels, and a second or "top" layer comprising pneumatic actuation channels. The bottom fluid layer also has two sample inputs (labeled $in_1$ and $in_2$ in FIG. 17), a mixing T-junction, a central circulation loop (also referred to here as a "rotary loop"), and an output channel. The loop diameter is 2.4 mm, while the channel dimensions in this exemplary device are 100 µm wide by 10 µm deep. The top layer has several stand alone actuation channels, which can be pressured or vented to atmosphere. Any intersection of a top air channel with a bottom fluid channel forms a microvalve. The valve is closed when the air channel is pressurized, and is released otherwise. Several inlet and outlet valves were built in to control the flow of each individual fluid component. When a series of on/off actuation sequencers (for example, 001, 011, 010, 110, 100, 101) are applied to the air lines, the fluid can be peristaltically pumped through the loop in a chosen direction, which can be either clockwise or counter-clockwise (see, also, Section 6.14 for detailed explanation of such actuation sequences). The higher the actuation frequency, the faster the fluid flows or "rotates" through the loop.

The device was fabricated using multilayer soft lithography techniques that are described here in Section 6.13.2, supra. See, also, the recent publication of Unger et al. (76) and by Chou (88). See, also, U.S. provisional patent application Ser. No. 60/249,362 filed on Nov. 16, 2000. Briefly, mother molds for top and bottom layer were first fabricated on silicon wafers by photolithography with photoresist (Shipley SJR 5740). Channel heights were controlled precisely by the spin coating rate. After UV exposure and development, photoresist channels were formed. Heat reflow process and protection treatment were applied (10). Then, mixed two-part silicone elastomer (GE RTV 615) was spun onto the bottom mold and poured onto the top mold, respectively. Again, spin coating was used to control the thickness of the bottom polymeric fluid layer. After baking in the over at 80° C. for 25 minutes, the partially cured top layer was peeled off from its mold, aligned and assembled with the bottom layer. A 1.5-hour final bake at 80° C. was applied to bind these two layers irreversibly. Once peeled off from the bottom silicon mother mold, this RTV device was sealed hermetically to a glass cover slip.

6.21.2. Rotary Pumping and Inline Mixing

Fluid in a microfabricated rotary loop of this invention can be pumped peristaltically when a proper actuation sequence is applied, as described supra. To demonstrate such pumping, the central loop was loaded with 2.5 µm diameter fluorescent beads. Valves regulating flow into or out of the loop (i.e., the inlet and outlet valves) were closed, and the peristaltic pump was turned on by applying an appropriate actuation sequence as described above. Clear circulation of the beads around the loop could be visualized without any net flux into or out of the loop. By simply controlling the frequency of the actuation sequence applied with the peristaltic pump, the speed or flow-rate of particles around the loop could be adjusted. Similarly, the rotation direction could be changed simply by reversing the actuation sequence.

In a microfabricated device of this invention, sample may be loaded into a microfabricated rotary loop (e.g., through one or more inlet channels) and quickly mixed using the rotary pump. Without being limited to any particular theory or mechanism of action, it is understood that as two or more different fluids rotate in the same loop, fluid at the center of the loop channel flows faster than fluid located at the channel's edge. As a result, it is expected that the interface between the two fluids will continue to stretch as the fluids circulate, until each fluid becomes a long, thin stream that wraps around the other fluid. Components of the different fluids can then cross the interface between the fluids by diffusion, allowing the fluids to quickly and efficiently mix. By contrast, other microfluidic devices that are currently available typically inject different fluids into a chamber, and wait for them to mix by slow diffusion. Thus, microfabricated devices having a rotary loop of this invention offer particular advantages over existing devices.

To demonstrate the device's ability to effectively and efficiently mix different fluid components, experiments were performed in which the microfluidic device schematically illustrated in FIG. 17 was used for "fixed-volume mixing" and "continuous-flow mixing." The results from these two experiments, which are similar to the experiments described, above, in Section 6.15, are presented herebelow.

Fixed-volume Mixing. The term "fixed-volume mixing", as used here, refers to instances in which two different solutions (for example, of a sample and a reagent) of fixed volume are mixed completely before being directed to another stage of processing. To demonstrate the ability of a microfabricated rotary loop to mix fluids under these circumstances, a solution of the fluorescent dye FITC was loaded into one of the device's input channels (in$_2$), and a solution of 1 µm fluorescent beads was loaded into the other input channel (in$_2$). Because of laminar flow and the slow diffusion rate, these two streams of fluid did not mix as they entered the T-junction of the device. Instead, each fluid remained confined to one half of the flow channel, and the two fluid flowed side by side into the central loop. Upon entering the central loop, the two fluids split into their two distinct parts and met again at the bottom of the loop, as shown in FIG. 18A. Thus, one half of the central loop was filled with a solution containing the FITC dye, while the other half filled with a solution containing the fluorescent beads.

Once the central loop filled with fluid as described above, the peristaltic pump was activated with the appropriate actuation sequence and at a frequency of 30 Hz. After only 30 seconds of pumping, both the fluorescent dye and the beads were uniformly distributed throughout the whole central loop, as shown in FIG. 18B. Thus, a microfabricated rotary loop of this invention can be used to rapidly mix two or more different reagents; and can be particularly useful when one or more of the different components have slow diffusion constants; for example, with a DNA sample to be mixed with hybridization beads or cells to be mixed with plasmid-lipid complexes.

Continuous-flow Mixing. The term "continuous-flow mixing" is used here to describe mixing that takes place as two or more fluids continuously flow down a micro-channel. Thus, unlike the fixed-volume mixing experiments described above, continuous-flow mixing refers to a situation where inlet and outlet channels to a rotary loop are not closed so that solution flows continuously through the loop. A second experiment was performed to demonstrate the ability of a microfabricated loop to mix such a continuous flow of fluids. This second experiment was identical to the fixed-volume mixing experiment described above, except that the inlet and outlet channels were left open so that the bead and dye solutions flowed continuously through the loop at a flow rate of about 2 mm/s.

As in the fixed volume mixing experiment (supra), the two fluids did not mix as they entered the T-junction and, upon entering the loop, split into their two distinct parts and met again at the bottom of the loop (FIG. 23A). When the rotary pump was activated, complete dye mixing was observed (FIG. 23B). Partial mixing of the extremely slow 1 µm beads also occurred so that about one quarter (i.e., approximately 25%) of the beads were sent to the other side of the central loop after passing through the continuous-flow rotary mixer only once.

To quantify the level of mixing, 119 video frames were analyzed to count beads within a window channel, and to note their location. These data are shown in FIGS. 23C and 23E for experiments where the rotary pump was inactive and mixing occurred by diffusion, and in FIGS. 23D and 23F for experiments where the rotary pump was activated. FIGS. 23C and 23D show a plot indicating the location where fluorescent beads were observed across the channel width (the horizontal or "X" axis) and along a short section of the outlet channel length (the vertical or "Y" axis) in the analyzed frames. FIGS. 23E and 23F plot the accumulated distribution of fluorescent beads observed across the channel width ("X").

The quality of continuous-flow mixing in such a rotary loop depends strongly on the ratio of the overall flow rate and the pump rate. Thus, the mixing quality can be optimized for a particular application by either lowering the overall flow rate with which fluid is introduced into the loop, by widening and/or lengthening the rotary mixer loop, or by increasing the rotary mixing speed (e.g., by increasing the actuating sequence for the peristaltic pump).

Estimating rotary flow mixing times. Without being limited to any particular theory or mechanism of interaction, a simple model is presented to estimate the mixing effect of the rotary flow in a microfluidic device of this invention. In particular, the model provides formulas that are useful, e.g., to estimate the time required for effective mixing using a microfluidic device of the invention with active rotamer pumping (for example, in the fixed volume and/or continuous volume mixing experiments described above).

FIG. 24 provides a simplified schematic for an exemplary microfabricated central loop. The microfabricated channel forming the loop has a radius $r_0$, and forms a circular loop of radius R.

As described above, when two separate fluids (referred to here as fluids A and B, respectively) enter the loop through a microfabricated inlet channel, they are not mixed. Instead, each fluid is confined to one half of the flow channel so that the two fluids flow side by side into the loop. Upon entering the loop the two fluids separate. One fluid (e.g., fluid A) travels counterclockwise through the loop, while the other fluid (e.g., fluid B) travels clockwise through the loop until the two fluids meet again at the bottom of the loop (i.e., opposite the inlet channel). Thus, in the simple model described here fluid A initially fills the loop over an angular range of 0 to $\pi$ radians (i.e. 0 to 180°). Fluid B initially fills the loop over an angular range of $\pi$ to $2\pi$ radians (i.e., from 180° to 360°).

As fluid is pumped through the loop channel, it experiences a differential velocity. In particular, fluid near the channel's edge experiences a dragging force from the channel wall, and therefore flows at a slower speed. Fluid near the center of the loop channel experiences less drag or resistance, and therefore travels at a faster speed. Accordingly, during active pumping the flow velocity v at a distance r from the channel center is estimated in the present model by $$v = v_0 \left(1 - \left(\frac{r}{r_0}\right)^2\right) \quad \text{(Eq. 6.21.A)}$$

where $v_0$ is the maximum fluid velocity (i.e., the velocity at r=0, the center of the fluid channel). Similarly, the angular velocity of fluid flow through the loop $\omega$=v/R is estimated by the formula $$\omega = \omega_0 \left(1 - \left(\frac{r}{r_0}\right)^2\right) \quad \text{(Eq. 6.21.B)}$$

where $\omega_0$=$v_0$/R (i.e., the angular velocity at r=0, the center of the channel As fluid is pumped through the loop for a time t, the front or boundary between fluids A and B travels through an angular distance given by $\omega t \cdot \text{mod}(2\pi)$.

From Equation 6.21B, above, it is easy to see that when the fluid center moves through an angular distance $\omega_0$ t=$\pi$, the center of the front between fluids A and B will have traversed one-half turn around the loop. However, that part of the front adjacent to the channel wall will not have moved at all. Thus, at time t=$\pi/\omega_0$, the greatest distance over which fluids A and B must diffuse to mix is simply equal to the channel radius, $r_0$. From this logic, it can be seen that once the front at a distance r from the channel center has traversed one-half turn around the loop, the greatest diffusion distance l is simply the distance to the channel wall; i.e., l=$r_0$−r. The diffusion distance may therefore be estimated by solving Equation 6.21.C, below, for $r_0$−r.

$$\omega t = \omega_0 \left(1 - \left(\frac{r}{r_0}\right)^2\right) t = \pi, \quad \text{(Eq. 6.21.C)}$$

This equation has an approximate solution given by:

$$l = r_0 - r \approx \frac{\pi r_0}{\omega_0 t} \quad \text{(Eq. 6.21.D)}$$

which may be rewritten in the more convenient form provided in Equation 6.21.E, below, where $l_0$=$r_0$, and k=$\omega_0/\pi$=$v_0$/R$\pi$.

$$l = \frac{l_0}{kt} \quad \text{(Eq. 6.21.E)}$$

In this latter expression, k is therefore a constant coefficient that depends upon the total distance around the loop (i.e., $2\pi$R) and the pumping speed.

The time T required for an object to diffuse across a distance l can be provided by the equation $$\tau = \frac{l^2}{2D} \quad \text{(Eq. 6.21.F)}$$

where D is the object's diffusion constant. If rotary pumping occurs, however, the diffusion distance l is given by Equation 6.21.E, above. Thus, by substituting the expression for l given in Equation 6.21.E and solving Equation 6.21.F for $\tau$=t, the rotary mixing time for effectively mixing two fluids A and B can be estimated as:

$$\tau = \left(\frac{r_0^2}{2k^2 D}\right)^{1/3} \quad \text{(Eq. 6.21.G)}$$

In contrast, other devices typically mix fluids by passive diffusion across the channel radius, $r_0$. However, such diffusion requires a time period given by the equation:

$$\tau = \frac{r_0^2}{2D} \quad \text{(Eq. 6.21.H)}$$

By comparing Equations 6.21.G and 6.21.H, supra, it is apparent that mixing by rotamer pumping in a microfluidic device of this invention greatly improves upon other devices that are presently available. In particular, the required mixing time in a rotamer loop of this invention is much less sensitive to both the channel width $r_0$ and the diffusion constant D. For large objects (e.g, proteins, beads, virions, cells, etc.), the diffusion constant is typically between $10^{-5}$ and $10^{-8}$ cm$^2$/s. Thus, whereas mixing of such objects by passive diffusion will typically require a time factor on the order of $10^3$, the time factor required for mixing by active rotary pumping in a device of this invention reduced by two orders of magnitude, i.e., to a factor of only 10.

6.22. Surface Binding Assay Using a Multiparameter Chip

This example describes experiments that are similar to those described in Sections 6.14 and 6.16, supra, and that illustrate the utility of a microfabricated rotary loop in binding assays. Specifically, an exemplary assay is demonstrated in which avidin labeled beads bind to biotin in the central loop of a microfabricated device. These data show that using such a rotamer pump greatly shortens the time required for binding to occur, thereby offering, improved results over traditional devices where binding is drive by simple diffusion.

6.22.1. Surface Patterning of a Microfluidic Chip

The particular microfluidic device described, supra, in Section 6.21 was also used in the binding assays described here. However, for these binding experiments the device was hermetically sealed to a glass cover slip that had been chemically patterned with biotin to form a binding-assay substrate. Soft lithographic techniques for chemical patterning are well known in the art and have been described, e.g., for antibody recognition in microfluidic network (79) and for microcontact printing of self-assembled monolayers (89). For these experiments an elastomeric print head was designed having a radial pattern of fluidic channels. The print head was attached to a glass cover slip whose surface had been functionalized in advance with carboxyl groups. A biotin-amine conjugate and coupling solution (comprising EDC and Sulfo-NHS) were deposited in a well in the middle of the print head, which then filled the microfluidic spokes by capillary action. As a result, the print head generated a crude pattern of biotin derivatized, radial "spokes" on the cover slip. More complicated patterns of derivatized micronetworks can be readily designed by actively pumping reagents through an elastomeric print head in arbitrary patterns.

After the biotin coupling reaction was complete, channels in the print head were flushed with buffer, the print head was removed, and the microfluidic device was attached to the cover slip as described in Section 6.21, supra. The resulting microfluidic device is shown schematically in FIG. 17, and included a central loop (105) with eight 100 μm by 100 μm biotin spots or "pixels" (110) in the regions where the biotin derivatized spokes intersected the loop channel. The total volume in the central rotary-pump reaction chamber was 7.54 nanoliters.

6.22.2. Surface Binding Assay

After a biotin surface patterned microfluidic device was prepared as described, supra, 1 μm fluorescent beads (Molecular Probes) coated with NeutrAvidin (a derivative of avidin with less nonspecific binding) were introduced into the central loop from the input channel. Once the loop was filed, input and output microvalves were closed and the peristaltic rotary pump was activated at a cycling frequency of 10 Hz. Within four minutes, more than 80% of the NeutrAvidin coated beads had bound to the biotinylated spots, as shown in FIG. 19.

Control experiments were also performed in which the peristaltic rotary pump was not activated. Thus, in these control experiments binding to the biotin spots was driven only by the diffusion of the NeutrAvidin labeled beads. However, this is expected to be an extremely slow process due to the slow diffusion constant of those beads (about $2.5 \times 10^{-9}$ cm$^2$/s). Indeed, it took 4 hours before the fluorescent signal from the beads was localized to the biotinylated spots. By this time, most beads with about 50 μm of a biotinylated spot had bound thereto. Clearly therefore, binding by diffusion alone is an extremely slow process and beads on the other side of the loop from a detection spot would never have the chance to bind thereto, as is necessary for multiplexed surface binding assays. Thus, use of a rotary loop and pump of the present invention greatly improved the reaction kinetics, reducing the reaction time by a factor of at least 60.

In summary, an active DNA diagnosis chip using multilayer soft lithography is described. DNA fragments are patterned on a glass substrate with appropriate surface chemistry combinations and by using elastomeric fluidic channels. A monolithic elastomeric diagnosis device is aligned and attached to the derivatized surface. DNA samples are brought in, e.g. to fluid channels, are circulated several times in a hybridization loop containing probes bound to an aligned and communication surface, and sample fluid (e.g. with non-binding. DNA) is then expelled from an outlet, under valve control. Fluorescent dye, used to determine, detect, measure or image the hybridization, is brought in from the same or another input channel. Fast mixing can also be done with the active pumping mechanism. Laminar flow and diffusion consideration in this low-Reynolds number regime can be overcome easily by the active pumping agitation.

While the invention has been described with reference to specific methods and embodiments, it will be appreciated that various modifications may be made without departing from the invention.

7. BIBLIOGRAPHY AND REFERENCES CITED

The following Bibliography provides the complete citations to the references cited in the above text. The references are provided merely to clarify the description of the present invention and citation of a reference either in the below Bibliography or in the specification above is not an admission that any such reference is "prior art" to the invention described herein.

Each reference cited in this application, including the references listed in the below Bibliography and any other references cited in the above specification, is incorporated herein, by reference, in its entirety and to the same extent as if each references was incorporated by reference individually in the above specification.

1. G. L. Mandell, J. E. Bennett and R. Dolin, "Mandell, Douglas, and Bennett's principles and practice of infectious diseases," *Churchill Livingstone*.
2. Fodor, et al., "Array of oligonucleotides on a solid substrate," U.S. Pat. No. 5,445,934 (1995)
3. Chee, et al., "Arrays of nucleic acid probes on biological chips," U.S. Pat. No. 5,837,832 (1998).
4. Graham Ramsay, "DNA chips: State-of-the art," *Nature Biotechnology*, Vol. 16, pp. 40-44, 1998.
5. Joel S. Bader, et al., "DNA transport by a micromachined Brownian ratchet device," *PNAS*, Vol. 96 (23), pp. 13165-13169, 1999.
6. Marc A. Unger, Hou-Pu Chou, Todd Thorsen, Axel Scherer and Stephen Quake, "Monolithic microfabricated valves and pumps using multi-layer soft lithography," submitted, November, 1999.
7. Richard P. Haughland, "Handbook of Fluorescent Probes and Research Chemicals," *Molecular Probes*.
8. Alan Van Orden, Richard A. Keller, W. Patrick Ambrose, "High-throughput flow cytometric DNA fragment sizing, "*Anal. Chem.*, Vol. 72 (1), pp. 37-41, 2000.
9. Hou-Pu Chou, Charles Spence, Axel Scherer, Stephen Quake, "A microfabricated device for sizing and sorting DNA molecules," *PNAS*, Vol. 96, pp. 11-13, 1999.
10. V. L. Singer, L. J. Jones, S. T. Yue and R. P. Haugland, "Characterization of PicoGreen reagent and development of a fluorescence-based solution assay for double-stranded DNA quantitation," *Analytical Biochemistry*, Vol. 249, pp. 228-238, 1997.
11. M. U. Kopp, A. J. de Mello and A. Manz, "Chemical amplification: Continuous-flow PCR on a chip," *Science*, Vol. 280 (5366), pp. 1046-1048, 1998.
12. J. G. Hacia, L. C. Brody, M. S. Chee, S. P. A. Fodor, F. S. Collins, "Detection of hetero-zygous mutations in BRCA1 using high density oligonucleotide arrays and two-colour fluorescence analysis", *Nature Genetics*, Vol. 14 (4), pp. 441-447, 1996.
13. Thomas S. M., Genomics: the implications for ethics and education". Br Med Bull, 55(2):429-45, 1999.
14. J. P. Nolan, L. A. Sklar, *Nature Biotechnology* 16, 63-3 (1998).

15. P. J. Crosland-Taylor, *Nature (London)* 171, 37 (1953).
16. U.S. Pat. No. 2,656,508 issued to Coulter (1949).
17. L. A. Kamensky, M. R. Melamed, H. Derman, *Science* 150, 630 (1965).
18. A. Moldavan, *Science* 80, 188 (1934).
19. M. A. Van Villa, T. T. Trujillo, P. F. Mullaney, *Science* 163, 1213 (1969).
20. M. A. Van Villa, et al., *A fluorescent cell photometer: a new method for the rapid measurement of biological cells stained with fluorescent dyes*. (Biological and Medical Research Group of the Health Division, LASI., 1997).
21. M. J. Fulwyer, *Science* 156, 910 (1974).
22. H. M. Shapiro, *Practical Flow Cytometry* (Wiley-Liss Inc., New York City, 1995).
23. M. R. Melamed, T. Lindmo, M. I. Mendelsohn, *Flow Cytometry and Sorting* (Wiley-Liss Inc., New York City, 1990).
24. G. Whitesides, Y. Xia, *Angewandte Chemie International Edition* 37 (5), 550 (1998).
25. P. H. Li, D. J. Harrison, *Analytical Chemistry* 69, 1564 (1997).
26. S. Fiedler, et al. *Analytical Chemistry* 70, 1909-1915 (1998).
27. L. A. Sklar, *Proc. SPIE* 3256, 144 (1998).
28. H. P. Chou, A. Scherer, C. Spence, S. R. Quake, Proc. Natl. Acad. Sci. USA 96: 11-13 (1998).
29. A. Ashkin, J. M. Dziedzic, *Science* 235, 1517 (1987).
30. A. Ashkin, J. M. Dziedzic, *Nature* 330, 769 (1987).
31. T. N. Buican, M. J. Smyth, H. A. Verissman, *Applied Optics* 26, 5311 (1987).
32. C. Spence, S. R. Quake, "Transformation of cells with DNA sorting on microchips."; personal communication, 1998.
33. R. V. Hare, "Polyvinylsiloxane impression material."; U.S. Pat. No. 5,661,222 (1997).
34. D. J. Harrison et al., *Science,* 261: 895 (1993)
35. J.P. Brody, "Valveless Microswitch, U.S. Pat. No. 5,656,155 (1998).
36. Aine, H. E., et al., U.S. Pat. No. 4,585,209 (1986).
37. Baker, D. R., in Capillary Electrophoresis, John Wiley Sons, New York, 1995.
38. Ballantyne, J. P., et al., J. Vac. Sci. Technol. 10:1094 (1973).
39. Castro, A., et al., Anal. Chem. 85:849-852 (1993).
40. Goodwin, P. M., et: al., Nucleic Acids Research 21(4): 803-806 (1993).
41. Gravesen, P., et: al., U.S. Pat. No. 5,452,878 (1995).
42. Haugland, R. P., in Handbook of Fluorescent Probes and Research Chemicals, 5th Ed., Molecular Probes, Inc., Eugene, Oreg. (1992).
43. Keller, R. A., et al., GB Patent No. 2,264,296 (10/95).
44. Krutenat, R. C., Kirk-Othmer Concise Encyclopedia of Chemical Technology, John Wiley & Sons, New York (1985).
45. O'Connor, J. M., U.S. Pat. No. 4,581,624 (1986).
46. van Lintel, H. T. G., U.S. Pat. No. 5,271,274 (1993).
47. Wise, K. D., et al., U.S. Pat. No. 5,417,235 (1995).
48. Thompson, L. F., "Introduction to Lithography", ACS Symposium Series 219:1-13, (1983).
49. Angell et al., Scientific American 248:44-55 (1983).
50. Manz et al., Trends in Analytical Chemistry 10: 144-149 (1991)
51. Harrison et al., International Publication No. 98/52691, published Nov. 26, 1998.
52. Bein, Thomas, Efficient Assays for Combinatorial Methods for the Discovery of Catalysts, *Angew. Chem. Int. Ed.* 38:3, 323-26 (1999).
53. F. H. Arnold, *Acct. Chem. Research* 31, 125-131 (1998).
54. Hanes, J. & Pluckthun A. *Proc. Nat. Acad. Sci., USA* 94, 4937 (1997).
55. Hoffmuller, U. & J. Schneider-Mergener, *Angew. Chemie. Int. Ed.* 37, 3241-3243 (1998).
56. Jermutus, L., L. A. Ryabova & A. Pluckthun, *Curr. Opin. Biotechnol.* 9, 534-548 (1998).
57. Roberts, R. W. & Szostak, J. W. *Proc. Natl. Acad. Sci. USA* 94, 12297-12302 (1997).
58. Stemmer, W. P. C. Nature, 370, 389 (1994)
59. Tawfik, D. and Griffiths, A. *Nat. Biotechnol.* 16, 656 (1998).
60. Sambrook et al., *Molecular Cloning: A Laboratory Manual 2nd Edition, Cold Spring Harbor Laboratory Press* (1989).
61. Benecke et al., U.S. Pat. No. 5,454,472 (1995).
62. J. Affholter and F. Arnold, "Engineering a Revolution," *Chemistry in Britain*, April 1999, p. 48.
63. H. Joo, Z. Lin and F. Arnold, "Laboratory evolution of peroxide-mediated cytochrome P450 hydroxylation," *Nature* (1999), in press.
64. Inoue, Shinya and Spring, Kenneth R., Video Microscopy: The Fundamentals, 2nd ed., Plenum Press, New York, N.Y. (1997).
65. Giusti, J. Forensic Sci. 31:409-417 (1986).
66. Kanter et al, J. Forensic Sci. 31:403-408 (1986)
67. Jeffreys et al., Nature 314:67-72 (1985)
68. Budowle et al., Am. J. Hum. Genet. 48:137-144 (1991)
69. Nakamura et al., Science 235:1616-22 (1987)
70. Crow et al., "The Evaluation of Forensic DNA Evidence," National Academy Press (1996)
71. Quake et al., "A Microfabricated Device for Sizing and Sorting DNA Molecules," PNAS 96:11-13 (1999)
72. A. T. Woolley, K. Q. Lao, A. N. Glazer and R. A. Mathies, "Capillary Electrophoresis Chips with Integrated Electrochemical Detection," *Analytical Chemistry,* 70 (4), pp. 684 (1998).
73. N. H. Chiem and D. J. Harrison, "Microchip Systems for Immunoassay: an Integrated Immunoreactor with Electrophoretic Separation for Serum Theophylline Determination," *Clinical Chemistry,* 44 (3), 591 (1998).
74. M. U. Kopp, A. J. de Mello and A. Manz, "Chemical Amplification: Continuous-flow PCR on a Chip," *Science,* 280 (5366), 1046 (1998).
75. L. C. Waters, S. C. Jacobson, N. Kroutchinina, J. Khandurina, R. S. Foote, and J. M. Ramsey, "Microchip devices for cell lysis, multiplex PCR amplification, and electrophoretic sizing," *Analytical Chemistry.,* 70 (1), 158 (1998).
76. M. A. Unger, H. P. Chou, T. Thorsen, A. Scherer and S. R. Quake, "Monolithic Microfabricated Valves and Pumps Using Multi-layer Soft Lithography," Science, 288(5463): 113-116, April 2000.
77. A. Y. Fu. C. Spence, A. Scherer, F. H. Arnold and S. R. Quake. "A Microfabricated Fluorescence-Activated Cell Sorter," *Nature Biotechnology,* 17, 1109 (1999).
78. R. S. Kane, S. Takayama, E. Ostuni, D. E. Ingber, and G. M. Whiteside, "Patterning Proteins and Cells Using Soft Lithography," *Biomaterials,* 20 (23-24), 2363 (1999).
79. E. Delamarche, A. Bernard, H. Schmid, B. Michel, and H. Biebuyck, "Patterned Delivery of Immunoglobulins to Surfaces Using Microfluidic Networks," *Science,* 276, 779 (1997).
80. P. M. Small, et al. P. C Hopewell, S. P. Singh, A. Paz, J. Parsonnet, D.C. Ruston, G. F. Schecter, C. L. Daley, and G. K. Schoolnik. The epidemiology of tuberculosis in San Francisco. New Eng. J. of Med., 330(24):1703-1709, 1994.

81. M. Chee, R. Yang, E. Hubbell, A. Berno, X. C. Huang, D. Stern, J. Winkler, D. J. Lockhart, M. S. Morris, and S. P. A. Fodor. Accessing genetic information with high-density DNA arrays. Science, 274(5287):610-614, 1996.
82. D. J. Lockhart, H. L. Dong, M. C. Byrne, M. T. Follettie, M. V. Gallo, M. S. Chee, M. Mittmann, C. W. Wang, M. Kobayashi, H. Horton, and E. L. Brown. Expression monitoring by hybridization to high-density oligonucleotide arrays. Nature Biotechnol., 14(13):1675-1680, 1996.
83. M. Schena, D. Shalon, R. W. Davis, and P. O. Brown. Quantitative monitoring of gene-expression patterns with a complementary-DNA microarray. Science, 270(5235):467-470, 1995.
84. A. T. Woolley, K. Q. Lao, A. N. Glazer, and R. A. Mathies. Capillary electrophoresis chips with integrated electrochemical detection. Anal. Chem., 70(4):684-688, 1998.
85. J. P. Brody and P. Yager. Low reynolds number microfluidic devices. In Proc. of Solid-State Sensor and Actuator Workshop, pages 105-108. Hilton Head, June 1996.
86. L. J. Guo, P. R. Krauss and S. Y. Chou. *Appl. Phys. Lett.* 71, 1881 (1997).
87. M. T. Li, J. A. Wang, L. Zhuang and S. Y. Chou, *Appl. Phys. Lett.* 76, 673 (2000).
88. H. P. Chou, Ph.D. Thesis: *Microfabricated Devices for Rapid DNA Diagnostics* (California Institute of Technology, Pasadena, Calif., 2000) Chapter 3.
89. Kenis, "Microfabrication inside capillaries using multiphase laminar flow patterning", *Science* 1999, 285:83.

What is claimed is:

1. A method for effectively mixing two or more different fluids in a microfluidic device, which method comprises:
    (a) introducing the different fluids to a microfluidic device, the microfluidic device having:
        (i) a loop channel communicating with at least one service channel, and
        (ii) a pump associated with the loop channel, so that each of the different fluids is loaded into the loop channel; and
    (b) circulating the different fluids using the pump associated with the loop channel to mix the different fluids, wherein the pump is a peristaltic pump comprising at least three cooperating microvalves acting within the loop channel.

2. A method according to claim 1, wherein the microfluidic device has at least one inlet channel and at least one outlet channel, the different fluids being loaded into the loop channel through at least one inlet channel.

3. A method according to claim 2, wherein:
    the microfluidic device has two or more inlet channels; and
    each of the two or more different fluids is loaded into the loop channel through a different inlet channel.

4. A method according to claim 2, wherein each inlet channel and each outlet channel is separated from the loop channel by a microvalve.

5. A method according to claim 4, wherein the microvalves separating the inlet and outlet channels from the loop channel are closed while the pump is activated.

6. A method according to claim 4, wherein the microvalves separating the inlet and outlet channels from the loop channel remain open while the pump is activated.

7. A method according to claim 1, wherein at least one of the different fluids comprises a solution of molecules.

8. A method according to claim 7, wherein the solution of molecules contains molecules selected from a group consisting of: nucleic acid molecules, polypeptide molecules, antibody molecules.

9. A method according to claim 1, wherein at least one of the different fluids comprises a suspension of particles.

10. A method according to claim 9, wherein the suspension of particles contains particles selected from a group consisting of: cells, virions, and microscopic beads.

11. A method according to claim 1, wherein the microfluidic device further comprises a microvalve separating the loop channel from the service channel.

12. A method for binding a sample to a target, which method comprises:
    (a) introducing a fluid containing the sample to a microfluidic device, the microfluidic device having:
        (i) a loop channel communicating with at least one service channel and having molecules of the target disposed therein, and
        (ii) a pump associated with the loop channel, so that the fluid containing the sample is loaded into the loop channel; and
    (b) circulating the fluid through the loop channel using the pump, wherein the sample binds to the target molecules disposed in the loop as the fluid circulates therethrough, and wherein the pump is a peristaltic pump comprising at least three cooperating microvalves acting within the loop channel.

13. A method according to claim 12, wherein the target molecules are selected from a group consisting of polynucleotide probes, protein probes, antibody probes, biotin and avidin.

14. A method according to claim 12, wherein the sample comprises nucleic acid molecules, protein molecules, cells or virions.

15. A method according to claim 14, wherein
    the sample comprises nucleic acid molecules, and
    the target comprises polynucleotide probes specific for nucleic acid molecules in the sample.

16. A method according to claim 14, wherein:
    the target comprises biotin molecules, and
    the sample comprises particles or molecules having a biotin specific label.

17. A method according to claim 12, wherein the loop channel resides in a layer of elastomeric material.

18. A method according to claim 12, wherein the microfluidic device further comprises a microvalve separating the loop channel from the service channel.

* * * * *

UNITED STATES PATENT AND TRADEMARK OFFICE
CERTIFICATE OF CORRECTION

| | | |
|---|---|---|
| PATENT NO. | : 8,129,176 B2 | Page 1 of 1 |
| APPLICATION NO. | : 12/536129 | |
| DATED | : March 6, 2012 | |
| INVENTOR(S) | : Stephen R. Quake et al. | |

It is certified that error appears in the above-identified patent and that said Letters Patent is hereby corrected as shown below:

Please replace the paragraph in column 1, lines 18-21 with the following paragraph:

-- This invention was made with government support under Grant No. HG01642-03 awarded by the National Institutes of Health. The government has certain rights in the invention. --

Signed and Sealed this
Seventeenth Day of April, 2012

David J. Kappos
*Director of the United States Patent and Trademark Office*